United States Patent
Turino et al.

(10) Patent No.: US 9,885,727 B2
(45) Date of Patent: Feb. 6, 2018

(54) CELL CULTURE MODELS FOR VALIDATING CANDIDATE COMPOUNDS FOR USE IN TREATING COPD AND OTHER DISEASES

(71) Applicant: THE TRUSTEES OF COLUMBIA UNIVERSITY IN THE CITY OF NEW YORK, New York, NY (US)

(72) Inventors: Gerard M Turino, New York, NY (US); Shuren Ma, Cliffside Park, NJ (US); Yong Y Lin, Bridgewater, NJ (US); Seymour Leiberman

(73) Assignees: St. Luke's-Roosevelt Hospital Center, New York, NY (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/712,811

(22) Filed: May 14, 2015

(65) Prior Publication Data

US 2015/0355193 A1    Dec. 10, 2015

Related U.S. Application Data

(60) Division of application No. 13/836,332, filed on Mar. 15, 2013, now Pat. No. 9,068,942, which is a continuation of application No. 13/575,346, filed as application No. PCT/US2011/022619 on Jan. 26, 2011, now abandoned.

(60) Provisional application No. 61/336,804, filed on Jan. 26, 2010.

(51) Int. Cl.
| | |
|---|---|
| *G01N 27/62* | (2006.01) |
| *G01N 33/68* | (2006.01) |
| *H01J 49/00* | (2006.01) |
| *G01N 30/72* | (2006.01) |
| *G01N 30/88* | (2006.01) |

(52) U.S. Cl.
CPC ......... *G01N 33/6887* (2013.01); *G01N 27/62* (2013.01); *G01N 30/7233* (2013.01); *G01N 33/6848* (2013.01); *G01N 33/6881* (2013.01); *H01J 49/005* (2013.01); *H01J 49/0027* (2013.01); *G01N 2030/8831* (2013.01); *G01N 2333/78* (2013.01); *G01N 2500/00* (2013.01); *G01N 2500/10* (2013.01); *G01N 2800/00* (2013.01); *G01N 2800/122* (2013.01); *Y10T 436/145555* (2015.01)

(58) Field of Classification Search
None
See application file for complete search history.

(56) References Cited

U.S. PATENT DOCUMENTS

| | | | |
|---|---|---|---|
| 5,217,903 A | 6/1993 | Stone et al. | |
| 5,354,662 A | 10/1994 | Stone et al. | |
| 5,502,197 A | 3/1996 | Daniloff et al. | |
| 5,756,679 A * | 5/1998 | Daniloff | C07D 213/65 436/87 |
| 9,068,942 B2 * | 6/2015 | Turino | G01N 30/7233 |
| 2010/0196885 A1 * | 8/2010 | Turino | G01N 33/5088 435/6.14 |
| 2015/0025019 A1 * | 1/2015 | Cantor | A61K 31/728 514/20.4 |

FOREIGN PATENT DOCUMENTS

WO    2008091633 A1    7/2008

OTHER PUBLICATIONS

Ma S. et al. The Detection and Quantitation of Free Desmosine and Isodesmosine . . . PNAS 100(22)12941-3, Oct. 28, 2003.*
Boutin M. et al. High Sensitivity NanoLC-MS/MS Analysis of Urinary Desmosine and Isodesmosine. Analytical Chemistry 81(5)1881-7, Mar. 1, 2009.*
Ma S. et al. Measurements of Desmosine and Isodesmosine by MS in COPD. Chest 131(5)1363-71, May 2007.*
Iso et al., "Passive smoking and plasma fibrinogen concentrations." Am J of Epidemiology, 144:1151-1154 1996.
James et al., "Automated solid-phase extraction with high-performance liquid chromatography analysis of pyridinium crosslinks," Anal Biochem, 240:29-36 1996.
Kaga et al., "Quantification of elastin crosslinking amino acids, desmosine and isodesmosine, in hydrolysates of rat lung by ion-pair liquid chromatography-mass spectrometry," Anal Biochem, 318:25-9 2003.

(Continued)

*Primary Examiner* — Ralph J Gitomer
(74) *Attorney, Agent, or Firm* — Bryan Cave LLP

(57) ABSTRACT

The present invention relates to methods of diagnosing, monitoring, and treating elastin fiber injuries. In additional preferred embodiments, the present invention relates to methods of validating candidate compounds for use in treating chronic obstructive pulmonary disease (COPD), chronic bronchitis, emphysema, refractory asthma, and other related diseases. Examples of such methods include determining if the candidate compound decreases the degradation of elastic fiber in a patient administered the candidate compound by measuring, using mass spectrometry employing an internal standard, a marker of elastic fiber degradation in a sample of a body fluid or a tissue of the patient. The invention provides that a decrease in the presence of the marker compared to a control validates that the candidate compound is effective to treat, prevent, or ameliorate the disease.

7 Claims, 36 Drawing Sheets

(56) References Cited

OTHER PUBLICATIONS

Kindt et al., "Quantitative method for biomarkers of collagen degradation using liquid chromatography tandem mass spectrometry," Anal Biochem, 283:71-6 2000.
King et al., "Radioimmunoassay for desmosine," Connect Tissue Res, 7:263-7 1980.
Lee et al., "Antielastin autoimmunity in tobacco smoking-induced emphysema," Nat Med, 13:567-569 2007.
Luisetti et al., "Desmosine as a biomarker of elastin degradation in COPD: Current status and future directions," Eur Respir J, 32:1146-57 2008.
Ma et al., "The detection and quantitation of free DID in human urine and their peptide-bound forms in sputum," Proc Natl Acad Sci USA, 100:12941-12943 2003.
Ma et al., "The effect of tiotropium therapy on markers of elastin degradation in COPD," Respir Res, vol. 10, available Online at http://respiratory-research.com/content/1 0/1/12, 7 pages 2009.
Ma et al., "Measurements of desmosine and isodesmosine by mass spectrometry in COPD," Chest, 131:1363-71 2007.
Mascarenhas et al., "Low molecular weight hyaluronan from stretched lung enhances interleukin-8 expression," Am J Respir Cell Mol Bioi, 30:51-60 2004.
McKee et al., "Hyaluronan (HA) fragments induce chemokine gene expression in alveolar macrophages. The role of HA size and CD44," J Clin Invest, 98:2403-2413 1996.
Mecham et al., "Elastin degradation by matrix metalloproteinases cleavage site specificity and mechanisms of elastolysis," J Bioi Chern, 272:18071-18076 1997.
Mecham et al., "Structural model for desmosine crosslinked peptides," Biochem J, 173:617-625 1978.
Menzies et al., "Respiratory symptoms, pulmonary function, and markers of inflammation among bar workers before and after a legislative ban on smoking in public places," JAMA, 296:1742-1748 2006.
Morelli et al., "Structure-activity relationships for some elastin-derived peptide chemoattractants," J Pept Res, 49:492-499 1997.
Murakami et al., "Effects of hyaluronidase on porcine pancreatic elastase-induced lung injury," J Jpn Respir Soc, 36:577-584 1998.
Nadkarni et al., "Dichotomous effect of aerosolized hyaluronan in a hamster model of endotoxin-induced lung Injury," Exp Lung Res, 31:807-818 2005.
Nakano et al., "Quantitative assessment of airway remodeling using high-resolution CT," Chest, 122:271S-275S 2002.
Newell et al., "Report of a workshop: quantitative computed tomography scanning in longitudinal studies of emphysema," Eur Respir J, 23:769-775 2004.
Otsuka et al., "Acute effects of passive smoking on the coronary circulation in healthy young adults," JAMA, 286:436-441 2001.
Owen, "Roles for proteinases in the pathogenesis of chronic obstructive pulmonary disease," Int J Chron Obstruct Pulmon Dis, 3:253-268 2008.
Gottlieb et al., "Urinary desmosine excretion in smokers with and without rapid decline of lung function the normative aging study," Am J Respir Crit Care Med, 154: 1290-1295 1996.
Harel et al., "Desmosine radioimmunoassay for measuring elastin degradation in vivo," Am Rev Respir Dis, 122:769-73 1980.
Hogg et al., "The pathology of chronic obstructive pulmonary disease," Ann Rev Pathol Mech Dis, 4:435-459 2009.
Houghton et al., "Elastin fragments drive disease progression in a murine model of emphysema," J Clin Invest, 116, available online www.ncbi.nlm.nih.gov/pmc/articles/PMC1361346/, 7 pages 2006.
Hunninghake et al., "Elastin fragments attract macrophage precursors to diseased sites in pulmonary-emphysema," Science, 212:925-927 1981.
Indik et al., "Alternative splicing of human elastin messenger-RNA indicated by sequence analysis of cloned genomic and complementary-DNA," Proc Natl Acad Sci USA, 84:5680-5684 1987.

Panagiotakos et al., "Effect of exposure to secondhand smoke on markers of inflammation: the ATTICA study," Am J of Med, 116: 145-150 2004.
Papayannopoulos, "The interpretation of collision-induced dissociation tandem mass-spectra of peptides," Mass Spectrom Rev, 14:49-73 1995.
Pauwels et al., "Global strategy for the diagnosis, management, and prevention of chronic obstructive pulmonary disease. NHLBI/WHO global initiative for Chronic Obstructive Lung Disease (GOLD) workshop summary," Am J Respir Crit Care Med, 163:1256-76 2001.
Prati et al., "Automated analysis of the pyridinium crosslinks of collagen in tissue and urine using solid-phase extraction and reversed-phase high-performance liquid chromatography," Anal Biochem, 207:168-175 1992.
Reiser et al., "Enzymatic and nonenzymatic cross-linking of collagen and elastin," FASEB J, 6:2439-2449 1992.
Rosenbloom,. "Elastin: Biosynthesis, structure, degradation and role in disease processes," Connect Tissue Res, 10:73-91 1982.
Russell et al., "Alveolar macrophage mediated elastolysis: roles of matrix metalloproteinases, cysteine, and serine proteases," Am J Physiol Lung Cell Mol Physiol, 283:L867-L873 2002.
Sandberg et al., "Elastin structure, biosynthesis, and relation to disease states," N Engl J Med, 304:566-579 1981.
Sandberg, "Elastin structure in health and disease," Int Rev Connect Tissue Res, 7:159-210 1978.
Schriver et al., "Comparison of elastin peptide concentrations in body-fluids from healthy-volunteers, smokers, and patients with chronic obstructive pulmonary-disease," Am Rev Respir Dis, 145:762-6 1992.
Schwartz et al., "Determination of desmosines in elastin-related skin disorders by isocratic high-performance liquid chromatography," Exp Mol Pathol, 52:63-8 1990.
Scan et al.. "Secondary and tertiary structures of hyaluronan in aqueous solution. investigated by rotary shadowing-electron microscopy and computer simulation. Hyaluronan is a very efficient network-forming polymer," Biochem J, 274 (Pt 3), 699-705 1991.
Senior et al., "Lung elastin and elastase in COPD," Eur Resp Rev, 12:316-319 2002.
Senior., "Chemotactic activity of elastin-derived peptides," J Clin Invest, 66:859-862 1980.
Senior et al., "Vai-Giy-Vai-Aia-Pro-Giy, a repeating peptide in elastin, is chemotactic for fibroblasts and monocytes," J Cell Bioi, 99:870-874 1984.
Senior et al., "Chemotactic responses of fibroblasts to tropoelastin and elastin-derived peptides," J Clin Invest, 70:614-618 1982.
Shapiro, "Proteinases in chronic obstructive pulmonary disease." Biochem Soc Trans, 30:98-102 2002.
Shapiro et al., "Molecular cloning, chromosomal localization, and bacterial expression of a murine macrophage metalloelastase," J Bioi Chern. 267:4664-4671 1992.
Shapiro, "Cloning and characterization of a unique elastolytic metalloproteinase produced by human alveolar macrophages," J Bioi Chern. 268:23824-23829 1993.
Shimada et al., "An approach to the study of the structure of desmosine and isodesmosine containing peptides isolated from the elastase digest of elastin," Biochem Biophys Res Commun, 37:191-7 1969.
Snider et al., "Animal-models of emphysema," Am Rev Respir Dis, 133:149-169 1986.
Starcher et al., "The kinetics of elastolysis: elastin catabolism during experimentally induced fibrosis," Exp Lung Res, 25:407-424 1999.
Starcher et al.. "Purification and comparisons of elastin from different animal species." Analytical Biochemistry, 74:441-447 1976.
Stolk et al., "Short-term variability of biomarkers of proteinase activity in patients with emphysema associated with type Z alpha-1 antitrypsin deficiency," Respir Res, vol. 6, available at respiratory-research.com/content/6/1/47, 7 pages, 2005.
Stone et al., "Measurement of urinary desmosine by isotope-dilution and high-performance liquid-chromatography-correlation between

(56) References Cited

OTHER PUBLICATIONS elastase-induced air-space enlargement in the hamster and elevation of urinary desmosine," Am Rev Respir Dis, 144:284-90 1991.
Stone et al., "Elastin and collagen degradation products in urine of smokers with and without chronic obstructive pulmonary disease," Am J Respir Crit Care Med, 151:952-9 1995.
Stone et al., "Elastin and collagen degradation products in urine of patients with cystic fibrosis," Am J Respir Crit Care Med, 152:157-62 1995.
Stone et al., "Cross-linked elastin and collagen degradation products in the urine of patients with scleroderma," Arthritis Rheumatism, 38:517-24 1995.
Stone, "Potential use of collagen and elastin degradation markers for monitoring liver fibrosis I schistosomiasis," Acta Trop, 77:97-9 2000.
Ten Holder et al., "Urinary desmosine excretion as a marker of lung injury in the adult respiratory distress syndrome," Chest, 100:1385-1390 1191.
Thomas et al., "Degradation products from elastin: Partial structure of two major degradation products from the cross-linkages in elastin," Nature, 200:651-2 1963.
FDA Study Group on "Improving Endpoints, Improving Care: Alpha-1 Antitrypsin Augmentation Therapy and Clinical Trials" Center for Biologics Evaluation and Research, FDA, Bethesda, Maryland. Mar. 23-24, 2009.
Turino et al., "Serum elastase inhibitor deficiency and alpha1-antitrypsin deficiency in patients with obstructive emphysema," Science, 165:709-711 1969.
Twumasi et al., "Protease from purulent sputum, purification and properties of the elastase and chenzymes," J Bioi Chem, 252:1917-1926ymotrypsin-like 1977.
Tzortzaki et al., "Biomarkers in COPD," Curr Med Chem, 14:1037-1048 2007.
Urry, "Entropic elastic processes in protein mechanisms. 1. Elastic structure due to an inverse temperature transition and elasticity due to internal chain dynamics," J Protein Chem, 7:1-34 1988.
Urry, "Protein elasticity based on conformations of sequential polypeptides the biological elastic fiber," J Protein Chem, 3:403-436 1984.
Venn et al., "Exposure to secondhand smoke and biomarkers of cardiovascular disease risk in never-smoking adults," Circulation, 115:990-995 2007.
Viglio et al., "MEKC of DID in urine of chronic destructive lung disease patients," Eur Respir J, 388 15:1039-1045 2000.
Viglio et al.. "Micellar electrokinetic chromatography for the determination of urinary desmosine and isodesmosine in patients affected by chronic obstructive pulmonary disease," J Chromatogr B, 714:87-98 1998.
Vlahovic et al., "Cellular and connective tissue changes in alveolar septal walls in emphysema," Am J Respir Crit Care Med, 160:2086-2092 1999.
Vrhovski et al. "Biochemistry oftropoelastin," Eur J Biochem, 258:1-18 1998.
Watanabe et al., "Alteration of cross-linking amino acids of elastin in human aorta in association with dissecting aneurysm: Analysis using high performance liquid chromatography," Tohoku J Exp Med, 187:291-303 1999.
Whincup et al., "Passive smoking and risk of coronary heart disease and stroke: prospective study with cotinine measurement," BMJ, 10:1-6 2004.
World Health Organization—Environmental burden of disease series, No. 18: Second Hand Smoke who.int/quantifying_ehimpacts/publications/ebd18/en/ 2010.
World Health Organization fact sheet No. 315 who.int/mediacentre/factsheets/fs315/en/. 2012.
Wright et al., "Smoke-induced emphysema in guinea pigs is associated with morphometric evidence of collagen breakdown and repair," Am J Physiol Lung Cell Mol Physiol, 12:17-20 1995.
Wright, "Elastic tissue of normal and emphysematous lungs—a tridimensional histologic study," Am J Pathol, 39:355-67 1961.

Wurzel et al., "Oxidative damage and antioxidant status in the lungs and bronchoalveolar lavage fluid of rats exposed chronically to cigarette smoke," J Biochem Toxicol, 10:11-17 1995.
Yamazaki et al., "Human blood concentrations of cotinine, a biomonitoring marker for tobacco smoke, extrapolated from nicotine metabolism in rats and humans and physiologically based pharmacokinetic modeling," Int J Environ Res Public Health, 7:3406-21 2010.
Yoshida et al., "Pathobiology of cigarette smoke-induced chronic obstructive pulmonary disease," Physiol Rev, 87:1047-82 2007.
Yusa et al., Tumor-cell interactions with elastin implications for pulmonary metastasis, Am Rev Respir Dis, 140:1458-1462 1989.
Abraham et al., "Marian syndrome: Demonstration of abnormal elastin in aorta," J Clin Invest, 70:1245-52 1982.
Akagawa et al., "Mechanism of formation of elastin crosslinks," Connect Tissue Res, 41:131-41 2000.
Akers et al., "Specificity and sensitivity of the assay for elastin-derived peptides in chronic obstructive pulmonary disease," Am Rev Respir Dis, 145:1077-1081 1992.
Albarbarawi et.al., "Measurement of urinary total desmosine and isodesmosine using isotope-dilution liquid chromatography-tandem mass spectrometry," Anal Chem, 82:3745-50 2010.
Annovazzi et al., "High level of desmosine in urine and plasma of patients with pseudoxanthoma elasticum," Eur J Clin Invest, 34:156-64 2004.
Baccarani-Contri et al., Immunocytochemical localization of proteoglycans within normal elastin fibers, Eur J Cell Bioi, 53:305-312 1990.
Banda et al., "Mouse macrophage elastase. Purification and characterization as metalloproteinase," Biochem J, 193:589-605 1981.
Barnes, "Mediators of chronic obstructive pulmonary disease," Pharmacol Rev, 56:515-548 2004.
Barnes et al., "Chronic obstructive pulmonary disease: molecular and cellular mechanisms," Eur Respir J, 22:672-678 2003.
Barnes, "Chronic Obstructive Pulmonary Disease," New England J of Med, 343(4): 269-280 2000.
Barroso et al., "Study of human lung elastin degradation by different elastases using high-performance liquid chromatography/mass spectrometry," Anal Biochem, 358:216-224 2006.
Baskaran et al.. "Effect of cigarette smoke on lipid peroxidation and antioxidant enzymes in albino rat." Indian J Exp Bioi, 37:1196-2000 1999.
Benowitz, "Cotinine as a biomarker of environmental tobacco smoke exposure," Epidemiol Rev, 18:188-204 1996.
Biemann, "Sequencing of peptides by tandem mass spectrometry and high-energy collision-induced dissociation," Methods Enzymol, 193:455-479 1990.
Bode et al., "Comparison of urinary desmosine excretion in patients with chronic obstructive pulmonary disease or cystic fibrosis," Pulm Pharmacol Ther, 13:175-80 2000.
Boschetto et al., "Association between markers of emphysema and more severe chronic obstructive pulmonary disease," Thorax, 61:1037-1042 2006.
Boutin et al., "High-sensitivity nanoLC-MS/MS analysis of urinary desmosine and isodes mosine," Anal Chem, 81:1881-7 2009.
Brassart et al., "Conformational dependence of collagenase (matrix metalloproteinase-1) up-regulation by elastin peptides in cultured fibroblasts," J Bioi Chem., 276:5222-5227 2001.
Brown-Augsburger et al., "Identification of an elastin cross-linking domain that joins 3 peptide chains possible role in nucleated assembly," J Bioi Chem, 270:17778-17783 1995.
Cantor et al., "Pulmonary air-space enlargement induced by intratracheal instillment of hyaluronidase and concomitant exposure to 60% oxygen," Exp Lung Res, 19:177-192 1993.
Cantor et al., "Further investigation of the use of intratracheally administered hyaluronic acid to ameliorate elastase-induced emphysema," Exp Lung Res, 23(3):229-244 1997.
Cantor et al., "Aerosolized hyaluronic acid decreases alveolar injury induced by human neutrophil elastase," Proc Soc Exp Bioi Med, 217:471-475 1998.
Cantor et al., "Modulation of airspace enlargement in elastase-induced emphysema by intratracheal instillment of hyaluronidase and hyaluronic acid," Exp Lung Res, 21:423-436 1995.

(56) References Cited

OTHER PUBLICATIONS

Cantor et al., "Aerosolized hyaluronan limits airspace enlargement in a mouse model of cigarette smoke-induced pulmonary emphysema," Exp Lung Res, 31:417-430 2005.
Cantor et al., "The effect of hyaluronan on elastic fiber injury in vitro and elastase-induced airspace enlargement in vivo," Proc Soc Exp Bioi Med, 225:65-71 2000.
Celli, "The importance of spirometry in COPD and asthma: effect on approach to management," Chest, 117(2 Suppl): 357 15S-19S 2000.
Chen et al., "Direct detection of crosslinks of collagen and elastin in the hydrolysates of human yellow ligament using single-column high performance liquid chromatography," Anal Biochem, 278:99-105 2000.
Chrzanowski et al., Elastin content of normal and emphysematous lung parenchyma, Am. J Med, 69: 351-359 1980.
Clark III et al., "Inflammatory markers and secondhand tobacco smoke exposure among U.S. workers," Am J of Industrial Medicine, 51:626-632 2008.
Cocci et al., "Urinary desmosine excretion is inversely correlated with the extent of emphysema in patients with chronic obstructive pulmonary disease," Int J Biochem Cell Bioi, 34:594-604 2002.
Comhair et al., "Antioxidant responses to oxidant-mediated lung diseases," Am J Physiol Lung Cell Mol Physiol, 283: L246-L255 2002.
Cosio et al., "Immunologic aspects of chronic obstructive pulmonary disease," N Engl J Med, 360:2445-2454 2009.
Cumiskey et al., "Enrichment and analysis of desmosine and isodesmosine in biological fluids," J Chromatogr B, 668:199-207 1995.
Darnule et al.. Solid-phase radioimmunoassay for estimation of elastin peptides in human-sera. Anal Biochem, 122:302-307 1982.
Dillon et al., "Plasma elastin-derived peptide levels in normal adults, children, and emphysematous subjects physiological and computed tomographic scan correlates," Am Rev Respir Dis, 146:1143-1148 1992.
Djekic et al., "Attacking the multi-tiered proteolytic pathology of COPD: new insights from basic and translational studies," Pharmacol Ther, 121:132-146 2009.
Dunnill, "Quantitative methods in the study of pulmonary pathology," Thorax, 17:320-328 1962.
Fiorenza et al., "Urinary desmosine excretion in acute exacerbations of COPD: a preliminary report," Respir Med, 96:110-114 2002.
Fiorenza et al., "Urinary desmosine excretion in acute exacerbations of COPD: a preliminary report," Respir Med, 96:110-114 2009.
Flouris et al., "Acute and short-term effects of secondhand smoke on lung function and cytokine production," Am J Respir Crit Care Med, 179:1029-1033 2009.
Foster et al., "Circular-dichroism studies of an elastin crosslinked peptide. Biopolymers," 15:833-841 1976.
Fukuda et al., "Morphogenesis of abnormal elastic fibers in lungs of patients with panacinar and centriacinar emphysema," Hum Pathol, 20:652-659 1989.
Gerber et al., "Comparative studies of the crosslinked regions of elastin from bovine ligamentum nuchae and bovine, porcine and human aorta," Biochem J, 149:685-695 1975.
Giummell Yet al., "Measurement of desmosine and isodesmosine by capillary zone electrophoresis," J Chromatogr, 710:357-60 1995.
Gosline, "Hydrophobic interaction and a model for elasticity of elastin. Biopolymers," 17:677-695 1978.

\* cited by examiner

Fig. 5

Patients of Chronic Obstructive Pulmonary Disease with Normal Alpha 1-Antitrypsin

| Subjects | Sex | Age | Race | FVC | FEV$_1$ | RV/TLC | D$_{L,CO}$ | Desmosine/Isodesmosine | | | | | | |
|---|---|---|---|---|---|---|---|---|---|---|---|---|---|---|
| | | | | | | | | Plasma | | Urine | | | Sputum | |
| | | | | | | | | ng/ml | ng/g protein | Free Form μg/g creatinine | Total | Free/Total % | ng/ml | ng/g protein |
| | | | | | | % predicted | | | | | | | | |
| 1 | F | 60 | AA | 66 | 45 | 118 | 45 | 0.70/0.63 | 9.00/8.10 | 3.56/3.12 | 7.11/5.32 | 50/59 | 0.04/0.02 | 6.96/3.64 |
| 2 | F | 67 | C | 97 | 55 | 63 | 68 | 0.47/0.15 | 6.51/2.08 | 3.30/2.60 | 6.90/5.22 | 48/50 | 0.11/0.04 | 12.35/4.49 |
| 3 | M | 44 | AA | 66 | 43 | 162 | 49 | 0.19/0.13 | 2.82/1.84 | 2.52/1.96 | 5.05/3.98 | 50/49 | 0.20/0.15 | 7.94/5.95 |
| 4 | M | 48 | C | 76 | 73 | | | 0.30/0.12 | 6.94/2.77 | 3.82/2.25 | 6.13/4.83 | 62/47 | 0.56/0.52 | 215.38/200.00 |
| 5 | M | 72 | C | 76 | 57 | 157 | 76 | 0.26/0.17 | 5.21/3.41 | 4.39/3.24 | 8.80/6.18 | 50/52 | 0.65/0.51 | 39.42/30.93 |
| 6 | M | 58 | C | 66 | 37 | 168 | 78 | 0.49/0.44 | 9.32/8.37 | 3.43/2.41 | 6.85/5.63 | 50/43 | | |
| 7 | M | 85 | C | 106 | 60 | 123 | 60 | 0.29/0.18 | 6.39/3.97 | 4.58/3.49 | 12.09/9.84 | 38/35 | 0.26/0.27 | 17.66/18.34 |
| mean | | | | | | | | 0.39/0.26 | 6.60/4.36 | 3.66/2.72 | 7.56/5.86 | 50/48 | 0.30/0.25 | 49.95/43.89 |
| ±SEM | | | | | | | | ±0.07/±0.07 | ±0.84/±1.04 | ±0.26/±0.21 | ±0.87/±0.71 | ±3/±3 | ±0.10/±0.09 | ±33.44/±31.52 |

Race: AA = African-American, C = Caucasian

Fig. 6

Patients With Alpha 1-Antitripsin Deficiency Related COPD

| Subjects | Sex | Age | Race | FVC | FEV1 | RV/TLC | DLCO | Desmosine/Isodesmosine | | | | | | |
|---|---|---|---|---|---|---|---|---|---|---|---|---|---|---|
| | | | | | | | | Plasma | | Urine | | | Sputum | |
| | | | | | % Predicted | | | ng/ml | ng/g protein | Free Form | Total | Free/Total | ng/ml | ng/g protein |
| | | | | | | | | | | μg/g creatinine | | % | | |
| 1 | M | 57 | C | 68 | 42 | 103 | 39 | 1.59/1.11 | 44.75/31.24 | 2.08/0.97 | 6.03/4.82 | 34/20 | 2.14/1.46 | 720.54/491.58 |
| 2 | M | 47 | C | 43 | 19 | 139 | 17 | 0.30/0.25 | 5.95/4.95 | 2.57/1.67 | 5.62/2.43 | 46/69 | 0.56/0.39 | 29.47/20.17 |
| 3 | M | 54 | C | 80 | 68 | 110 | 41 | 1.24/0.95 | 21.44/16.43 | 1.99/1.17 | 5.27/4.68 | 38/25 | 1.52/1.42 | 894.12/835.29 |
| 4 | F | 49 | C | 66 | 57 | | 40 | 0.41/0.18 | 7.43/3.26 | 2.26/1.77 | 5.37/5.05 | 42/35 | 0.24/0.08 | 12.64/3.95 |
| 5 | F | 64 | C | 46 | 21 | 132 | 32 | 0.14/0.11 | 2.92/2.30 | 4.22/4.16 | 8.98/7.90 | 47/53 | | |
| 6 | M | 57 | C | 51 | 18 | 125 | 26 | 0.46/0.41 | 12.18/10.86 | 2.59/2.26 | 9.09/7.59 | 28/30 | 2.95/1.00 | 1031.47/349.65 |
| 7 | M | 52 | C | 43 | 22 | 214 | | 0.44/0.54 | 8.73/10.72 | 4.05/3.18 | 7.57/6.32 | 54/50 | 0.90/0.92 | 134.66/137.30 |
| 8 | M | 51 | C | 89 | 50 | 157 | 66 | 2.31/1.75 | 34.44/26.09 | 4.66/3.26 | 10.72/9.78 | 43/33 | 0.49/0.23 | 16.00/7.6 |
| 9 | F | 65 | C | 78 | 26 | 130 | 24 | 1.17/0.83 | 18.33/13.00 | 3.53/2.29 | 8.37/7.07 | 42/32 | 1.25/1.08 | 238.33/182.20 |
| 10 | M | 63 | C | 60 | 44 | 160 | 62 | 0.40/0.37 | 9.47/8.76 | 3.85/2.31 | 7.79/6.03 | 49/38 | 0.86/0.60 | 69.14/56.51 |
| 11 | M | 52 | C | 109 | 73 | 28 | 83 | 0.69/0.71 | 14.75/15.18 | 1.52/0.91 | 5.62/3.77 | 27/24 | 0.14/0.16 | 35.79/39.18 |
| 12 | F | 49 | C | 71 | 40 | 191 | 34 | 0.21/0.18 | 4.71/4.18 | 2.35/1.88 | 8.13/6.57 | 29/29 | 0.87/0.71 | 252.07/214.88 |
| mean | | | | | | | | 0.78/0.62 | 19.24/15.03 | 2.97/2.15 | 7.38/6.00 | 40/37 | 1.08/0.74 | 312.20/212.57 |
| ±SEM | | | | | | | | ±0.19/±0.14 | ±5.22/±3.71 | ±0.30/±0.29 | ±0.51/±0.58 | ±3/±4 | ±0.26/±0.15 | ±115.06/±77.93 |

Race: C = Caucasian

Fig. 9

| Patients | TIO | Urine (μg/g creatinine) Free  F/T(%) | | Plasma (ng/mL) | Sputum (ng/mL) | Patients | TIO | Urine (μg/g creatinine) Free  F/T(%) | | Plasma (ng/mL) | Sputum (ng/mL) |
|---|---|---|---|---|---|---|---|---|---|---|---|
| #1 | 0 month | 6.57 | 49.6 | 0.42 | 0.93 | #7 | 0 month | 3.40 | 40.9 | 0.62 | 0.23 |
|    | 1 month | 4.99 | 48.5 | 0.37 | 0.15 |    | 1 month | 5.38 | 40.2 | 0.63 | 0.30 |
|    | 2 month | 5.29 | 38.5 | 0.47 | 0.05 |    | 2 month | 4.79 | 37.4 | 0.61 | 0.22 |
| #2 | 0 month | 9.50 | 40.8 | 0.71 | 0.77 | #8 | 0 month | 3.76 | 39.4 | 0.52 | 0.27 |
|    | 1 month | 5.91 | 41.9 | 0.67 | 0.19 |    | 1 month | 3.48 | 35.3 | 0.39 | 0.29 |
|    | 2 month | 7.50 | 32.7 | 0.45 | 0.33 |    | 2 month | 3.15 | 35.0 | 0.42 | 0.13 |
| #3 | 0 month | 3.90 | 35.1 | 0.71 | 0.52 | #9 | 0 month | 6.61 | 63.2 | 0.51 | 0.18 |
|    | 1 month | 5.37 | 38.1 | 0.54 | 0.26 |    | 1 month | 5.26 | 43.0 | 0.64 | 0.22 |
|    | 2 month | 4.45 | 39.9 | 0.33 | 0.10 |    | 2 month | 4.71 | 39.1 | 0.46 | 0.10 |
| #4 | 0 month | 5.14 | 45.0 | 0.77 | 0.33 | #10 | 0 month | 7.59 | 50.7 | 0.75 | 0.19 |
|    | 1 month | 4.82 | 42.3 | 0.40 | 0.23 |    | 1 month | 5.98 | 46.6 | 0.46 | 0.12 |
|    | 2 month | 6.91 | 35.5 | 0.45 | 0.18 |    | 2 month | 4.87 | 43.9 | 0.26 | 0.06 |
| #5 | 0 month | 7.54 | 46.2 | 0.73 | 0.49 | #11 | 0 month | 5.67 | 51.0 | 0.61 | 0.22 |
|    | 1 month | 4.95 | 51.4 | 0.57 | 0.16 |    | 1 month | 4.71 | 45.3 | 0.38 | 0.08 |
|    | 2 month | 4.68 | 47.1 | 0.55 | 0.14 |    | 2 month | 4.97 | 40.2 | 0.33 | 0.38 |
| #6 | 0 month | 3.31 | 36.2 | 0.44 | 0.05 | #12 | 0 month | 5.83 | 53.4 | 0.67 | 0.52 |
|    | 1 month | 3.72 | 34.2 | 0.40 | 0.01 |    | 1 month | 5.13 | 48.9 | 0.34 | 1.07 |
|    | 2 month | 3.05 | 31.4 | 0.50 | 0.03 |    | 2 month | 5.55 | 39.7 | 0.33 | 1.19 |
| Healthy Subjects (n = 13) | | 2.52 (±0.53) | 19.0 (±2.0) | 0.19 (±0.02) | <0.01 | | | | | | |

Fig. 13

CALCULATION $$\frac{\text{Concentration ratio } (C_{D,I}/C_{IS}) \text{ in Unknowns}}{\text{Concentration ratio } (^0C_{D,I}/^0C_{IS}) \text{ in Standards}} = \frac{\text{Signal ratio } (A_{D,I}/A_{IS}) \text{ in Unknowns}}{\text{Signal ratio } (^0A_{D,I}/^0A_{IS}) \text{ in Standards}}$$

Desmosine (D):

$$C_D = C_{IS} \cdot (A_D/A_{IS}) \cdot (^0A_{IS}/^0C_{IS} \cdot {}^0C_D/^0A_D)$$

Isodesmosine (I):

$$C_I = C_{IS} \cdot (A_I/A_{IS}) \cdot (^0A_{IS}/^0C_{IS} \cdot {}^0C_I/^0A_I)$$

Where,
$C_{D, I, IS}$ : Concentrations (ng/mL) of D, I, or IS in Unknowns,
$A_{D, I, IS}$ : Signals (Chromatographic peak area) of D, I or IS in Unknowns,
$^0C_{D, I, IS}$ : Concentrations (ng/mL) of D, I, or IS in Standards,
$^0A_{D, I, IS}$ : Signals (Chromatographic peak area) of D, I or IS in Standards

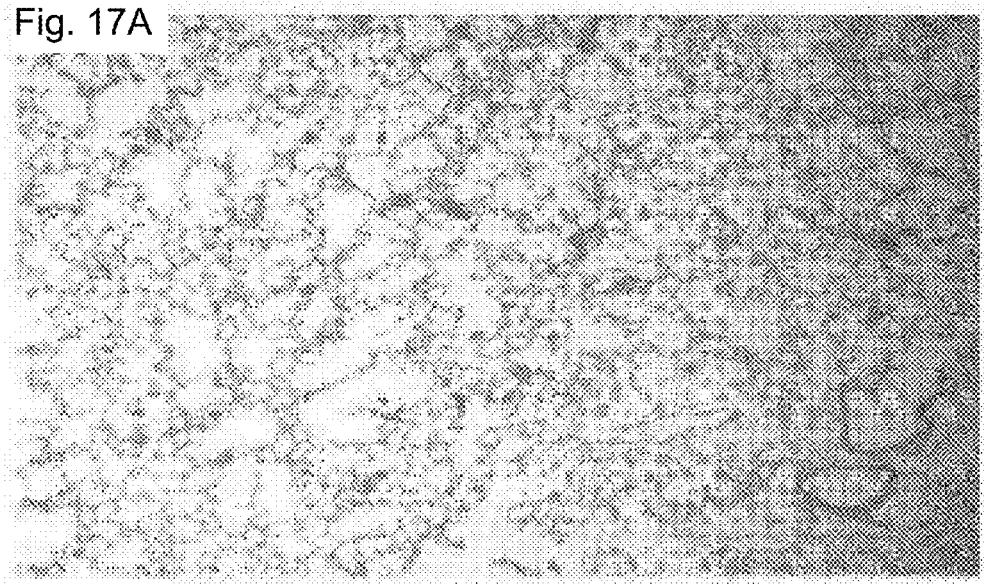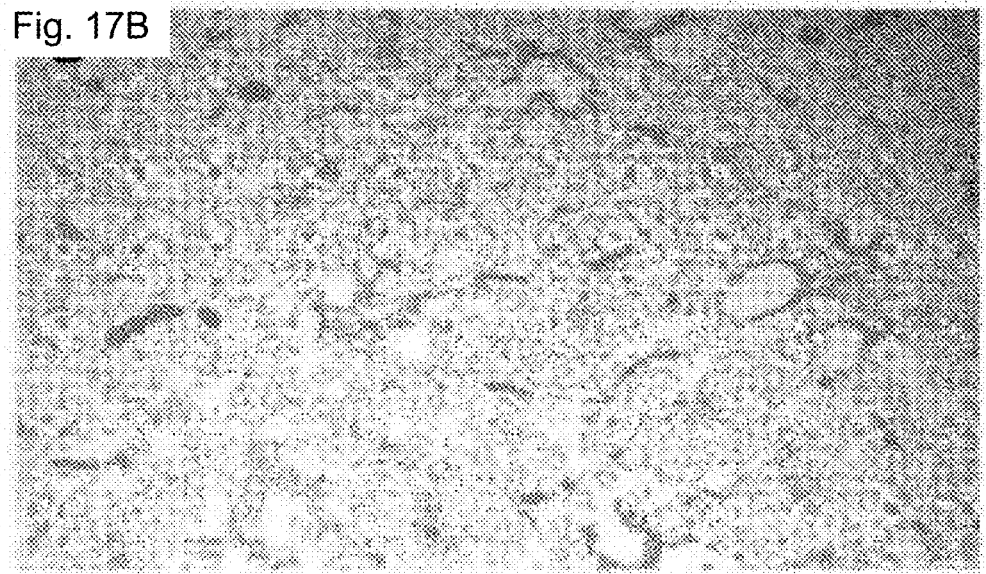

Fig. 20A
Isodesmosine (IDS)    Desmosine (DES)
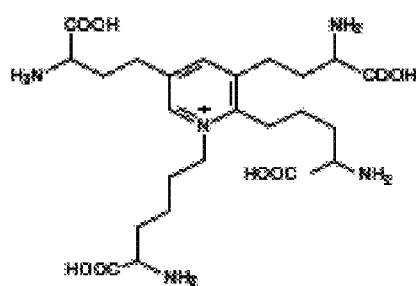
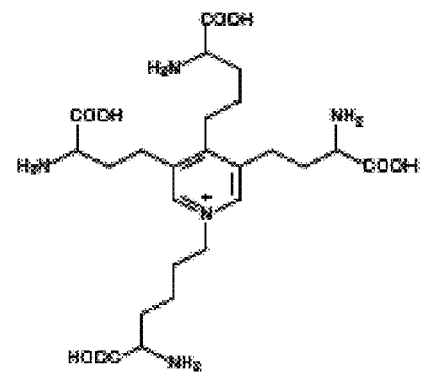
Acetylated Pyridinoline (IS)
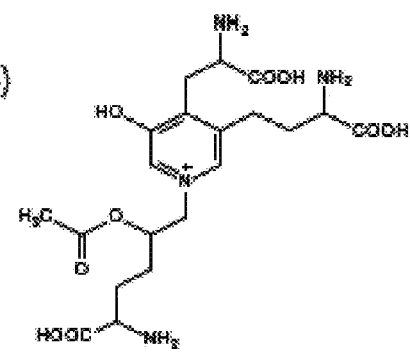

Non-exposed vs Exposed: P = 0.0223
Exposed vs Smokers   P = 0.1782
Non-exposed vs Smokers: P = 0.0075

Non-exposed vs Exposed:  P = 0.3047
Exposed vs Smokers:    P = 0.0734
Non-exposed vs Smokers: P = 0.0644

SEQUENCE LISTING

```
<160> NUMBER OF SEQ ID NOS: 75

<210> SEQ ID NO 1
<211> LENGTH: 786
<212> TYPE: PRT
<213> ORGANISM: Human

<400> SEQUENCE: 1

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
        130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205
```

-continued

```
Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Ala Gly Val Pro Gly Val Pro Gly Ala
            275                 280                 285

Ile Pro Gly Ile Gly Gly Ile Ala Gly Val Gly Thr Pro Ala Ala Ala
290                 295                 300

Ala Ala Ala Ala Ala Ala Ala Lys Ala Ala Lys Tyr Gly Ala Ala Ala
305                 310                 315                 320

Gly Leu Val Pro Gly Pro Gly Phe Gly Pro Gly Val Val Gly Val
                325                 330                 335

Pro Gly Ala Gly Val Pro Gly Val Gly Val Pro Gly Ala Gly Ile Pro
                340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Lys
            435                 440                 445

Ala Ala Lys Tyr Gly Ala Ala Gly Ala Gly Val Leu Gly Gly Leu Val
    450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Lys Ala Ala Ala Lys
            485                 490                 495

Ala Ala Gln Phe Gly Leu Val Pro Gly Val Gly Val Ala Pro Gly Val
            500                 505                 510

Gly Val Ala Pro Gly Val Gly Val Ala Pro Gly Val Gly Leu Ala Pro
            515                 520                 525

Gly Val Gly Val Ala Pro Gly Val Gly Val Ala Pro Gly Val Gly Val
            530                 535                 540

Ala Pro Gly Ile Gly Pro Gly Gly Val Ala Ala Ala Lys Ser Ala
545                 550                 555                 560

Ala Lys Val Ala Ala Lys Ala Gln Leu Arg Ala Ala Gly Leu Gly
                565                 570                 575

Ala Gly Ile Pro Gly Leu Gly Val Gly Val Gly Val Pro Gly Leu Gly
            580                 585                 590

Val Gly Ala Gly Val Pro Gly Leu Gly Val Gly Ala Gly Val Pro Gly
            595                 600                 605

Phe Gly Ala Gly Ala Asp Glu Gly Val Arg Arg Ser Leu Ser Pro Glu
610                 615                 620
```

```
Leu Arg Glu Gly Asp Pro Ser Ser Gln His Leu Pro Ser Thr Pro
625                 630                 635                 640

Ser Ser Pro Arg Val Pro Gly Ala Leu Ala Ala Lys Ala Ala Lys
            645                 650                 655

Tyr Gly Ala Ala Val Pro Gly Val Leu Gly Ala Gly Leu Ala Leu Gly
            660                 665                 670

Gly Val Gly Ile Pro Gly Val Val Gly Ala Gly Pro Ala Ala
        675                 680                 685

Ala Ala Ala Ala Lys Ala Ala Lys Ala Ala Gln Phe Gly Leu Val
            690                 695                 700

Gly Ala Ala Gly Leu Gly Gly Leu Gly Val Gly Leu Gly Val Pro
705                 710                 715                 720

Gly Val Gly Gly Leu Gly Gly Ile Pro Pro Ala Ala Ala Lys Ala
                725                 730                 735

Ala Lys Tyr Gly Ala Ala Gly Leu Gly Gly Val Leu Gly Ala Gly
            740                 745                 750

Gln Phe Pro Leu Gly Gly Val Ala Ala Arg Pro Gly Phe Gly Leu Ser
            755                 760                 765

Pro Ile Phe Pro Gly Gly Ala Cys Leu Gly Lys Ala Cys Gly Arg Lys
770                 775                 780

Arg Lys
785

<210> SEQ ID NO 2
<211> LENGTH: 5
<212> TYPE: PRT
<213> ORGANISM: Human

<400> SEQUENCE: 2

Leu Gly Val Gly Val
1               5

<210> SEQ ID NO 3
<211> LENGTH: 5
<212> TYPE: PRT
<213> ORGANISM: Human

<400> SEQUENCE: 3

Gly Gly Ile Pro Thr
1               5

<210> SEQ ID NO 4
<211> LENGTH: 6
<212> TYPE: PRT
<213> ORGANISM: Human

<400> SEQUENCE: 4

Ala Pro Gly Val Gly Val
1               5

<210> SEQ ID NO 5
<211> LENGTH: 4
<212> TYPE: PRT
<213> ORGANISM: Human

<400> SEQUENCE: 5

Gly Tyr Pro Ile
1

<210> SEQ ID NO 6
```

```
<211> LENGTH: 5
<212> TYPE: PRT
<213> ORGANISM: Human

<400> SEQUENCE: 6

Val Thr Phe Pro Gly
1               5

<210> SEQ ID NO 7
<211> LENGTH: 7
<212> TYPE: PRT
<213> ORGANISM: Human

<400> SEQUENCE: 7

Gly Ile Pro Gly Gly Val Val
1               5

<210> SEQ ID NO 8
<211> LENGTH: 11
<212> TYPE: PRT
<213> ORGANISM: Human

<400> SEQUENCE: 8

Ala Pro Gly Ile Gly Pro Gly Gly Val Ala Ala
1               5                   10

<210> SEQ ID NO 9
<211> LENGTH: 7
<212> TYPE: PRT
<213> ORGANISM: Human

<400> SEQUENCE: 9

Gly Val Pro Gly Leu Gly Val
1               5

<210> SEQ ID NO 10
<211> LENGTH: 7
<212> TYPE: PRT
<213> ORGANISM: Human

<400> SEQUENCE: 10

Gly Leu Gly Gly Leu Gly Val
1               5

<210> SEQ ID NO 11
<211> LENGTH: 7
<212> TYPE: PRT
<213> ORGANISM: Human

<400> SEQUENCE: 11

Gly Leu Gly Ala Phe Pro Ala
1               5

<210> SEQ ID NO 12
<211> LENGTH: 8
<212> TYPE: PRT
<213> ORGANISM: Human

<400> SEQUENCE: 12

Gly Gly Ile Pro Thr Tyr Gly Val
1               5

<210> SEQ ID NO 13
<211> LENGTH: 9
<212> TYPE: PRT
```

```
<213> ORGANISM: Human

<400> SEQUENCE: 13

Gly Ala Gly Val Pro Gly Leu Gly Val
1               5

<210> SEQ ID NO 14
<211> LENGTH: 8
<212> TYPE: PRT
<213> ORGANISM: Human

<400> SEQUENCE: 14

Ala Gly Leu Gly Gly Leu Gly Val
1               5

<210> SEQ ID NO 15
<211> LENGTH: 10
<212> TYPE: PRT
<213> ORGANISM: Human

<400> SEQUENCE: 15

Gly Ala Ala Gly Leu Gly Gly Leu Gly Val
1               5                   10

<210> SEQ ID NO 16
<211> LENGTH: 9
<212> TYPE: PRT
<213> ORGANISM: Human

<400> SEQUENCE: 16

Val Gly Val Leu Pro Gly Val Pro Thr
1               5

<210> SEQ ID NO 17
<211> LENGTH: 9
<212> TYPE: PRT
<213> ORGANISM: Human

<400> SEQUENCE: 17

Gly Val Gly Val Pro Gly Leu Gly Val
1               5

<210> SEQ ID NO 18
<211> LENGTH: 11
<212> TYPE: PRT
<213> ORGANISM: Human

<400> SEQUENCE: 18

Ala Ala Arg Pro Gly Phe Gly Leu Ser Pro Ile
1               5                   10

<210> SEQ ID NO 19
<211> LENGTH: 11
<212> TYPE: PRT
<213> ORGANISM: Human

<400> SEQUENCE: 19

Gly Leu Gly Ala Gly Leu Gly Ala Phe Pro Ala
1               5                   10

<210> SEQ ID NO 20
<211> LENGTH: 10
<212> TYPE: PRT
<213> ORGANISM: Human
```

```
<400> SEQUENCE: 20

Gly Ala Gly Gly Phe Pro Gly Phe Gly Val
1               5                   10

<210> SEQ ID NO 21
<211> LENGTH: 14
<212> TYPE: PRT
<213> ORGANISM: Human

<400> SEQUENCE: 21

Gly Leu Val Pro Gly Gly Pro Gly Phe Gly Pro Gly Val Val
1               5                   10

<210> SEQ ID NO 22
<211> LENGTH: 19
<212> TYPE: PRT
<213> ORGANISM: Human

<400> SEQUENCE: 22

Gly Val Pro Gly Ala Gly Val Pro Gly Val Gly Val Pro Gly Ala Gly
1               5                   10                  15

Ile Pro Val

<210> SEQ ID NO 23
<211> LENGTH: 12
<212> TYPE: PRT
<213> ORGANISM: Human

<400> SEQUENCE: 23

Phe Pro Gly Val Gly Val Leu Pro Gly Val Pro Thr
1               5                   10

<210> SEQ ID NO 24
<211> LENGTH: 18
<212> TYPE: PRT
<213> ORGANISM: Human

<400> SEQUENCE: 24

Gly Val Gly Val Pro Gly Leu Gly Val Gly Ala Gly Val Pro Gly Leu
1               5                   10                  15

Gly Val

<210> SEQ ID NO 25
<211> LENGTH: 17
<212> TYPE: PRT
<213> ORGANISM: Human

<400> SEQUENCE: 25

Gly Leu Gly Gly Val Leu Gly Gly Ala Gly Gln Phe Pro Leu Gly Gly
1               5                   10                  15

Val

<210> SEQ ID NO 26
<211> LENGTH: 6
<212> TYPE: PRT
<213> ORGANISM: Human

<400> SEQUENCE: 26

Val Ala Pro Gly Val Gly
1               5

<210> SEQ ID NO 27
```

```
<211> LENGTH: 7
<212> TYPE: PRT
<213> ORGANISM: Human

<400> SEQUENCE: 27

Val Gly Ala Gly Val Pro Gly
1               5

<210> SEQ ID NO 28
<211> LENGTH: 6
<212> TYPE: PRT
<213> ORGANISM: Human

<400> SEQUENCE: 28

Leu Ala Pro Gly Val Gly
1               5

<210> SEQ ID NO 29
<211> LENGTH: 7
<212> TYPE: PRT
<213> ORGANISM: Human

<400> SEQUENCE: 29

Leu Val Pro Gly Gly Pro Gly
1               5

<210> SEQ ID NO 30
<211> LENGTH: 8
<212> TYPE: PRT
<213> ORGANISM: Human

<400> SEQUENCE: 30

Val Gly Val Ala Pro Gly Val Gly
1               5

<210> SEQ ID NO 31
<211> LENGTH: 7
<212> TYPE: PRT
<213> ORGANISM: Human

<400> SEQUENCE: 31

Val Gly Val Gly Val Pro Gly
1               5

<210> SEQ ID NO 32
<211> LENGTH: 6
<212> TYPE: PRT
<213> ORGANISM: Human

<400> SEQUENCE: 32

Leu Val Pro Gly Val Gly
1               5

<210> SEQ ID NO 33
<211> LENGTH: 7
<212> TYPE: PRT
<213> ORGANISM: Human

<400> SEQUENCE: 33

Leu Gly Ala Gly Ile Pro Gly
1               5

<210> SEQ ID NO 34
<211> LENGTH: 5
<212> TYPE: PRT
```

<213> ORGANISM: Human

<400> SEQUENCE: 34

Phe Pro Gly Val Gly
1               5

<210> SEQ ID NO 35
<211> LENGTH: 9
<212> TYPE: PRT
<213> ORGANISM: Human

<400> SEQUENCE: 35

Leu Gly Val Gly Ala Gly Val Pro Gly
1               5

<210> SEQ ID NO 36
<211> LENGTH: 6
<212> TYPE: PRT
<213> ORGANISM: Human

<400> SEQUENCE: 36

Val Thr Phe Pro Gly Ala
1               5

<210> SEQ ID NO 37
<211> LENGTH: 6
<212> TYPE: PRT
<213> ORGANISM: Human

<400> SEQUENCE: 37

Leu Gly Ala Phe Pro Ala
1               5

<210> SEQ ID NO 38
<211> LENGTH: 11
<212> TYPE: PRT
<213> ORGANISM: Human

<400> SEQUENCE: 38

Val Tyr Pro Gly Gly Val Leu Pro Gly Ala Arg
1               5                   10

<210> SEQ ID NO 39
<211> LENGTH: 9
<212> TYPE: PRT
<213> ORGANISM: Human

<400> SEQUENCE: 39

Val Tyr Pro Gly Gly Val Leu Pro Gly
1               5

<210> SEQ ID NO 40
<211> LENGTH: 10
<212> TYPE: PRT
<213> ORGANISM: Human

<400> SEQUENCE: 40

Phe Gly Val Gly Val Gly Gly Ile Pro Gly
1               5                   10

<210> SEQ ID NO 41
<211> LENGTH: 11
<212> TYPE: PRT
<213> ORGANISM: Human

```
<400> SEQUENCE: 41

Leu Gly Val Gly Val Gly Val Pro Gly Leu Gly
1               5                   10

<210> SEQ ID NO 42
<211> LENGTH: 6
<212> TYPE: PRT
<213> ORGANISM: Human

<400> SEQUENCE: 42

Val Gly Val Ala Pro Gly
1               5

<210> SEQ ID NO 43
<211> LENGTH: 5
<212> TYPE: PRT
<213> ORGANISM: Human

<400> SEQUENCE: 43

Val Gly Leu Pro Gly
1               5

<210> SEQ ID NO 44
<211> LENGTH: 5
<212> TYPE: PRT
<213> ORGANISM: Human

<400> SEQUENCE: 44

Ala Gly Ile Pro Val
1               5

<210> SEQ ID NO 45
<211> LENGTH: 4
<212> TYPE: PRT
<213> ORGANISM: Human

<400> SEQUENCE: 45

Gly Tyr Pro Ile
1

<210> SEQ ID NO 46
<211> LENGTH: 4
<212> TYPE: PRT
<213> ORGANISM: Human

<400> SEQUENCE: 46

Val Gly Pro Phe
1

<210> SEQ ID NO 47
<211> LENGTH: 10
<212> TYPE: PRT
<213> ORGANISM: Human

<400> SEQUENCE: 47

Val Gly Pro Phe Gly Gly Pro Gln Pro Gly
1               5                   10

<210> SEQ ID NO 48
<211> LENGTH: 5
<212> TYPE: PRT
<213> ORGANISM: Human

<400> SEQUENCE: 48
```

Gln Phe Gly Leu Val
1               5

<210> SEQ ID NO 49
<211> LENGTH: 9
<212> TYPE: PRT
<213> ORGANISM: Human

<400> SEQUENCE: 49

Gly Pro Gly Phe Gly Pro Gly Val Val
1               5

<210> SEQ ID NO 50
<211> LENGTH: 6
<212> TYPE: PRT
<213> ORGANISM: Human

<400> SEQUENCE: 50

Phe Gly Leu Ser Pro Ile
1               5

<210> SEQ ID NO 51
<211> LENGTH: 12
<212> TYPE: PRT
<213> ORGANISM: Human

<400> SEQUENCE: 51

Gly Leu Val Pro Gly Gly Pro Gly Phe Gly Pro Gly
1               5                   10

<210> SEQ ID NO 52
<211> LENGTH: 8
<212> TYPE: PRT
<213> ORGANISM: Human

<400> SEQUENCE: 52

Gly Gly Phe Pro Gly Phe Gly Val
1               5

<210> SEQ ID NO 53
<211> LENGTH: 14
<212> TYPE: PRT
<213> ORGANISM: Human

<400> SEQUENCE: 53

Gly Leu Val Pro Gly Gly Pro Gly Phe Gly Pro Gly Val Val
1               5                   10

<210> SEQ ID NO 54
<211> LENGTH: 9
<212> TYPE: PRT
<213> ORGANISM: Bovine

<400> SEQUENCE: 54

Gly Gly Val Gly Asp Leu Gly Gly Ala
1               5

<210> SEQ ID NO 55
<211> LENGTH: 6
<212> TYPE: PRT
<213> ORGANISM: Bovine

<400> SEQUENCE: 55

Val Gly Val Ala Pro Gly
1               5

<210> SEQ ID NO 56
<211> LENGTH: 5
<212> TYPE: PRT
<213> ORGANISM: Bovine

<400> SEQUENCE: 56

Val Gly Leu Pro Gly
1               5

<210> SEQ ID NO 57
<211> LENGTH: 6
<212> TYPE: PRT
<213> ORGANISM: Bovine

<400> SEQUENCE: 57

Gly Gly Leu Val Pro Gly
1               5

<210> SEQ ID NO 58
<211> LENGTH: 6
<212> TYPE: PRT
<213> ORGANISM: Bovine

<400> SEQUENCE: 58

Ala Gly Leu Gly Gly Val
1               5

<210> SEQ ID NO 59
<211> LENGTH: 4
<212> TYPE: PRT
<213> ORGANISM: Bovine

<400> SEQUENCE: 59

Gly Tyr Pro Ile
1

<210> SEQ ID NO 60
<211> LENGTH: 4
<212> TYPE: PRT
<213> ORGANISM: Bovine

<400> SEQUENCE: 60

Val Gly Pro Phe
1

<210> SEQ ID NO 61
<211> LENGTH: 8
<212> TYPE: PRT
<213> ORGANISM: Bovine

<400> SEQUENCE: 61

Pro Gly Val Gly Val Val Pro Gly
1               5

<210> SEQ ID NO 62
<211> LENGTH: 6
<212> TYPE: PRT
<213> ORGANISM: Bovine

<400> SEQUENCE: 62

Pro Gly Leu Gly Val Gly
1               5

```
<210> SEQ ID NO 63
<211> LENGTH: 9
<212> TYPE: PRT
<213> ORGANISM: Bovine

<400> SEQUENCE: 63

Gly Gly Gln Gln Pro Gly Val Pro Leu
1               5

<210> SEQ ID NO 64
<211> LENGTH: 5
<212> TYPE: PRT
<213> ORGANISM: Bovine

<400> SEQUENCE: 64

Phe Pro Gly Ile Gly
1               5

<210> SEQ ID NO 65
<211> LENGTH: 4
<212> TYPE: PRT
<213> ORGANISM: Bovine

<400> SEQUENCE: 65

Phe Pro Gly Ile
1

<210> SEQ ID NO 66
<211> LENGTH: 6
<212> TYPE: PRT
<213> ORGANISM: Bovine

<400> SEQUENCE: 66

Gly Gly Ile Pro Thr Phe
1               5

<210> SEQ ID NO 67
<211> LENGTH: 9
<212> TYPE: PRT
<213> ORGANISM: Bovine

<400> SEQUENCE: 67

Gly Phe Pro Gly Ile Gly Asp Ala Ala
1               5

<210> SEQ ID NO 68
<211> LENGTH: 6
<212> TYPE: PRT
<213> ORGANISM: Bovine

<400> SEQUENCE: 68

Gly Gln Pro Phe Pro Ile
1               5

<210> SEQ ID NO 69
<211> LENGTH: 12
<212> TYPE: PRT
<213> ORGANISM: Bovine

<400> SEQUENCE: 69

Val Gly Pro Phe Gly Gly Gln Gln Pro Gly Val Pro
1               5                   10

<210> SEQ ID NO 70
<211> LENGTH: 10
```

```
<212> TYPE: PRT
<213> ORGANISM: Bovine

<400> SEQUENCE: 70

Phe Pro Gly Ala Gly Leu Gly Gly Leu Gly
1               5                   10

<210> SEQ ID NO 71
<211> LENGTH: 9
<212> TYPE: PRT
<213> ORGANISM: Bovine

<400> SEQUENCE: 71

Phe Pro Gly Ile Gly Val Leu Pro Gly
1               5

<210> SEQ ID NO 72
<211> LENGTH: 13
<212> TYPE: PRT
<213> ORGANISM: Bovine

<400> SEQUENCE: 72

Val Gly Pro Phe Gly Gly Gln Gln Pro Gly Val Pro Leu
1               5                   10

<210> SEQ ID NO 73
<211> LENGTH: 8
<212> TYPE: PRT
<213> ORGANISM: Bovine

<400> SEQUENCE: 73

Gly Val Phe Phe Pro Gly Ala Gly
1               5

<210> SEQ ID NO 74
<211> LENGTH: 6
<212> TYPE: PRT
<213> ORGANISM: Bovine

<400> SEQUENCE: 74

Val Phe Phe Pro Gly Ala
1               5

<210> SEQ ID NO 75
<211> LENGTH: 6
<212> TYPE: PRT
<213> ORGANISM: Bovine

<400> SEQUENCE: 75

Val Gly Pro Gly Leu Gly
1               5
```

CELL CULTURE MODELS FOR VALIDATING CANDIDATE COMPOUNDS FOR USE IN TREATING COPD AND OTHER DISEASES

CROSS-REFERENCE TO RELATED APPLICATIONS

The present application is a divisional application of U.S. patent application Ser. No. 13/836,332, filed Mar. 15, 2013, now U.S. Pat. No. 9,068,942, issued Jun. 30, 2015, which is a continuation of U.S. patent application Ser. No. 13/575,346, now abandoned, which is the national stage of International Application No. PCT/US2011/022619, filed Jan. 26, 2011, which claims benefit to U.S. provisional application Ser. No. 61/336,804 filed Jan. 26, 2010, the entire contents of which are incorporated by reference.

INCORPORATION BY REFERENCE OF SEQUENCE LISTING

This application contains references to amino acids and/or nucleic acid sequences that have been filed concurrently herewith as sequence listing text file COPD_ST25.txt, file size 16.7 KB, created on May 13, 2015. The aforementioned sequence listing is hereby incorporated by reference in its entirety pursuant to 37 C.F.R. §1.52(e)(5).

FIELD OF THE INVENTION

The present invention relates to the field of elastin fiber injuries and, more particularly, to methods of diagnosing, monitoring, and treating elastin fiber injuries. Still further, the present invention relates to methods of validating candidate compounds for use in treating elastin fiber injuries, such as those injuries caused by chronic obstructive pulmonary disease (COPD), chronic bronchitis, emphysema, refractory asthma, and other related diseases.

BACKGROUND OF THE INVENTION

Lung elastin degradation occurs with the development of pulmonary emphysema in patients with COPD related to smoking or alpha-1 antitrypsin deficiency. COPD a lengthy, chronic, progressive disease, is debilitating and often non-reversible. COPD is a growing and costly problem. COPD currently affects over 18 million Americans and is the fourth leading cause of death in the US. According to the World Health Organization in 2007, 210 million people worldwide have suffered from COPD and 3 million of those died in 2005 alone[68]. According to the current trends, WHO estimates that it will become the third leading cause of death worldwide by the year 2030.

Although a number of different mechanisms may be responsible for the loss of alveoli in pulmonary emphysema, damage to elastic fibers is a significant factor in the pathogenesis of this disease[1,2]. These fibers are responsible for the mechanical recoil that facilitates the expiration of air from the lungs, and their breakdown can lead to alveolar distention and rupture.

Elastin fibers are part of the extracellular matrix and are an essential structural component of lung, skin, and blood vessels. Desmosine (D) and Isodesmosine (I) are two unique pyridinium amino acids that serve as crosslinking molecules binding the polymeric chains of amino acids into the 3D network of elastin[33-35]. The degradation of elastin-containing tissues that occurs in several widely prevalent diseases, such as atherosclerosis, aortic aneurysms, cystic fibrosis and COPD which includes pulmonary emphysema etc., have been associated with increased excretion in the urine of peptides containing these two pyridinium compounds[36-44]. As noted above, in lung, elastin degradation occurs with the development of COPD related to smoking or related to α1-antitrypsin deficiency (AATD)[45,46].

Due to the importance of elastic fiber injury in pulmonary emphysema, a number of therapeutic approaches have focused on protecting this extracellular matrix component from degradation by elastases and other injurious agents[3,4]. However, determining the effectiveness of such treatment is often difficult because of the lack of sensitive, real-time indicators of successful therapeutic intervention. Both pulmonary function tests and high-resolution computerized tomography (HRCT) require prolonged time intervals to assess the potential benefits of a therapy, while more sensitive markers such as proinflammatory cytokines lack the necessary specificity to determine efficacy[5-9]. One possible solution to this problem is measurement of elastic fiber breakdown products themselves.

Desmosine and isodesmosine, the crosslinking amino acids present only in elastin in the human, offer the prospect of assessing elastin degradation in disease by their measurement in certain body fluids. Thus far, D and I have been measured in urine of patients with COPD and found to be statistically significantly elevated above normal controls. One study demonstrated the daily variability of excretion of desmosine and isodesmosine and did not show a statistically significantly elevated excretion of these amino acids in patients in 24-hour collections. In this same study, statistically significantly increased excretion of desmosine and isodesmosine was found in patients with cystic fibrosis.

Various techniques including RIA[47,48], HPLC[49-51], and capillary zone electrophoresis[52,53] have been utilized for the analysis of urinary D and I. Measurements in subjects with COPD show increased levels of D and I in acid hydrolyzed sputum and plasma, along with elevated free D and I in urine without acid hydrolysis[11,54].

Recent advances in detecting the elastin-specific amino acid crosslinks desmosine and isodesmosine have greatly increased the sensitivity and specificity of this test procedure[10-14]. Levels of D and I in urine and plasma have been shown to correlate with physiological and radiological measures of COPD[12].

Peptides of elastin have been measured in plasma by radioimmunoassay (RIA) and found to be elevated in patients with COPD. Because of variability of the specificity of antibodies to elastin peptides in such RIAs, however, quantitation of such peptides has varied among various studies. Advances have been made in the ability to measure D and I in certain complex biological samples using mass spectrometry. For example, the LC/MS analysis which provides increased sensitivity and specificity may be an important method for biomarker analysis of elastin degradation in disease[55].

Three LC/MSMS analyses of D and I have been reported[56-58]. These studies have been limited to the analysis of D and I content in urine or mouse lung hydrolysates. As we have shown in the study of D and I in COPD[11,54] and a study on the effect of Tiotropium therapy on D and I levels in COPD[10], it is recommended that D and I levels be evaluated in other body fluids as well; such as sputum, plasma, or bronco alveolar lavage fluid. An accurate and reproducible quantification of D and I in several body fluids may be more useful to characterize elastin degradation in disease and to follow the course of disease and therapies[59].

In addition, two recent FDA workshops sponsored by the COPD Foundation held in May, 2009 and January, 2010 have called for standardization of the analysis to provide practical clinical biomarkers for COPD.

Active smoking is the most important modifiable risk factor for COPD[69]. In comparison to previous years, overall less people smoke now, however, there has been a disturbing increase in active smokers in the under-30 age group[68]. Once active smoking was established as having detrimental health effects on lung disease, the focus turned to the possible adverse effects of passive smoking—the atmospheric exposure to second hand smoke.

Second Hand Smoke exposure (SHS) has been implicated as a risk factor in many diseases including asthma, bronchitis, and coronary artery disease[70]. As a result, there is a worldwide campaign to eliminate passive smoking from the environment[71]. Second hand smoke increases the risk of heart disease in adults[72] and has been shown to increase the inflammatory state[73]. Flouris et al. demonstrated an increase in inflammatory cytokines in individuals who had never smoked who were exposed to only one hour of second hand smoke, and these cytokines remained elevated for three hours after the exposure ceased[70]. In the Attica study, inflammatory cytokines were elevated from chronic exposure to second hand smoke for extended periods, and the levels were similar to these of the active smokers[74].

Given the deleterious effects of passive smoking on overall health, it is reasonable to consider its detrimental effects on lung parenchyma itself. Studies of subjects exposed heavily to second hand smoke, i.e. bar workers, flight attendants, have shown an increase in lung cancer, COPD, bronchitis, and asthma exacerbations[75]. In the same studies, subjective health improved within one month of a clean air environment and objective improvement was seen within two months. There are studies demonstrating the effect of second hand smoke exposure on biomarkers of inflammation in patients with cardiovascular as well as pulmonary disease[76-78]. However thus far, no studies have evaluated the effect of second hand smoke exposure on tissue matrix proteins.

In view of the foregoing, there is a need for methods of accurately detecting and measuring elastin components, such as desmosine, isodesmosine or combinations thereof, for the purpose of diagnosing and/or treating COPD, chronic bronchitis, emphysema, refractory asthma, and other related diseases and/or monitoring patients with such diseases and/or who are exposed to, e.g., SHS. Similarly, there is a need for methods of validating whether a candidate compound is effective to treat, prevent, or ameliorate the effects of a disease characterized by elastic fiber injury.

SUMMARY OF THE INVENTION

We have developed a more specific and sensitive LC/MS analysis, which can measure D and I in plasma, urine, and for the first time in sputum. According to one preferred embodiment of the present invention, methods are provided for validating whether a candidate compound is effective to treat, prevent, or ameliorate the effects of a disease characterized by elastic fiber injury. In such embodiments, the methods comprise determining if the candidate compound decreases the degradation of elastic fiber in a patient administered the candidate compound by measuring, using mass spectrometry, a marker of elastic fiber degradation in a sample of a body fluid or a tissue of the patient. The invention provides that a decrease in the presence of the marker compared to a control validates that the candidate compound is effective to treat, prevent, or ameliorate the disease.

According to another preferred embodiment of the present invention, methods are provided for validating whether a candidate compound is effective to treat, prevent, or ameliorate the effects of COPD. Such methods comprise determining if the candidate compound decreases the degradation of elastin in a patient administered the candidate compound by measuring, using mass spectrometry, the amount of desmosine, isodesmosine, or combinations thereof in a sample of a body fluid or tissue of the patient. The invention provides that a decrease in the presence of desmosine and/or isodesmosine compared to a control validates that the candidate compound is effective to treat, prevent, or ameliorate the disease. In certain preferred embodiments, the body fluid may comprise plasma, urine, sputum, or combinations thereof.

According to additional embodiments of the present invention, methods are provided for identifying candidate compounds that are effective to treat, prevent, or ameliorate the effects of a disease characterized by elastic fiber injury. Such methods of the invention comprise (a) administering a candidate compound to a cell culture model of the disease; (b) measuring, by mass spectrometry, the amount of a marker of elastic fiber injury in the cell culture administered the candidate compound; and (c) determining whether the amount of the marker produced by the cell culture administered the candidate compound is different compared to a control cell culture absent the candidate compound. Non-limiting examples of appropriate markers include desmosine, isodesmosine, or combinations thereof. The invention provides that a decrease in the amount of such marker(s) produced by the cell culture administered the candidate compound compared to the control cell culture identifies the candidate compound as effective to treat, prevent, or ameliorate the effects of the disease.

According to one preferred embodiment of the present invention, methods are provided for validating whether a candidate compound is effective to treat, prevent, or ameliorate the effects of a disease characterized by elastic fiber injury. In such embodiments, the methods comprise determining if the candidate compound decreases the degradation of elastic fiber in a patient administered the candidate compound by measuring, using mass spectrometry employing an internal standard, a marker of elastic fiber degradation in a sample of a body fluid or a tissue of the patient. The invention provides that a decrease in the presence of the marker compared to a control validates that the candidate compound is effective to treat, prevent, or ameliorate the disease. In preferred methods, tandem mass spectrometry is used.

According to another preferred embodiment of the present invention, methods are provided for validating whether a candidate compound is effective to treat, prevent, or ameliorate the effects of COPD. Such methods comprise determining if the candidate compound decreases the degradation of elastin in a patient administered the candidate compound by measuring, using mass spectrometry employing an internal standard, the amount of desmosine, isodesmosine, or combinations thereof in a sample of a body fluid or tissue of the patient. The invention provides that a decrease in the presence of desmosine and/or isodesmosine compared to a control validates that the candidate compound is effective to treat, prevent, or ameliorate the disease. In certain preferred embodiments, the body fluid may comprise plasma, urine, sputum, or combinations thereof. In preferred methods, tandem mass spectrometry is used.

According to additional embodiments of the present invention, methods are provided for identifying candidate compounds that are effective to treat, prevent, or ameliorate the effects of a disease characterized by elastic fiber injury. Such methods of the invention comprise (a) administering a candidate compound to a cell culture model of the disease; (b) measuring, by mass spectrometry employing an internal standard, the amount of a marker of elastic fiber injury in the cell culture administered the candidate compound; and (c) determining whether the amount of the marker produced by the cell culture administered the candidate compound is different compared to a control cell culture absent the candidate compound. Non-limiting examples of appropriate markers include desmosine, isodesmosine, or combinations thereof. The invention provides that a decrease in the amount of such marker(s) produced by the cell culture administered the candidate compound compared to the control cell culture identifies the candidate compound as effective to treat, prevent, or ameliorate the effects of the disease. In preferred methods, tandem mass spectrometry is used.

BRIEF DESCRIPTION OF THE FIGURES

FIG. 5: A table summarizing the experimental results described herein relative to COPD patients having normal alpha 1-antitrypsin.

FIG. 6: A table summarizing the experimental results described herein relative to patients having alpha 1-antitrypsin related-COPD.

FIG. 7 demonstrates increasing specificities of three analytical methods. The HPLC/UV method measures all molecular species that have the same UV absorption (286 mμ) with D and I. The SIM method identifies and quantifies all molecules that have the same molecular weight (526) with D and I. The RIM method identifies and quantifies the ion fragments (481 and 397) that are only derived from D and I.

FIG. 9: A table summarizing the experimental results described herein relative to patients treated with Tiotropium.

FIG. 13: Shown in FIG. 13 are the formulas used to determine the concentration of D and of I in the samples. In the calculations, the ratio of the analyte response to the internal standard response is taken into account.

FIG. 17A: Lungs exposed to smoke for 3 months without HA treatment showed a moderate degree of airspace enlargement.

FIG. 17B: Lungs exposed to smoke for 3 months and treated with HA for 2 months showed only minimal airspace enlargement. Original magnification of both figures: 40× (hematoxylin and eosin).

FIG. 20A: Molecular structures of Desmosine (DES), Isodesmosine (IDS), and Acetylated Pyridinoline (IS).

FIG. 22A: The level (mg/g creatinine) of urinary DES+IDS in COPD patients (n=11) and healthy controls (n=9). (1) free DES+IDS of COPD (median 3.69) versus controls (median 2.39), p=0.0098; (2) total DES+IDS of COPD (median 11.50) versus controls (median 9.67), p=0.1147; (3) ratio of free DES+IDS to total DES+IDS of COPD (median 39.5) versus controls (median 24.3), p=<0.0001. FIG. 22B: The levels of plasma total DES+IDS in COPD (n=14) and healthy controls (n=4). (1) total DES+IDS (ng/ml) of COPD (median 0.40) versus controls (median 0.21), p<0.0001 (2) total DES+IDS (ng/g protein) of COPD (median 7.37) versus controls (median 3.76), p=0.0001. FIG. 22C: The levels of sputum of total DES+IDS in COPD (n=8) and healthy controls (n=5). (1) total DES+IDS (ng/ml) of COPD (median 0.22) versus controls (below LOD limit 0.04 ng/ml), p=0.0093; (2) total DES+IDS (ng/g protein) of COPD (median 56.94) versus controls (below LOD 14.29 ng/g protein), p=0.0025.

DETAILED DESCRIPTION OF THE INVENTION

Figure 1A:
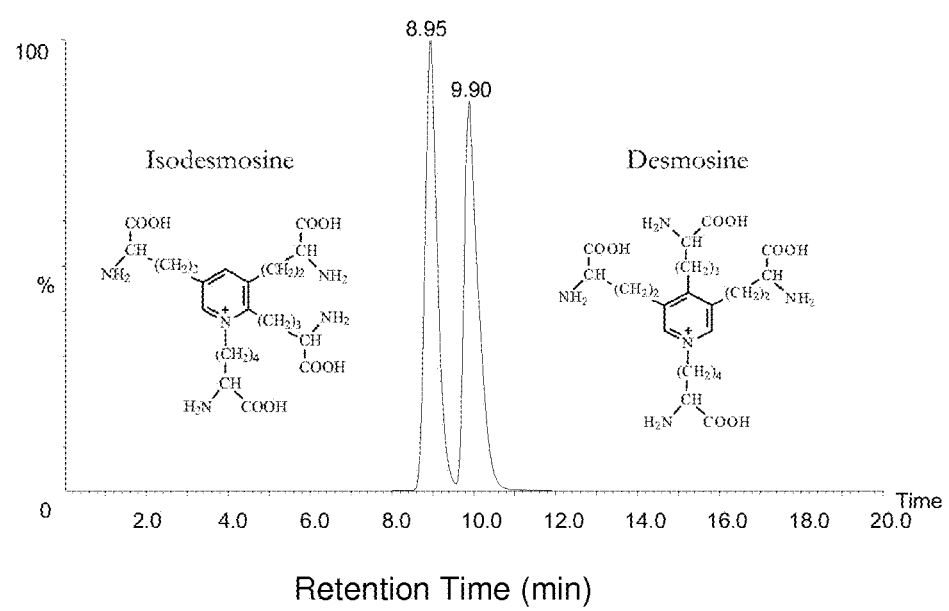
FIG. 1A: HPLC separation of D and I was achieved by an Atlantis dC18 column (2.1×150 mm, 3 μm) (Waters). The mobile phase A is aqueous 7 mM heptafluorobutyric acid and 5 mM ammonium acetate, and the mobile phase B is a solution of 7 mM heptafluorobutyric acid and 5 mM ammonium acetate in a acetonitrile/water (8:2). HPLC chromatography was performed using a 12 minute linear gradient flow of the mobile phase A from 100% to 88% and mobile phase B from 0% to 12% at a flow rate of 0.3 ml/min. The temperature of the HPLC column is set at 30° C. Under these chromatographic conditions desmosine and isodesmosine were detected at 8.95 minutes and 9.90 minutes, respectively. The mass spectrometer was operated in the positive ion mode with the following spectrometric parameters: capillary voltage 3.20 kV, sample cone voltage 55 V, ion energy 0.5 eV, amplifier voltage 650 V, and temperatures of the desolvation and the source at 400° C. and 120° C., respectively.
Figure 1B:
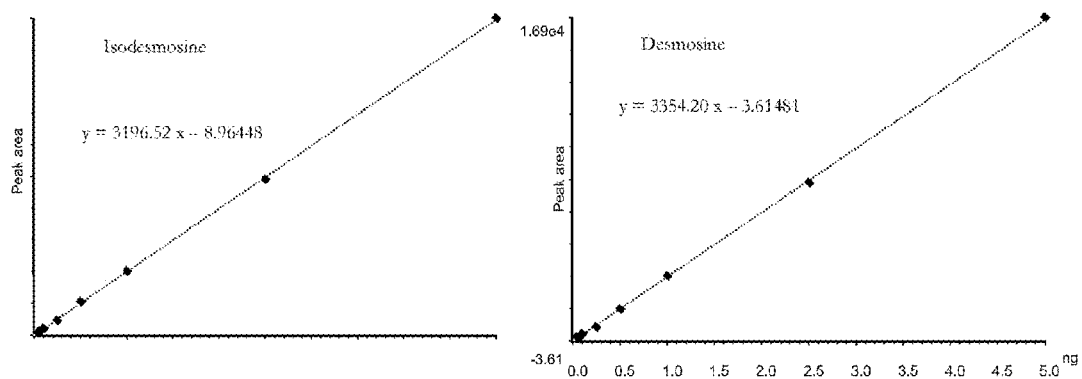
FIG. 1B: Quantification of D and I was achieved by a single ion record (SIR) of D and I molecular ions, both at m/z 526.25 (two isomeric molecules), produced from the LC/MS analysis. Peak areas of the SIR obtained by D and I standards provided good linearity between 0.05 ng to 5 ng.

According to one preferred embodiment of the present invention, methods are provided for validating whether a candidate compound is effective to treat, prevent, or ameliorate the effects of a disease characterized by elastic fiber injury, such as elastin degradation. In such embodiments, the methods comprise determining if the candidate compound decreases the degradation of elastic fiber in a patient administered the candidate compound by measuring, using mass spectrometry, a marker of elastic fiber degradation in a sample of a body fluid or a tissue of the patient. The invention provides that a decrease in the presence of the marker compared to a control validates that the candidate compound is effective to treat, prevent, or ameliorate the disease.

The foregoing methods may be used to validate whether a candidate compound is effective to treat, prevent, or ameliorate the effects of chronic obstructive pulmonary disease (COPD), chronic bronchitis, emphysema, and/or refractory asthma. The marker of elastic fiber degradation that is measured using mass spectrometry is preferably desmosine, isodesmosine, or combinations thereof. In such embodiments, the marker(s), such as desmosine, isodesmosine, or combinations thereof, are preferably detected and measured within a patient's urine, plasma, and/or sputum.

In certain preferred embodiments of the invention, desmosine, isodesmosine, or combinations thereof are measured in plasma. In certain alternative embodiments, total free desmosine, isodesmosine, or combinations thereof are measured in urine. The methods of the present invention may be employed to test the therapeutic value, or effectiveness, of a variety of different candidate compounds. Non-limiting examples of such compounds include hyaluronic acid, polysaccharides, carbohydrates, small molecules, and RNAi molecules, including siRNAs, shRNAs, and others.

According to additional embodiments of the present invention, methods are provided for identifying candidate compounds that are effective to treat, prevent, or ameliorate the effects of a disease characterized by elastic fiber injury. Such methods of the invention comprise (a) administering a candidate compound to an in vivo or in vitro model of the disease, e.g., a cell culture; (b) measuring, by mass spectrometry, the amount of a marker of elastic fiber injury in the cell culture administered the candidate compound; and (c) determining whether the amount of the marker produced by e.g., the cell culture administered the candidate compound is different compared to e.g., a control cell culture absent the candidate compound. Non-limiting examples of appropriate markers include desmosine, isodesmosine, or combinations thereof. The invention provides that a decrease in the amount of such marker(s) produced by e.g., the cell culture administered the candidate compound compared to e.g., the control cell culture identifies the candidate compound as effective to treat, prevent, or ameliorate the effects of the disease.

Such methods may be used for identifying candidate compounds that are effective to treat, prevent, modulate and/or ameliorate the effects of elastin degradation and diseases associated therewith, such as COPD, chronic bronchitis, emphysema, and/or refractory asthma. Similar to the other embodiments discussed herein, the marker that is measured by mass spectrometry is preferably selected from desmosine, isodesmosine, or combinations thereof. Still further, similar to the other embodiments discussed herein, such methods may be employed to test the therapeutic value, or effectiveness, of a variety of different candidate compounds, including hyaluronic acid, polysaccharides, carbohydrates, small molecules, and RNAi molecules, such as siRNAs, shRNAs, and others.

It is noted that, throughout the instant disclosure, desmosine is frequently abbreviated as "D" or "DES," and isodesmosine is frequently abbreviated as "I" or "IDS." Similarly, desmosine and isodesmosine may be collectively abbreviated herein as "D and I," "D/I," "DID," "DES/IDS," or "DES and IDS."

"Tandem mass spectrometry" as used herein refers to techniques in which a sample is analyzed two or more times by mass spectrometry. Typically, the sample is analyzed twice, which is referred to herein as MS/MS or MSMS, but it may be analyzed three or more times. In tandem mass spectrometry, the same mass spectroscope may be used two or more times for a given sample, or separate mass spectroscopes may be used. In the latter case, preferably two different mass spectroscopes connected in series are used. The first mass spectrometer sorts and weighs the sample, then the sample enters a collision cell which breaks the sample into fragments, and the second mass spectrometer sorts and weighs the resulting fragments.

Figure 7:
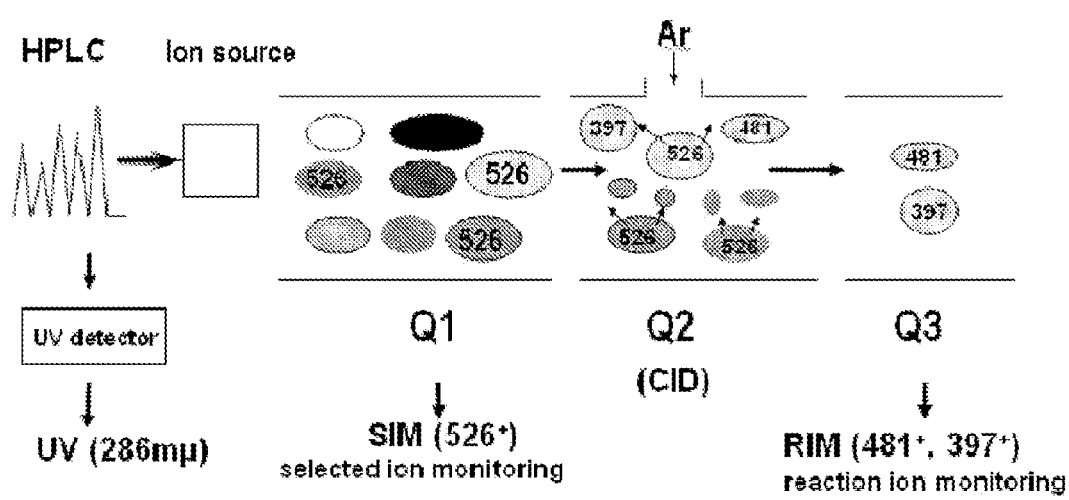
FIG. 7.
Figure 8:
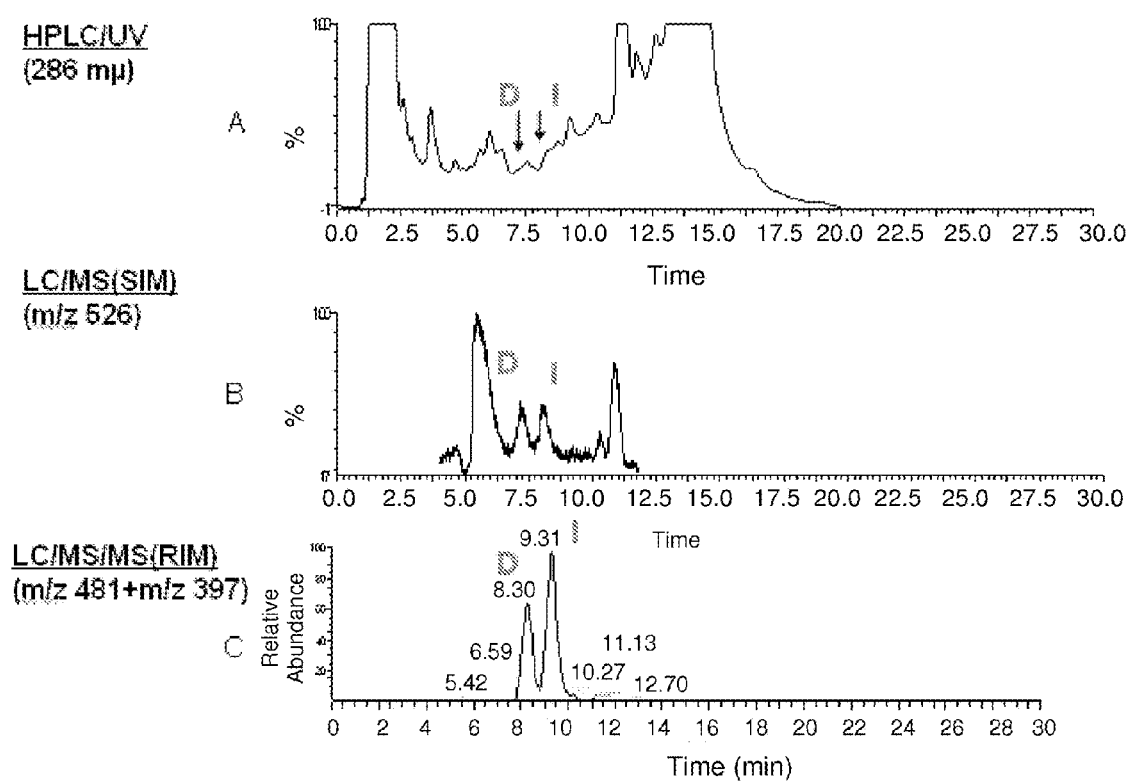
FIG. 8: Shown in FIG. 8 are measurement of D and I in plasma using various methods (HPLC/UV (A), SIM (B), and RIM (C)) described in FIG. 7. This figure demonstrates increasing specificity or sensitivity of the methods using a sample of 0.3 ng D/I in 0.5 mL of COPD plasma. The mass spectrometric method (LC/MS and LC/MS/MS) for the measurement of D/I in urine, plasma and sputum is more sensitive and specific than existing radioimmunoassays and HPLC methods.

Preferably, the technique used to analyze D and I in a sample is LC-MS/MS. This is shown, for example, in FIG. 7. Following HPLC separation, the chromatographic peaks are analyzed by tandem mass spectrometry and measured by selected reaction monitoring (SRM) of two ions m/z 481 and m/z 397, which are two distinct fragment ions produced by collision-induced dissociation (CID) of the molecular ion (m/z 526) of D/I. Q1, Q2, and Q3 in FIG. 7 represent three quadropoles in which Q1 and Q3 are mass sorters and Q2 is used as a collision cell.

More preferably, an internal standard is used which is included with each sample tested. An internal standard that bears a close structural similarity to D and I, an acylated pyridinoline, more preferably acetylated pyridinoline (IS), was used. The structural similarity can be seen in a comparison of the structures, as follows:

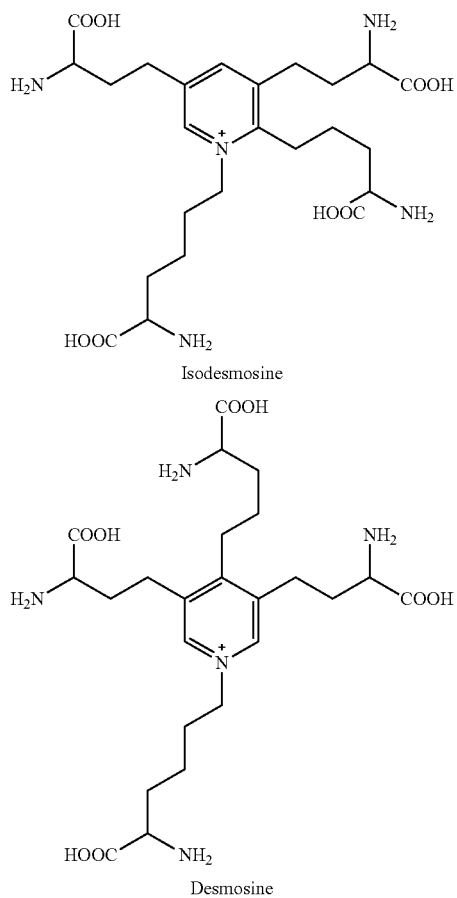

Isodesmosine

Desmosine

-continued

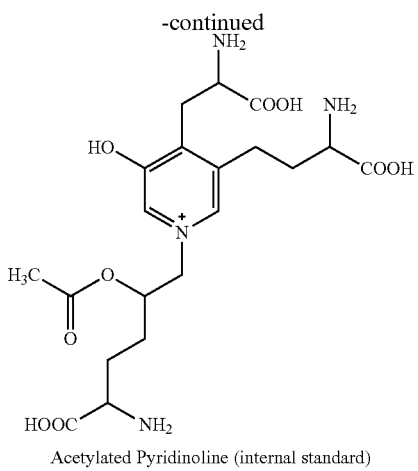

Acetylated Pyridinoline (internal standard)

According to one preferred embodiment of the present invention, methods are provided for validating whether a candidate compound is effective to treat, prevent, or ameliorate the effects of a disease characterized by elastic fiber injury, such as elastin degradation. In such embodiments, the methods comprise determining if the candidate compound decreases the degradation of elastic fiber in a patient administered the candidate compound by measuring, using mass spectrometry employing an internal standard, a marker of elastic fiber degradation in a sample of a body fluid or a tissue of the patient. The invention provides that a decrease in the presence of the marker compared to a control validates that the candidate compound is effective to treat, prevent, or ameliorate the disease. In preferred methods, tandem mass spectrometry is used.

The foregoing methods may be used to validate whether a candidate compound is effective to treat, prevent, or ameliorate the effects of chronic obstructive pulmonary disease (COPD), chronic bronchitis, emphysema, and/or refractory asthma. The marker of elastic fiber degradation that is measured using mass spectrometry employing an internal standard is preferably desmosine, isodesmosine, or combinations thereof. In such embodiments, the marker(s), such as desmosine, isodesmosine, or combinations thereof, are preferably detected and measured within a patient's urine, plasma, and/or sputum. In preferred methods, tandem mass spectrometry is used.

In certain preferred embodiments of the invention, desmosine, isodesmosine, or combinations thereof are measured in plasma. In certain alternative embodiments, total free desmosine, isodesmosine, or combinations thereof are measured in urine. The methods of the present invention may be employed to test the therapeutic value, or effectiveness, of a variety of different candidate compounds. Non-limiting examples of such compounds include hyaluronic acid, polysaccharides, carbohydrates, small molecules, and RNAi molecules, including siRNAs, shRNAs, and others.

According to additional embodiments of the present invention, methods are provided for identifying candidate compounds that are effective to treat, prevent, or ameliorate the effects of a disease characterized by elastic fiber injury. Such methods of the invention comprise (a) administering a candidate compound to an in vivo or in vitro model of the disease, e.g., a cell culture; (b) measuring, by mass spectrometry employing an internal standard, the amount of a marker of elastic fiber injury in the cell culture administered the candidate compound; and (c) determining whether the amount of the marker produced by e.g., the cell culture administered the candidate compound is different compared to e.g., a control cell culture absent the candidate compound. Non-limiting examples of appropriate markers include desmosine, isodesmosine, or combinations thereof. The invention provides that a decrease in the amount of such marker(s) produced by e.g., the cell culture administered the candidate compound compared to e.g., the control cell culture identifies the candidate compound as effective to treat, prevent, or ameliorate the effects of the disease. In preferred methods, tandem mass spectrometry is used.

Such methods may be used for identifying candidate compounds that are effective to treat, prevent, modulate and/or ameliorate the effects of elastin degradation and diseases associated therewith, such as COPD, chronic bronchitis, emphysema, and/or refractory asthma. Similar to the other embodiments discussed herein, the marker that is measured by mass spectrometry employing an internal standard is preferably selected from desmosine, isodesmosine, or combinations thereof. Still further, similar to the other embodiments discussed herein, such methods may be employed to test the therapeutic value, or effectiveness, of a variety of different candidate compounds, including hyaluronic acid, polysaccharides, carbohydrates, small molecules, and RNAi molecules, such as siRNAs, shRNAs, and others. In preferred methods, tandem mass spectrometry is used.

The following examples are provided to further illustrate the methods of the present invention. These examples are illustrative only and are not intended to limit the scope of the invention in any way.

Example 1—D and I Measurements

In these examples, measurements of desmosine (D) and isodesmosine (I) in plasma, urine and sputum are described. The results demonstrate a statistically significant difference between normal controls and patients diagnosed with COPD and further suggest that measurements of D and I in plasma may be a discriminating index for distinguishing patients with COPD from normal subjects. D and I were measured in plasma, urine and sputum in a cohort of patients diagnosed with COPD related to smoking and a second cohort in whom COPD is related to Z-phenotype alpha-1 antitrypsin deficiency (AATD) as well as smoking.

Materials and Methods

The mass spectrometric method was used for direct measurement of D/I in urine, plasma and sputum as markers of elastin degradation in healthy controls, patients with α1-antitrypsin deficiency (AATD) and non-AATD-related COPD. Preparation of specimens of urine and sputum and measurements by mass spectrometry (LC/MS) were performed as previously described in Ma S, Lieberman S, Turino G M and Lin Y Y: The detection and quantitation of free desmosine and isodesmosine in human urine and their peptide-bound forms in sputum[11]. D and I standard (mixed 50% D and 50% I) were purchased from Elastin Products (Owensville, Mich.), and all other reagents were from Sigma (St. Louis, Mo.). MCX cation exchange cartridges (3 ml) were obtained from Waters (Milford, Mass.), and CF1 cellulose powders were purchased from Whatman (Clifton, N.J.).

Urine Samples.

Twenty-four hour urine samples were collected and analyzed as previously described[11].

Plasma Samples.

Plasma samples were obtained after centrifuging venous blood specimens at 2500 r.p.m. for 25 min. Samples were stored at −20° C. until used. One ml of plasma and 1 ml of concentrated HCl (37%) were placed in a glass vial. After air in the sample was displaced with a stream of nitrogen, the sample was acid hydrolyzed for 24 hours in 6N HCl. After evaporation to dryness, the residue was dissolved in 2 ml of a mixed solution of n-butanol/acetic acid/6 N HCl (4:1:1, by volume). The sample solution was loaded onto a 3 ml CF1 cartridge. The CF1 cartridge was prepared by introducing 3 ml of the slurry of 5% CF1 cellulose powder in a mixture of n-butanol/acetic acid/water (4:1:1, by volume). The cartridge was washed 3 times with 3 ml of n-butanol/acetic acid/water mixture, and D and I adsorbed in the CF1 cartridge were eluted with 3 ml of water. The eluate was evaporated to dryness under vacuum at 45° C. and the residue was dissolved in 0.1 ml of HPLC mobile phase for LC/MS analysis. For analysis in plasma, samples were processed and measured in duplicate and the results averaged.

Sputum Samples.

Sputum samples were processed as previously described[11] with the following modification: The acid hydrolyzed samples were chromatographed using a CF1 cartridge as described in the treatment of plasma samples. Each sputum sample was processed and measured in duplicate and the results averaged. Sputum was obtained from 3-hour morning collections spontaneously produced. When subjects could not voluntarily produce sputum, sputum induction was induced by 3% saline inhalation for 20 minutes as previously described[11].

Recovery of Desmosine and Isodesmosine in Urine and Plasma.

Using D and I as the external standards we performed studies to ensure recovery and reproducibility of the analysis in urine and plasma. Triplicates of two urine samples, were spiked with 0.4 pmol and 2.0 pmol each of D and I standards, and carried through HCl hydrolysis and chromatography procedures as described. The recoveries of D and I from one urine spiked with 2.0 pmol of D and I were 91±4% and 88±1%, and that spiked with 0.4 pmol of D and I were 92±3% and 93±8%. The recoveries of D and I from the other urine spiked with 2.0 pmol of D and I were 88±1% and 93±3%, and that spiked with 0.4 pmol of D and I were 93±6% and 93±15%. The reproducibility of the repeated sample analysis ranges from 91-99%.

Similar recovery studies were carried out with 4 plasma samples. The recoveries of D and I with 0.05 ng standards were 65±4 and 74±13%, and that with 0.1 ng standards were 67±1 and 72±4%. The reproducibility of the repeated sample analysis is 83-99%. Values in urine and plasma were corrected for recovery losses.

Creatinine and Protein Measurement were carried out as previously described[11]. LC/MS Analysis was performed also as previously described[11], with slight modification (see description of FIG. 1A).

Data Analysis.

The t-test adjusted for unequal variance was used to test the null hypothesis. The level of significance was 0.05. P-values were calculated based on the summed values of D and I using the unpaired t-test with Welch's correction.

Patients.

Study patients were diagnosed with chronic obstructive pulmonary disease and adhere to Gold Criteria grades 1-4. All patients were screened for AATD by serum levels and phenotyping. Patients were divided into two groups: 1) with normal levels of alpha-1 antitrypsin in serum, and 2) those with ZZ-homozygous alpha-1 antitrypsin deficiency. Patients gave informed consent for the study. The study was approved by the Institutional IRB.

All patients with normal levels of alpha-1 antitrypsin had significant smoking histories of from 10 to 60 pack years. Many had stopped in the previous ten years and none were current smokers when studied. Among these patients the age range was 44 to 85. Five were males and 2 females.

Among patients with alpha-1 antitrypsin deficiency all but one had a significant smoking history exceeding ten pack years. All patients had ceased smoking for at least ten years by the time of study. All AATD patients were being treated with AAT protein replacement, were in a stable clinical state and exhibited no evidence of an exacerbation.

Control subjects were selected by a clinical history free of any specific known disease or significant symptoms, including respiratory symptoms, and none had ever smoked.

Results

Results in normal subjects are presented in Table 1 below (C=Caucasian; A=Asian).

TABLE 1

Controls without Lung Disease

| | | | | Desmosine/Isodesmosine | | | | |
| | | | | Plasma | | Urine | | |
| | | | | | | Free Form | | Free/ |
| Subjects | Sex | Age | Race | ng/ml | ng/g protein | µg/g creatinine | Total | Total % |
|---|---|---|---|---|---|---|---|---|
| 1 | M | 33 | C | 0.11/0.10 | 1.89/1.80 | 1.85/1.11 | 9.64/5.90 | 19/19 |
| 2 | M | 35 | C | 0.07/0.09 | 1.06/1.36 | | | |
| 3 | F | 58 | C | 0.10/0.08 | 2.17/1.74 | 3.73/2.76 | 10.22/7.65 | 36/36 |
| 4 | M | 27 | A | 0.09/0.07 | 1.31/1.02 | 0.60/0.50 | 2.85/2.70 | 21/19 |
| 5 | F | 31 | A | 0.10/0.06 | 2.22/1.29 | | | |
| 6 | F | 69 | C | 0.09/0.08 | 1.62/1.44 | 1.80/1.69 | 11.77/8.37 | 15/20 |
| 7 | M | 54 | A | 0.11/0.13 | 2.02/2.27 | 0.51/0.64 | 5.17/3.96 | 10/16 |
| 8 | M | 72 | A | 0.09/0.13 | 1.94/2.80 | 0.75/0.35 | 5.16/4.10 | 15/9 |
| 9 | M | 79 | C | 0.12/0.05 | 2.43/1.01 | 0.42/0.38 | 6.17/4.67 | 7/8 |
| 10 | M | 65 | A | 0.11/0.10 | 2.23/2.03 | 0.99/0.66 | 6.59/3.89 | 15/17 |
| 11 | F | 38 | A | 0.13/0.08 | 2.27/1.31 | 0.89/0.88 | 5.19/4.26 | 17/21 |

TABLE 1-continued

Controls without Lung Disease

| | | | | Desmosine/Isodesmosine | | | | |
| | | | | Plasma | | Urine | | |
| | | | | | | Free Form | | Free/ |
| Subjects | Sex | Age | Race | ng/ml | ng/g protein | µg/g creatinine | Total | Total % |
|---|---|---|---|---|---|---|---|---|
| 12 | F | 28 | C | 0.11/0.09 | 1.83/1.50 | 2.48/1.58 | 12.69/6.64 | 20/24 |
| 13 | M | 32 | C | 0.10/0.08 | 1.87/1.49 | 1.59/1.56 | 7.29/5.68 | 22/27 |
| mean | | | | 0.10/0.09 | 1.91/1.62 | 1.42/1.10 | 7.52/5.26 | 18/20 |
| ±SEM | | | | ±0.01/±0.01 | ±0.11/±0.14 | ±0.31/±0.22 | ±0.94/±0.53 | ±2/±2 |

The mean levels and standard error (S.E.M.) of D and I (D/I) in plasma in 13 subjects were 0.10±0.01/0.09±0.01 ng/ml plasma and 1.91±0.11/1.62±0.14 ng/g protein.

Figure 2:
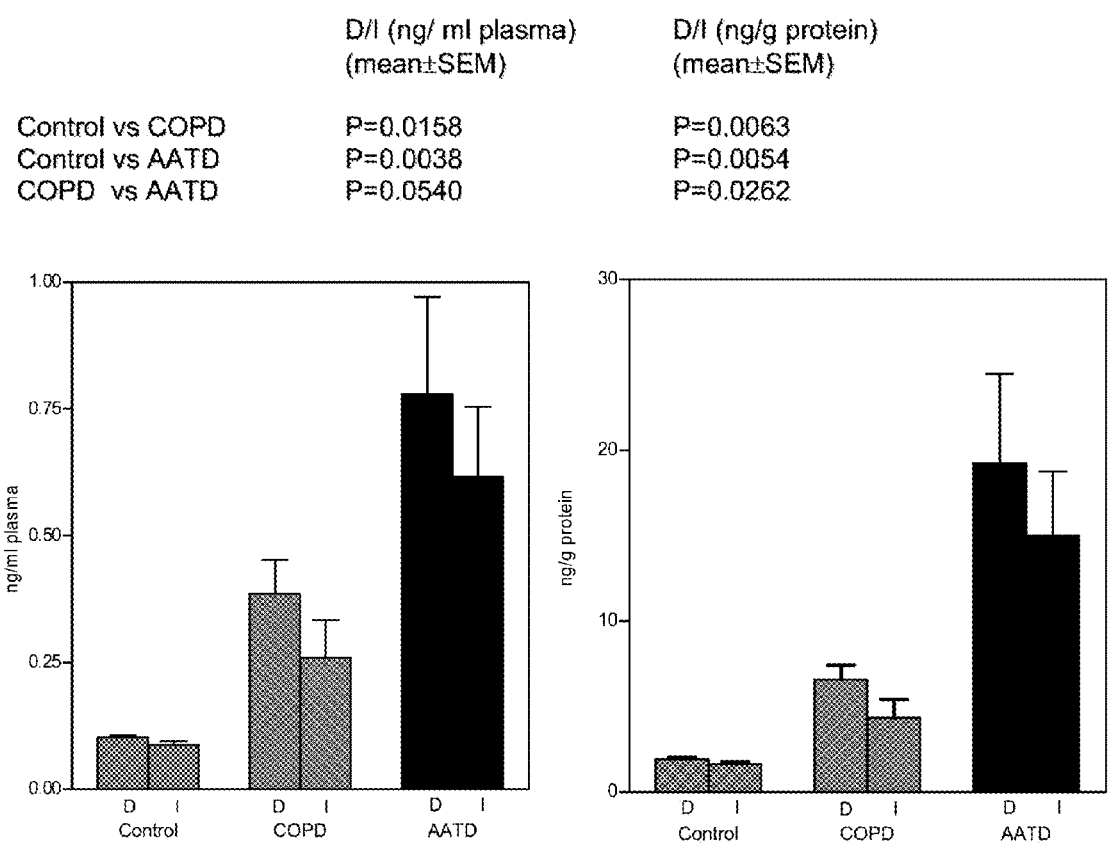
FIG. 2: Shown in FIG. 2 are mean levels and standard errors of the mean of D and I in plasma for normal controls, patients with COPD without alpha-1 antitrypsin deficiency (AATD) and patients with COPD with AATD. The differences among all three groups are statistically significant. P-values are calculated based on the summed values of D and I using the unpaired t-test with Welch's correction.

Results for levels of D and I (D/I) in plasma in patients with COPD with normal levels of AAT are presented in FIGS. 2 and 5. The mean and S.E.M. were 0.39±0.07/0.26±0.07 ng/ml of plasma and 6.60±0.84/4.36±1.04 ng/g protein, which are statistically significantly higher than controls. Results for levels of D and I in plasma in patients with COPD related to AATD are shown in FIGS. 2 and 6. The mean and S.E.M. are 0.78±0.19/0.62±0.14 ng/ml of plasma and 19.24±5.22/15.03±3.71 ng/g protein, which values are statistically significantly higher than control values and the levels in COPD not related to AATD when calculated per gm of protein in plasma.

Figure 3:
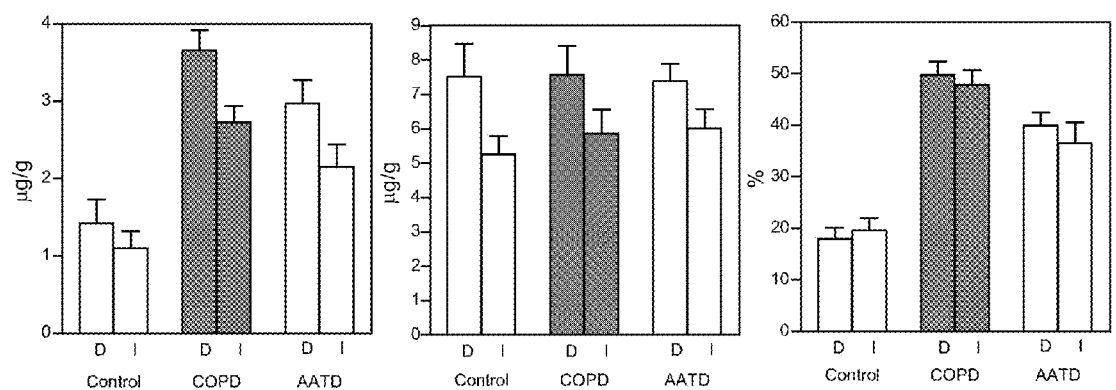
FIG. 3: Shown in FIG. 3 are mean levels and standard errors of the mean of D and I in urine of normal controls, patients with COPD without AATD and COPD with AATD. Mean differences among the groups are statistically significant for the free D and I and % of free/total D and I urinary excretion. P-values calculated as in FIG. 1.

It is noteworthy that no overlap of levels of plasma D and I exists between controls and the patient groups with COPD; patients' levels are consistently higher. The levels of D and I in urine in control subjects and patients with and without AATD are shown in Table 1 and FIGS. 3, 5 and 6. The levels of free D and I (D/I) are 3.66±0.26/2.72±0.21 ng/g creatinine in COPD with normal levels of AAT and 2.97±0.30/2.15±0.29 in patients with AATD which values are statistically significantly higher than control subjects (1.42±0.31/1.10±0.22). As shown in FIG. 3, the percentage of free D and I over total D and I excretion was statistically significantly higher in both groups with COPD, but highest in COPD with normal AAT levels. The mean total 24 hour excretion of D and I was not statistically significantly increased in both COPD groups as compared to controls.

Figure 4:
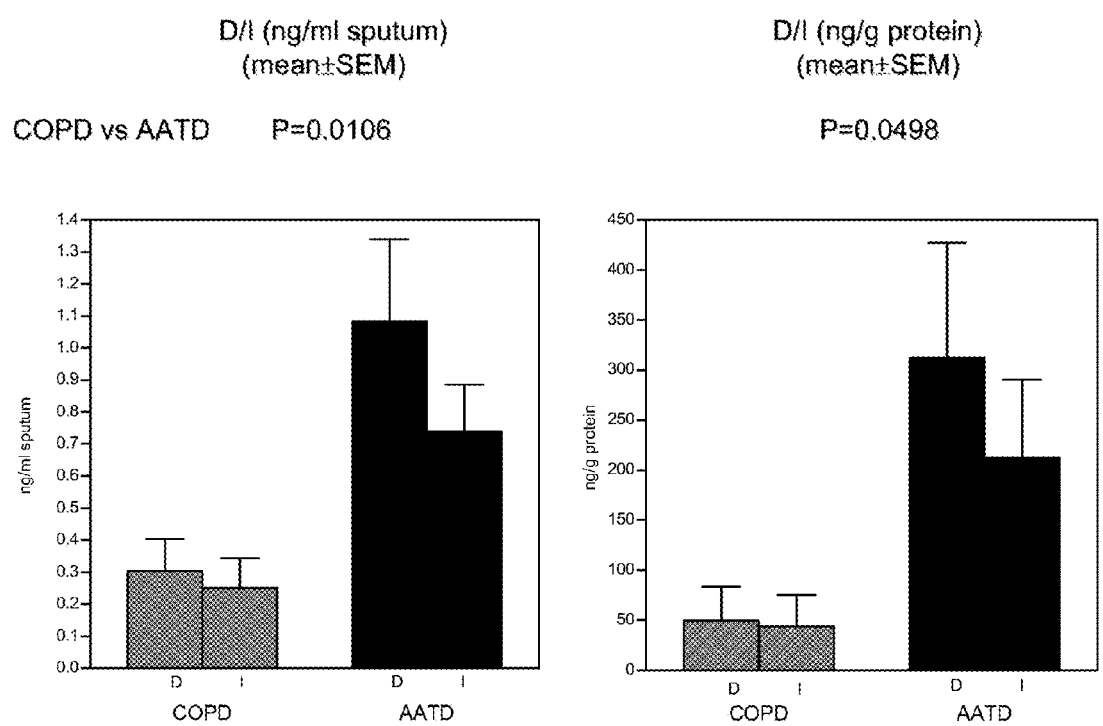
FIG. 4: Shown in FIG. 4 are mean levels and standard error of the mean of D and I in sputum of patients with COPD without AATD and COPD with AATD. Control subjects do not have detectable D or I in induced sputum. The content of D and I in sputum of patients with COPD and AATD is statistically significantly higher than in those with COPD and without AATD. P-values calculated as in FIG. 1.

Levels of D and I in sputum are shown in FIGS. 4-6. The levels of D and I were below the level of detection by mass spectrometry in 3 control subjects, whereas both groups of COPD patients showed mean levels of D and I to be significantly increased to 1.08±0.26/0.74±0.15 ng/ml and 0.30±0.10/0.25±0.09 ng/ml of sputum in COPD patients with and without AATD respectively. Results expressed per g of protein in sputum for D and I (D/I) were 312±115/212±77.9 and 49.9±33.4/43.9±31.5 in patients with and without AATD. D and I in sputum was statistically significantly higher in AATD patients.

Shown in Table 2 below are repeat measurements of plasma D and I in 1 control subject, 1 patient with AATD related COPD and a patient with COPD without AATD. Intervals between repeat measurements were days in subjects with AATD and COPD to weeks and months for the other two subjects. During these intervals, each patient was in a stable clinical state without exacerbations.

TABLE 2

Repeat Measurements of Desmosine and Isodesmosine in Plasma

| D/I (ng/ml) | D/I (ng/g protein) |
|---|---|
| Normal Subject - 14 month interval | |
| 0.12/0.05 | 2.43/1.01 |
| 0.11/0.07 | 2.11/1.34 |
| Patient with COPD and AATD - 2 day interval | |
| 2.31/1.75 | 54.91/41.60 |
| 2.53/2.08 | 55.90/45.96 |
| 2.55/2.49 | 61.31/59.87 ng/g protein |
| Patient with COPD without AATD - 6 month interval | |
| 0.49/0.44 | 9.32/8.37 |
| 0.32/0.31 | 7.04/6.82 |

The results varied between 10 and 15%, which suggests a stable metabolic state with respect to elastin turnover in each individual's normal or abnormal levels.

Levels of D and I (D/I) in plasma and urine were analyzed for possible correlation with age, sex, racial origin or physiological parameters of $FEV_1$ and RV/TLC and no statistically significant correlations were determined.

Data Analysis

An early insight into the mechanisms leading to alveolar disruption in pulmonary emphysema is that lung matrix elastin is a target for chemical degradation from cellular elastases. Lung elastin content, determined chemically, has been demonstrated to be low in pulmonary emphysema related to smoking or to the Z-phenotype AATD, and morphologically, lung elastin fibers have been shown to be fragmented and disordered. Also intratracheal administration of elastases has uniquely produced animal models of pulmonary emphysema. In addition, elastin peptides have been shown to be chemotactic for neutrophils and macrophages and could be a factor in the progression of human pulmonary emphysema once elastin degradation has occurred.

Current methods of measuring elastin peptides in blood plasma require radioimmunoassay techniques which depend on antibodies to elastin peptides which vary in specificity and sensitivity, which affects the standardization and quantification of peptides. Also, measurements of D and I in urine require a relatively extensive chemical procedure using isotope dilution corrections and HPLC, which can be an arduous methodology.

Recognizing these limitations, mass spectrometry, with its ability to detect specific molecular species with high sensitivity, accuracy and specificity is a readily applicable method for use in complex body fluids. The increased sensitivity of mass spectrometry has permitted the measurement of a free component unbound to protein or other matrix constituents of D and I in urine which are increased statistically significantly in patients with COPD as compared with normals. Similarly, mass spectrometry has allowed measurements of D and I in blood plasma and sputum, both chemically complex media. Attempts to detect a free vs. bound component of D and I in plasma were unsuccessful. The concentration of D and I in a single small sample of plasma may be too low for detection compared to the concentration of D and I in a 24-hour collection of urine.

The increased free component of D and I in urine in COPD patients, we believe, may reflect an increased neutrophil elastase concentration in circulating neutrophils, which has been demonstrated by previous measurements as an increase in lysosomal elastase in neutrophils of COPD patients as compared with normals. This increased elastase concentration may reflect a generalized immunological hyperreactivity resulting from the chronic inflammatory state of the lung in COPD, manifested by increased elastase activity in neutrophils and macrophages.

The difference in levels of D and I in plasma between controls and patients with COPD in this study suggests that D and I in plasma may be one of the sensitive indicators of the presence of lung elastin breakdown in COPD, especially since the entire cardiac output constantly circulates through the lung. While changes in levels of D and I in plasma cannot be assumed to reflect D and I from lung parenchyma per se, the demonstrated presence of D and I in sputum of patients with COPD indicates that increased degradation, and probably turnover, of elastin is occurring in lung, since normal subjects do not have detectable amounts of D and I in induced sputum.

In the limited number of our controls we did not find any correlation of the age of the subjects with urinary excretion or plasma levels of D and I. In other studies of adult subjects which include similar measurements no correlations with age have been reported.

Measurements of total excretion of D and I in 24 hour urine collection did not demonstrate statistically significant differences between patients and normals. This result is consistent with the demonstration of Bode et al., who showed marked variability in daily excretion of D and I in COPD patients and no statistically significant difference in the total excretion between the two cohorts[42]. Also, Starcher et al. have demonstrated a failure of urine to reflect the rapid degradation of lung elastin produced by intratracheal porcine pancreatic elastase in mice. Their studies demonstrated a sequestering of elastin peptides in renal parenchyma following lung elastin breakdown and a continued slow urinary excretion of D containing peptides over several days following acute elastase injury[122]. Other studies have shown significant increases of urinary D in COPD patients compared to normals. Possibly the individual patient population in the present study varied from those previously studied. In that regard, none of the patients in this study were actively smoking, which has been shown to increase urinary desmosine excretion.

When elastin degradation is mildly, or even moderately, increased above the turnover in normals, it may be difficult to reflect this increase in urine, even with 24-hour collections. However, the percentage of the free component of D and I in urine is consistently elevated in both groups of patients with COPD.

It has long been demonstrated that elastin in elastin fibers, once formed, cross-linked and insoluble, is extremely stable and undergoes little metabolic turnover. This slow metabolic turnover in normal humans is consistent with the very low levels of D and I in normal plasma. It is noteworthy that studies of elastase injury to lung elastin in vivo in rats and mice demonstrate that rapid degradation of elastin occurs when exposed to elastases, with rapidly ascending concentrations of elastin peptides in blood and urine within hours of protease administration. Notable also is the rapid resynthesis of elastin after proteolytic breakdown. The stability of plasma and urine levels of desmosine with repeat measurements over a 44 day interval in patients with AATD was reported by Stolk et al., which is consistent with measurements in this study[123]. Thus any increase in elastase activity in lungs, which includes bronchial and blood vessel elastin as well as alveolar, may well be reflected in the circulating blood to and from the lung.

The persistence of elevated levels of D and I in plasma in patients with COPD in both patient cohorts long after smoking cessation is consistent with continued inflammation of the lung in COPD and progression of matrix tissue injury.

The blood levels of D and I in COPD patients may therefore prove to be a sensitive index of the metabolic state of elastin degradation and possibly resynthesis in the lung. Since elastin is a significant structural constituent of alveoli, bronchial walls and blood vessels, the levels of D and I in the earliest phases of COPD deserve to be evaluated. Also the responses to therapeutic agents which may reduce the lung inflammatory state and thereby reduce elastin degradation may be assessed by measurements of D and I in plasma and the proportion of free D and I in urine.

It is noteworthy that the AATD patients had higher levels of D and I in plasma than COPD patients without AATD, along with higher levels in sputum consistent with the AATD patients' form of COPD to be emphysematous with loss of lung mass. All patients with AATD were receiving AAT augmentation therapy at the time of study. Since levels of D and I in body fluids were not obtained prior to the initiation of augmentation therapy, it cannot be assumed that AAT replacement is having no beneficial effect. These data suggest that an evaluation of the effect on D and I levels of higher doses of AAT augmentation would be worthwhile.

Mass spectrometry allows measurements of D and I separately. The proportion of D and I in plasma and urine in control subjects shows a slightly lower proportion of isodesmosine constituting approximately 80% of the level of desmosine. In one study of the amino acid composition of human lung elastin, D exceeded I content by approximately 10-15%, which is close to agreement with the present study[124]. It is noteworthy that patients with COPD in both groups had proportions of D and I which are similar to controls, suggesting that resynthesis of elastin in these groups does not show major structural dissimilarities from normals.

The results of this study indicate that levels of D and I in urine which includes an unconjugated fraction, along with levels in plasma and sputum may be useful parameters to characterize patients with COPD of various phenotypes at various phases of the disease. Mass spectrometry, with its increased specificity and sensitivity, should facilitate this characterization.

Example 2—Effect of Tiotropium Treatment

COPD patients have elevated levels of D/I in plasma, urine and sputum, which might respond to prolonged bronchodilation. To determine if clinical effects of Tiotropium (TIO) affect tissue degradation of the lung in COPD, clinically stable patients with COPD (n=9) not on TIO prior to the study and at one month and a second month after initiating therapy were tested. Other anticholinergic bronchodilators were stopped prior to TIO, and other therapies/disease treatments were unchanged for the two months of study. To these patients, 18 mcg TIO was administered each 24 hours. D/I in plasma, urine and sputum were measured by liquid chromatography and mass spectrometry (LC/MS) prior to the study and at one month and two months after the study.

Figure 10:
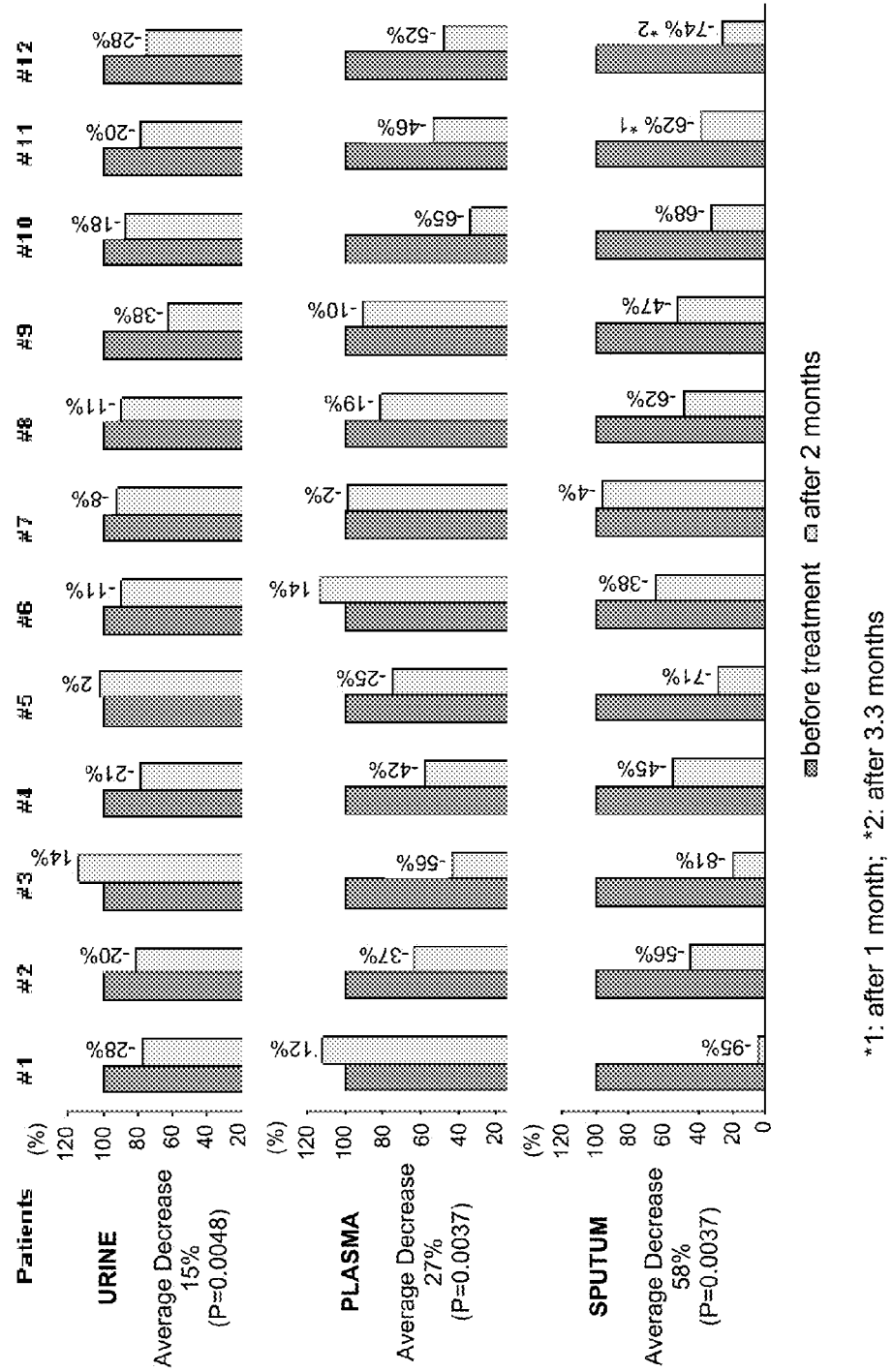
FIG. 10: Shown in FIG. 10 are percent decrease in D/I levels in urine, plasma, and sputum from patients before treatment and two months after treatment with Tiotropium.

Prior to the study, levels of D/I in plasma and sputum were above normal in all patients studied, and the percentage of free D/I in urine was also increased. Significant decreases in D/I levels were observed in urine (10 out of 12), in plasma (10 out of 12) and in sputum (all 12 patients), which may reflect decreases in lung elastin degradation of COPD patients on TIO therapy. (FIG. 9). Calculated percentage decreases in D/I levels after TIO treatment showed decreases beginning after one month with further decreases observed in the second month. After two months of treatment, larger decreases in D/I levels were observed in sputum and plasma than urine. The response was not always uniform in the respective patients' urine, plasma, and sputum. For example, two patients (#3 and #5) failed to show responses in urine but showed decreases in their plasma and sputum, and two other patients (#1 and #6) did not show decreases in plasma but showed decreases in urine and sputum. (FIG. 10).

Overall results of percent decreases in D/I levels indicated that all 12 COPD patients were responding to prolonged TIO treatment with some decrease in lung elastin degradation. Spirometry in most post-TIO therapy patients shows significant increase in Force Vital Capacity (FVC), Forced Expired Volume in 1 second (FEV1), and ratio of FEV1/FVC and decreases in Residual Volume (RV). The improvement in spirometric indices were usually concordant with levels of D/I in patients.

Overall results demonstrate that two months of treatment with TIO in patients is accompanied by significant reductions in D/I levels in plasma, urine and sputum, consistent with a reduction in elastin degradation and possibly an anti-inflammatory effect. Thus, this example confirms the effectiveness of the methods disclosed and claimed herein for, e.g., validating whether a candidate compound is effective to treat, prevent or ameliorate the effects of a disease characterized by elastic fiber injury, such as COPD, COPD with AATD, chronic bronchitis, emphysema, or refactory asthma.

Example 3—Analysis Using LC/MSMS and Internal Standard (IS)

D and I concentrations were determined in urine, plasma, and sputum samples using LC/MSMS with an internal standard which was acetylated pyridinoline (IS).

Preparation of specimens of urine, plasma, and sputum was performed as described in Example 1. MCX cation exchange cartridges (3 ml) and CF1 cellulose powders were as indicated in Example 1. D and I standards (mixed 50% D and 50% I) were obtained from Elastin Products (Owensville, Mich.). Acetylated pyridinoline was obtained from Quidel (San Diego, Calif.). All other reagents were from Sigma (St. Louis, Mo.).

Acid Hydrolysis:

0.2 mL of urine, or 0.5 mL of plasma or sputum were placed in a glass vial with equal volumes of concentrated HCl (37%). Air in the vial was displaced with nitrogen, and was heated at 110° C. for 24 hrs. The hydrolyzed sample was filtered and evaporated to dryness. For the free forms of D and I analysis, samples were analyzed directly without the HCl hydrolysis.

Cellulose (CF1) Cartridge Treatment:

The internal standard, acetylated pyridinoline (IS) was added to the acid hydrolyzed and unhydrolyzed (for free D and I) samples; 1 ng was added to urine samples and 0.5 ng was added to plasma and sputum samples. The sample mixtures were dissolved in 2 mL of n-butanol/acetic acid/water (4:1:1), and applied onto a 3 mL cellulose cartridge, which was prepared by introduction of 3 mL of 5% CF1 slurry in n-butanol/acetic acid/water (4:1:1) (well dispersed slurry by stirring for 24 hrs). The cartridge was washed 3 times with 3 mL of n-butanol/acetic acid/water (4:1:1), and the components retained in the cartridge were eluted with 3 mL of water, dried and dissolved in 200 µl of LC mobile phase.

LC/MSMS Analysis.

A TSQ Discovery electrospray tandem mass spectrometer (Thermoelectron) was used for the LC/MSMS analysis. HPLC separation of D and I was achieved using a 2 mm×150 mm dC18 (3 µm) column (Waters, Milford, Mass.) with mobile phase A (7 mM HFBA/5 mM NH4Ac in water) and mobile phase B (7 mM HFBA/5 mM NH4Ac in 80% acetonitrile). The HPLC was programmed linearly from 100% A to 82% A in 12 mins. The tandem mass spectrometry (LC/MSMS) technique monitors ions of m/z 481 and m/z 387. Selected reaction monitoring (SRM) of D and I (m/z 526 to m/z 481+397) and IS (m/z 471 to m/z 128) were used for the quantitative measurement to determine D and I concentration in the samples.

Sample Spectrograms.

Spectrograms from analysis of samples from a patient of urine (free D and I), urine (total D and I), plasma and sputum, in which each sample was tested three times, are provided in FIGS. 14A-14D.

Calculation.

To determine the concentrations of D and I in the samples, the ratio of the analyte response to the internal standard response is ascertained. The calculation used is shown in FIG. 13.

Reproducibility.

From the three measurements taken per sample using LC/MSMS with IS, the coefficient of variance was calculated.

| Urine Free D/I (µg/g Creatinine) | | Urine Total D/I (µg/g Creatinine) | |
|---|---|---|---|
| Mean | 7.45 | Mean | 15.98 |
| ±SD | 0.91 | ±SD | 1.76 |
| % CV | 12 | % CV | 11 |

| Plasma D/I (ng/ml) | | Sputum D/I (ng/ml) | |
|---|---|---|---|
| Mean | 0.23 | Mean | 0.23 |
| ±SD | 0.03 | ±SD | 0.01 |
| % CV | 13 | % CV | 4 |

In comparison, representative samples in which three measurements were taken per sample were identified from data in which D and I were measured using LC/MS. The comparative data is provided as follows:

| | Urine<br>Free D/I<br>(µg/g Creatinine) | | Urine<br>Total D/I<br>(µg/g Creatinine) |
|---|---|---|---|
| Mean | 0.93 | Mean | 9.75 |
| ±SD | 0.20 | ±SD | 0.96 |
| % CV | 22 | % CV | 10 |

| | Plasma<br>D/I (ng/ml) | | Sputum<br>D/I (ng/ml) |
|---|---|---|---|
| Mean | 0.63 | Mean | 0.52 |
| ±SD | 0.21 | ±SD | 0.11 |
| % CV | 33 | % CV | 21 |

As can be seen, the coefficient of variance from a representative sample of urine (Total D/I) measured by LC/MS was about 10%. The other representative samples, however, had about or above 20% variance. The CV % for an urine (free D/I) sample was 22% and the CV % for a sputum sample was 21%. For a plasma sample, the CV % was as high as 33%.

For the measurements taken using LC/MSMS with IS, on the other hand, the reproducibility was significantly and unexpectedly improved. All of the samples had a CV % below 15%, and the particular CV percentages spanned from 4% (for sputum sample) to 12% (for urine (free D/I) sample). The use of tandem MS employing an internal standard shows significant improvement in reproducibility. Thus, the technique advances the importance of desmosine and isodesmosine as reliable biomarkers in biological fluids for the detection of elastin degradation in diseases characterized by elastic fiber injury such as COPD. Moreover, using the process according to the present invention it is now possible to obtain CV percentages within FDA approved limits (i.e., generally below 15%).

Example 4—Effect of Hyaluronan on Smoke-Induced Elastic Fiber Injury

In the current study, we used the D/I biomarker to determine both the progression of elastic fiber damage in a mouse model of smoke-induced pulmonary emphysema and the potential therapeutic effects of aerosolized hyaluronan (HA) on smoke-induced injury. This agent has previously been shown to significantly reduce smoke-induced airspace enlargement and prevent elastic fiber injury when given concurrently with smoke[15]. The current investigation modifies the original experimental protocol by delaying therapeutic intervention for 1 month following initiation of smoke exposure, thereby providing a more clinically relevant approach to evaluating this form of treatment. The ability of HA to limit airspace enlargement and prevent elastic fiber injury, despite pre-existing smoke-induced lung injury, would support clinical testing of this agent in patients who already have significant evidence of COPD.

Methods
Experimental Plan

Eight-week-old female DBA/2J mice (The Jackson Laboratory, Bar Harbor, Me.) were divided into two treatment groups as follows: Group 1 was treated with aerosolized HA, beginning 1 month following initiation of smoke exposure; Group 2 was treated with aerosolized water, beginning 1 month following initiation of smoke exposure. Groups 1 and 2 were exposed to smoke for 3 h per day, 5 days/week, for a period of 10 months. Group 1 was treated with a 0.1% solution of HA in water for 1 h prior to each smoking session. Group 2 received aerosolized water for a similar interval. At various intervals following initial smoke exposure, animals were euthanized to determine (1) DID content in bronchoalveolar lavage fluid (BALF) and whole lungs at 2, 4, 6, 8, and 10 months; (2) lung histopathology at 3, 6, and 10 months; and (3) airspace enlargement as measured by the mean linear intercept (MLI) at 3 months.

Exposure to Cigarette Smoke

Following administration of either aerosolized HA or water, the nebulizer was disconnected and the smoking machine (Model TE-10, Teague Enterprises, Davis, Calif.) was attached to the exposure chamber. Both treatment groups were exposed to cigarette smoke for a period of 3 h/day, 5 days/week. The smoking machine simultaneously burned two filtered research-grade cigarettes (type 2R4F, University of Kentucky). Each cigarette was puffed once per minute for 2 s at a flow rate of 1.05 LPM, yielding 35 cc of smoke. This cycle was repeated nine times before ejecting the cigarette and loading a new one. Proper flow rate was maintained by a vacuum pump that established negative pressure at the exhaust port.

Exposure to HA Aerosol

Beginning 1 month following initial smoke exposure, Group 1 was administered a 0.1% solution of low-molecular-weight (150 kDa) streptococcal HA in water (Bayer, Shawnee, Kans.), using a Misty-Ox nebulizer (Vital Signs, Totowa, N.J.). Group 2 received aerosolized water alone. The nebulizer was connected to a heavy-duty air compressor that delivered a constant pressure of 30 psi. The aerosol entered the exposure chamber through an inflow port attached to the roof and was drawn through the chamber by negative pressure created by a vacuum pump connected to an exhaust port on the side wall. The chamber was large enough (28×19×15 in.) to permit the mice to remain in their cages while inhaling the aerosol, thereby minimizing direct handling of the animals.

Light Microscopic Studies

At 3, 6, and 10 months following initiation of smoke exposure, mice were asphyxiated with $CO_2$ and their lungs were inflated in situ with 10% neutral-buffered formalin at a constant pressure of 20 cm $H_2O$. After 2 h, the chest contents were removed and fixed for several days in formalin. The extrapulmonary structures were then dissected off and the lung tissues were randomly cut and entirely submitted for histological processing. Slide sections stained with hematoxylin and eosin were examined with the light microscope to determine histological changes and to quantify airspace diameter by the mean linear intercept method[16]. Additional sections were treated with the Verhoeff-Van Gieson stain to identify elastic fibers.

Measurement of DID

The levels of the elastin-specific crosslinking amino acids, DID, were measured in both BALF and whole-lung tissues. Animals were asphyxiated with $CO_2$ and their lungs were lavaged three times with 1-ml aliquots of Hanks' solution. Both cell-free lavage fluids and homogenized lung tissues were then hydrolyzed in 6 N HCl at 110° C. for 24 h, and the hydrolysates were filtered and evaporated to remove acid. DID were quantified by high-performance liquid chromatography and electrospray ionization mass spectrometry according to previously published procedures[11].

Data Analysis

All data were expressed as mean±standard error of the mean (SEM). The two-sample t-test was used to determine statistically significant differences between treatment groups.

Results

BALF DID

Figure 15:
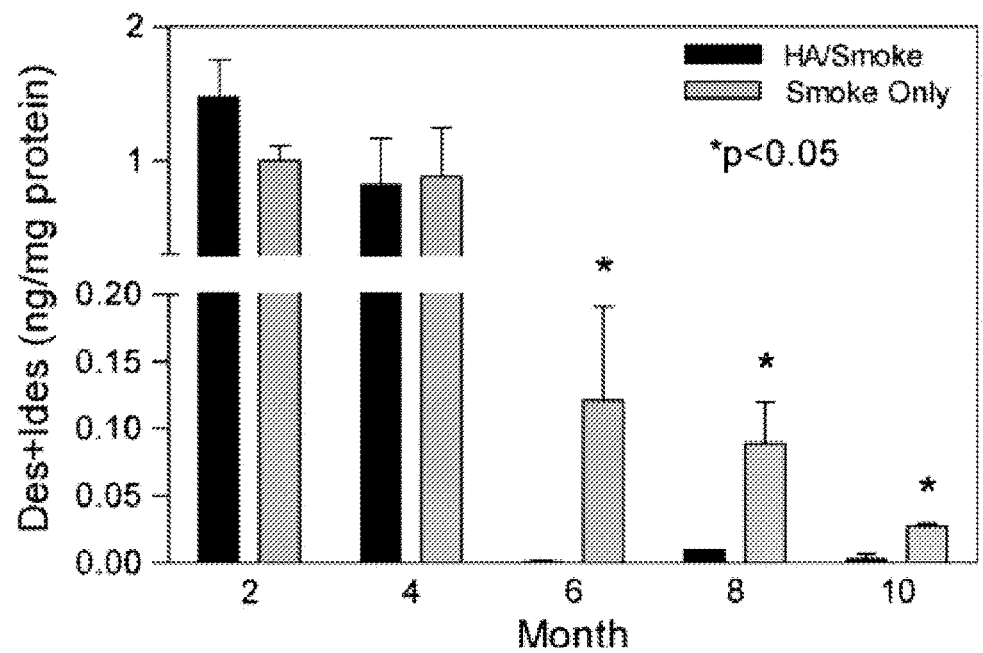
FIG. 15: The levels of BALF DID in both treatment groups showed a marked decrease after 4 months of smoke exposure. Although differences between the groups were not statistically significant at 2 and 4 months, subsequent measurements in the HA-treated animals were significantly lower (n 3 for each bar). Levels of DID were undetectable (≤1 pg/mg protein) in 8-week-old animals that were not exposed to either HA or smoke (not shown; n=4).

As shown in FIG. 15, the amount of BALF DID in both the HA/Smoke (Group 1) and Smoke-Only (Group 2) groups dropped precipitously after 4 months of smoke exposure. In the HA/Smoke group, there was a decrease from 0.8 ng/ml to less than 1 pg/ml during this interval. While differences in BALF DID between the groups were not statistically significant at 2 and 4 months, subsequent measurements showed significantly lower levels of these amino acids in the HA-treated animals. Levels of DID were undetectable (<1 pg/ml) in 8-week-old animals that were not exposed to either HA or smoke.

Lung DID

Figure 16:
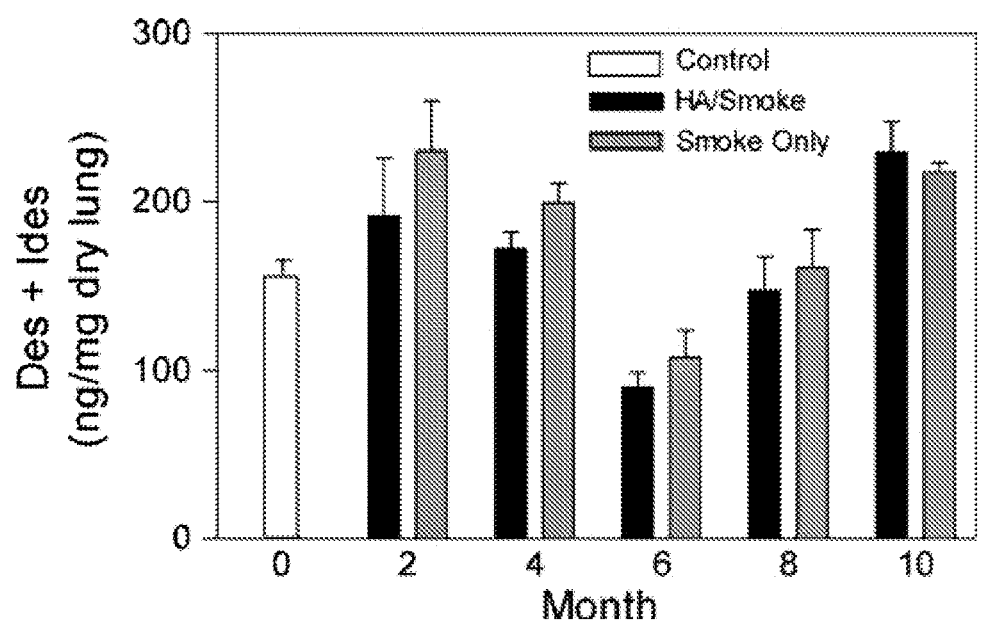
FIG. 16: An increase in lung DID was seen in both treatment groups during the first 2 months of smoke exposure, followed by a decrease over the next 4 months and a second increase between 6 and 10 months (n≥3 for each bar). Differences between the groups were not statistically significant over the 10-month period following initial smoke exposure.

The amount of DID in the lungs was also measured at bimonthly intervals, beginning 2 months after the smoking regimen began. Both the HA/Smoke and Smoke-Only groups showed an increase in DID during the first 2 months, followed by a decline over the next 4 months and a second increase between 6 and 10 months (FIG. 16).

Differences between the groups were not statistically significant over the entire course of the study.

Lung Histopathology

Figure 18:
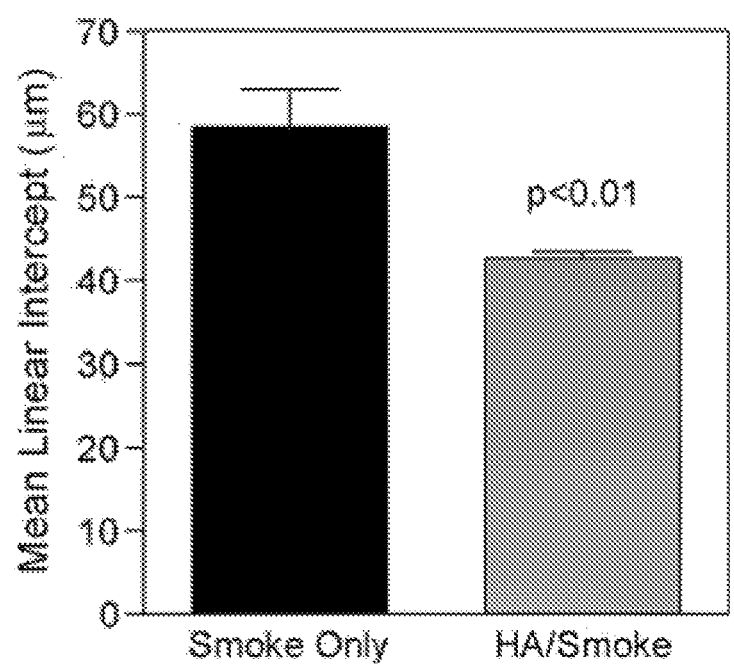
FIG. 18: After 3 months of smoke exposure, animals treated with HA showed a significant reduction in airspace enlargement compared to those receiving smoke alone (n=5 for each bar).

Exposure to tobacco smoke for 3 months resulted in significant airspace enlargement in animals receiving smoke alone, whereas only minimal alveolar changes were seen in those treated with HA (FIG. 17). The mean linear intercept (MLI) of animals treated with HA was 42.6 µm compared to 58.4 µm for those receiving smoke alone (p<0.01; FIG. 18). There was no significant difference between the MLI of the HA-treated group and that of 8-week-old control animals from our previous study (40.5±0.6 lm), which were not exposed to either smoke or HA[15]. However, animals receiving only smoke had a significantly higher MLI than this control group (p<0.01). Similar measurements were not performed at later time intervals because there was little progression of airspace enlargement in either group, which is consistent with previous morphological findings[15].

Figure 19A:
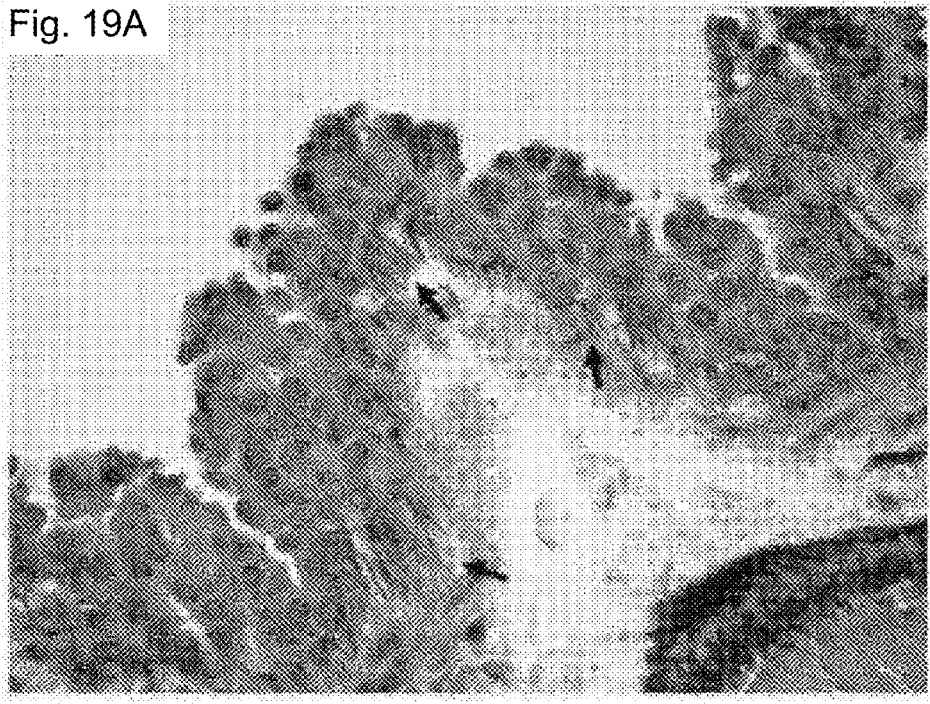
FIG. 19A: Photomicrograph of a mouse lung treated with HA and exposed to cigarette smoke for 3 months showing papillary hyperplasia of bronchial epithelium and proliferation of elastic fibers (arrows).
Figure 19B:
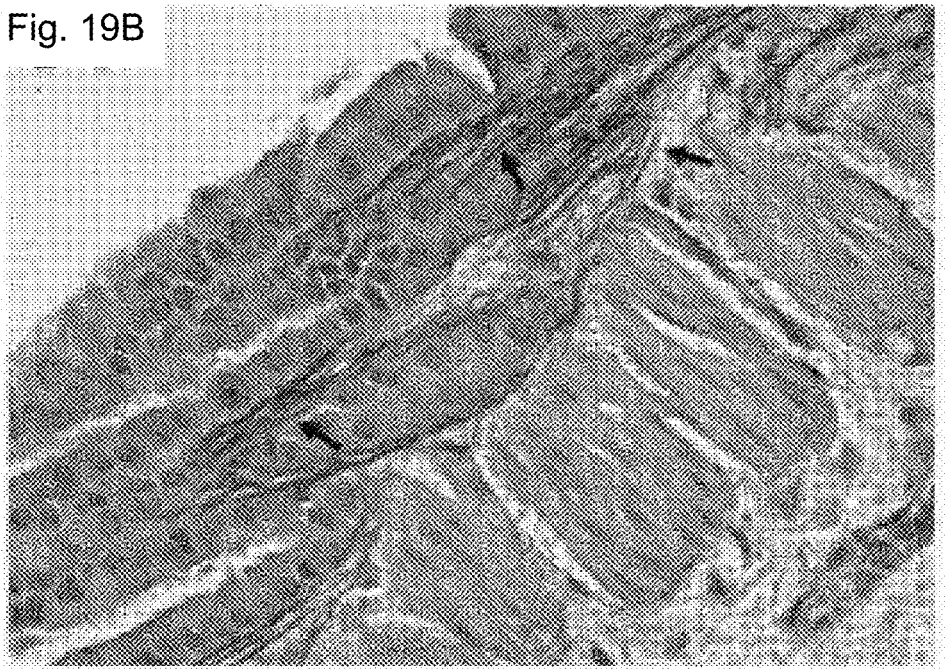
FIG. 19B: Similar histological changes were seen in lungs receiving smoke alone for the same period of time. Original magnification of both figures: 400× (Verhoef-Van Gieson).

Both groups showed inflammation of the larger airways at 3 months, including prominent papillary hyperplasia of bronchial epithelium, and accumulation of elastic fibers within the connective tissue stalks associated with the papillary epithelium (FIG. 19). The airway inflammation persisted at later time intervals (6 and 10 months), but there was no evidence of alveolitis or interstitial fibrosis in either group, despite the increase in total lung DID between these two time points. While several studies have shown that low-molecular-weight HA may enhance the expression of a variety of cytokines[17,18], we observed no evidence of an inflammatory response in the HA-treated animals beyond that induced by smoke exposure.

Discussion

The concept of using nebulized HA to prevent elastic fiber injury is based on a series of experiments designed to determine the potential role of agents other than elastases in the pathogenesis of pulmonary emphysema. Previous studies from this laboratory indicated that intratracheal instillation of a nonelastolytic enzyme, hyaluronidase, induced pulmonary airspace enlargement in hamsters when administered in conjunction with 60% oxygen[19]. Damage to elastic fibers occurred only when both agents were given concomitantly, suggesting the possibility that hyaluronidase may facilitate the breakdown of these fibers by increasing their susceptibility to injury by other injurious agents such as elastases or oxidants. This concept was supported by subsequent work demonstrating that pretreatment of the lung with hyaluronidase enhances airspace enlargement induced by intratracheal administration of elastase[20,21].

Studies were then undertaken to examine the effect of HA itself on this model of emphysema. Animals were exposed to an aerosol composed of 0.1% HA in water for 50 min prior to intratracheal instillation of elastase. Compared to controls treated with aerosolized water and elastase, those that received HA had significantly less airspace enlargement[22,23].

Although the precise mechanism by which HA prevents lung injury is not yet well understood, our laboratory has shown that HA does not directly inhibit elastases but instead appears to bind to elastic fibers and prevent elastases from attacking them[20,22,24]. Studies using aerosolized fluorescein-labeled HA demonstrated preferential adherence of the polysaccharide to lung elastic fibers[22,24]. This finding was complemented by additional experiments in which the binding of HA to elastic fibers in vitro prevented elastolysis by several different types of elastase, including human metalloproteinase 12, an enzyme that may be responsible for emphysematous changes associated with cigarette smoking[22].

Interactions between HA and elastic fibers may involve formation of electrostatic or hydrogen bonds. The binding sites may not be situated on the elastin protein itself but may instead be located in the surrounding matrix composed of microfibrils or other glycoproteins. Alternatively, the exogenously administered HA could combine with native HA in close proximity to elastic fibers by a process of self-aggregation[26,27]. The resulting molecular complexes of HA may provide a protective barrier against both free elastases and the cells that secrete them[13].

In contrast to earlier studies in which HA was administered concomitantly with cigarette smoke, the current investigation allowed elastic fiber breakdown to proceed unimpeded for the first month, thus providing a more clinically relevant test of the therapeutic potential of HA. While concurrent administration of aerosolized HA significantly reduced BALF DID levels within 3 months of smoke exposure[15], the same effect was not seen until 6 months in the present study. Nevertheless, the delay in administering HA did not affect its ability to prevent emphysematous changes in the lung.

In the current study, the lack of airspace enlargement in the HA-treated group, despite significant elastic fiber breakdown, may possibly be explained by the fact that airway injury is an early feature of this model of smoke-induced lung injury. Although the precise contribution of airway inflammation to BALF DID levels remains uncertain, it may be speculated that the high levels of BALF DID at 2 and 4 months following initiation of smoke exposure are a consequence of elastin turnover in the walls of the larger airways rather than the distal lung.

With regard to total-lung DID, there were no significant differences between the two groups at any time point, suggesting that this parameter is not a sensitive measure of elastic fiber degradation but rather reflects the balance between elastic fiber injury and repair. Rapid resynthesis of these fibers could mask any differences with regard to their rate of breakdown.

The development of airway inflammation within the first 2 months of smoke exposure may explain why HA was initially ineffective in reducing BALF DID levels. The release of enzymes and oxidants by inflammatory cells may cause the exogenous HA to undergo breakdown, thereby impairing its ability to form larger, protective complexes in proximity to airway elastic fibers. While such a process remains hypothetical, this laboratory has previously shown that the same preparation of aerosolized HA used in the current study is effective in preventing acute lung injury only when given prior to intratracheal instillation of endotoxin[27].

Whether a similar pattern of elastic fiber breakdown and proliferation occurs in human lungs in response to smoking remains unclear. However, there is some experimental evidence which suggests that both forms of injury have certain features in common. In one study, DID levels in plasma and urine were significantly elevated in COPD patients, with and without emphysema, indicating that elastic fiber injury occurs in both airways and lung parenchyma[12]. Other investigators have also reported a reduction in urinary desmosine levels as the disease progresses, although their findings were attributed to a loss of lung elastic fiber mass rather than a specific decrease in the rate of elastin breakdown[28].

The leveling off of airspace enlargement in smoke-exposed mice after several months is consistent with an adaptive response to chronic injury. A number of studies suggest that enhanced synthesis of endogenous antioxidants may limit the damaging effects of tobacco smoke and other oxidants[29-31]. Furthermore, changes in the interstitial extracellular matrix resulting from continued injury and repair could decrease the likelihood of alveolar wall rupture due to elastase activity or mechanical stress. Regarding this possibility, an increase in lung collagen content has been reported after prolonged exposure to cigarette smoke, suggesting a transition from a degradative to a proliferative process, similar to that observed in the current study[32].

Notwithstanding these limitations, experimental models of smoke-induced lung injury provide a means of evaluating the usefulness of potential therapeutic agents. In the current study, the ability of HA to mitigate both airspace enlargement and elastic fiber injury, despite a 1-month delay in treatment, provides added support for testing this agent in patients with pre-existing COPD. The gradual progression of this disease suggests that even a small decrease in the rate of elastic fiber injury could have a significant impact on the decline of lung function.

Example 5—Quantitation of Desmosine and Isodesmosine in Urine, Plasma, and Sputum by Tandem Mass Spectrometric Analysis In this application we describe a practical, and a reliable LC/MSMS analysis that can measure DES and IDS in all body fluids including urine, plasma, sputum, and lavages and serve as a standardized method. The analysis utilizes commercially available acetylated pyridinoline as the internal standard to optimize reproducibility and accuracy.

Materials and Methods
Chemicals

Desmosine (DES) and Isodesmosine (IDS) standard (mixed 50% DES and 50% IDS) were purchased from Elastin Products Company (Owensville, Mich.). Acetylated pyridinoline was obtained from Quidel (San Diego, Calif.). CF1 cellulose powders were purchased from Whatman (Clifton, N.J.), and all other reagents were from Sigma (St. Louis, Mo.).

Sample Collection and Human Subjects

Urine (24 hour samples), plasma, and sputum samples were collected as previously described[11,54] from volunteers with informed consent at the James P. Mara Center for Lung Disease, St. Luke/Roosevelt Hospital Center, New York. COPD was diagnosed in study patients according to the Global initiative for Chronic Obstructive Lung Disease grades 1 to 4[60]. Patients gave informed consent for the study. Control subjects were selected by clinical history free of any specific known disease or significant symptoms, and none have ever smoked. The study was approved by the Institutional Review Board.

Creatinine and Protein Measurement

Urine creatinine was measured by the commercially available 555A creatinine kit (Sigma-Aldrich). Total protein in plasma and sputum samples was measured by the commercially available microprotein assay kit (Sigma-Aldrich), which is based on protein-dye (Coomassie blue) binding.

Acid Hydrolysis

Samples of urine (0.1 ml), plasma or sputum (0.5 ml each) were placed in a glass vial with equal volumes of conc. HCl (37%). Air in the vial was displaced with nitrogen, and was heated at 110° C. for 24 hrs. The hydrolyzed sample was filtered and evaporated to dryness. For the free (unconjugated) forms of DES and IDS analysis, 0.2 ml of urine was analyzed directly without the HCl hydrolysis.

Cellulose (CF1) Cartridge Extraction

The acid hydrolyzed samples (after drying under vacuum or nitrogen stream to remove residual acid) or unhydrolyzed urine sample (for free DES and IDS analysis) were treated with 1 ng (for urine samples) or 0.5 ng (for plasma and sputum samples) of acetylated pyridinoline as the internal standard.

The mixture was dissolved in 2 ml of n-butanol/acetic acid/water (4:1:1), and applied onto a 3 ml cellulose cartridge, which was prepared by introduction of 3 ml of 5% CF1 cellulose powder slurry in n-butanol/acetic acid/water (4:1:1). The cellulose powder slurry must be a well dispersed slurry by stirring for 24 hrs. The cartridge was washed 3 times with 3 ml of n-butanol/acetic acid/water (4:1:1), and the samples retained in the cartridge were eluted with 3 ml of water, dried and dissolved in 200 µl (for urine sample) or 100 µl (for plasma and urine samples) of LC mobile phase and analyzed by LC/MSMS.

LC/MSMS Analysis

A TSQ Discovery electrospray tandem mass spectrometer (Thermo Fisher Scientific) was used for LC/MSMS analysis. HPLC conditions used were a 2 mm×150 mm dC18 (3 µm) column (Waters, Mass.) and the mobile phase A (7 mM HFBA/5 mM $NH_4Ac$ in water) and B (7 mM HFBA/5 mM $NH_4Ac$ in 80% acetonitrile) were programmed linearly from 100% A to 82% A in 12 mins.

Quantitation was performed by selected reaction monitoring (SRM) of the transitions of both DES and IDS (m/z 526 to m/z 481+m/z 397) and the internal standard (m/z 471 to m/z 128), with collision energy set at 33 V for both transition, collision gas pressure was 1.5 mTorr, tube lens at 132 V, with sheath gas pressure set at 45 and auxiliary gas pressure at 6 units and ion spray voltage at 3.8 kV. The scan time set at 1.00 msec and both quadrupoles (Q1 and Q3) were at 0.7 Da FWHM.

Statistical Analysis

A t-test adjusted for unequal variance was used to test the null hypothesis. The level of significance was 0.05. The p-values were calculated based on the summed values of DES and IDS using the unpaired t-test (The used software is "GraphPad Prism 4 (2)").

Results

DES and IDS are Stable Toward HCl Hydrolysis

The assay of total DES and IDS in biological fluids requires HCl hydrolysis at 110° C. to release DES and IDS from their crosslinked or peptide conjugates. We examined the stability of DES and IDS in three different concentrations (10, 5, and 1 ng/ml) during HCl hydrolysis at 110° C. for 24 hrs. The DES/IDS solutions resulting from the HCl treatment were subjected to LC/MSMS measurements of DES and IDS, which were compared with the measurements of the same concentrations of untreated DES and IDS to calculate the recovery by the acid treatment. The results show that DES and IDS are stable through acid hydrolysis with virtually complete recoveries at all three concentrations (Table 3).

Recovery of DES and IDS in Human Body Fluids

Three known amounts of DES/IDS were spiked into the control urine, plasma, and sputum samples at concentration ranges expected to be encountered in biological samples (10, 20 and 40 ng/ml in urine samples; 0.2, 0.4 and 0.8 ng/ml in plasma and sputum samples). The mixtures were subject to HCl hydrolysis at 110° C. for 24 hrs, addition of IS, CF1 cartridge chromatography, and LC/MSMS analysis under the established procedure to measure DES/IDS levels. The recoveries of DES/IDS are above 99% in urine, 94% in plasma, and 87% in sputum samples; with the imprecision 8%, 9%, and 10%, respectively (Table 2). Limit of quantitation (LOQ) in all relevant body fluids are determined as 0.1 ng/ml of samples based on reproducibility and recovery study (Table 4).

Acetylated Pyridinoline as Internal Standard

Acetylated pyridinoline is an acetylated derivative of 3-hydroxy pyridinoline which serves as a trifunctional crosslink in collagen. The compound has been used as an internal standard (IS) in HPLC analysis of pyridinium crosslinks of collagen in urine or tissue[61-63].

Figure 11:
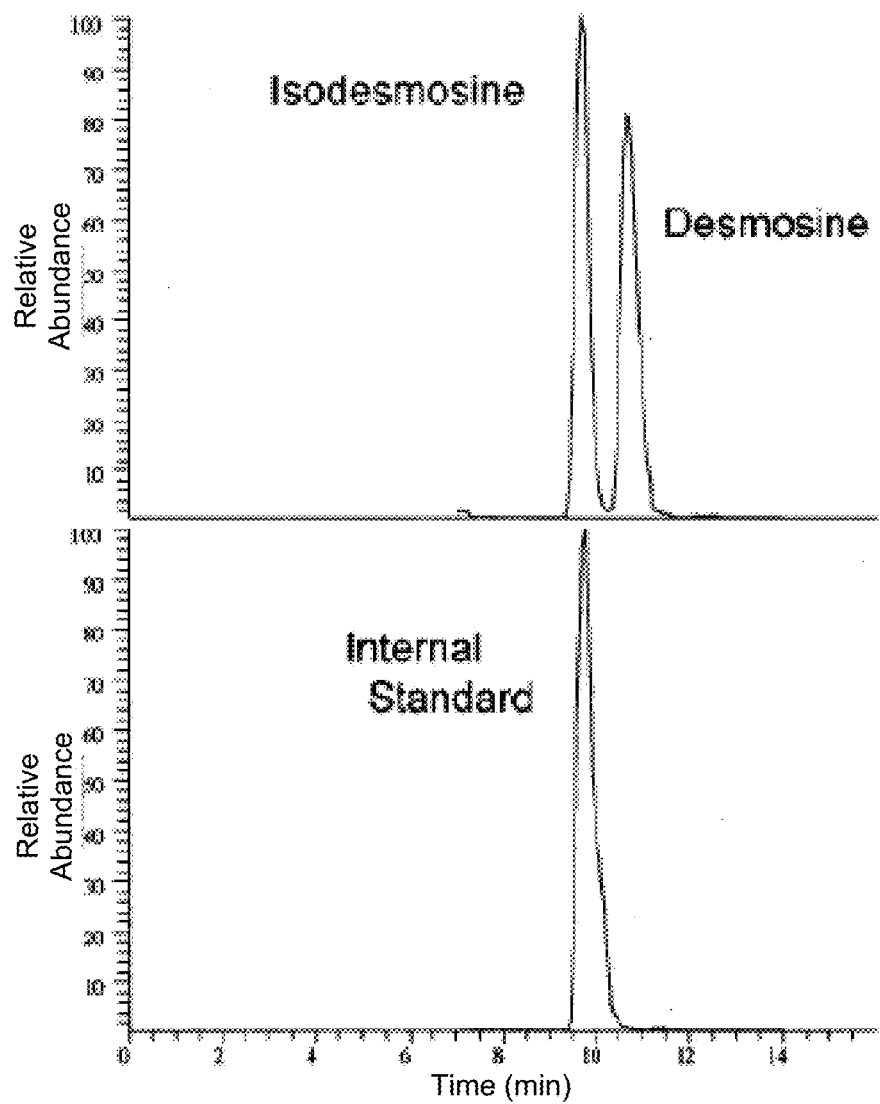
FIG. 11: Shown in FIG. 11 are peaks of D and I standards in the top panel, as obtained from LC/MSMS analysis. The peak for acetylated pyridinoline (IS), is shown in the lower panel. Chromatographic peak areas under the curves of the standards are used in the calculation of D and I concentrations in samples.
Figure 12:
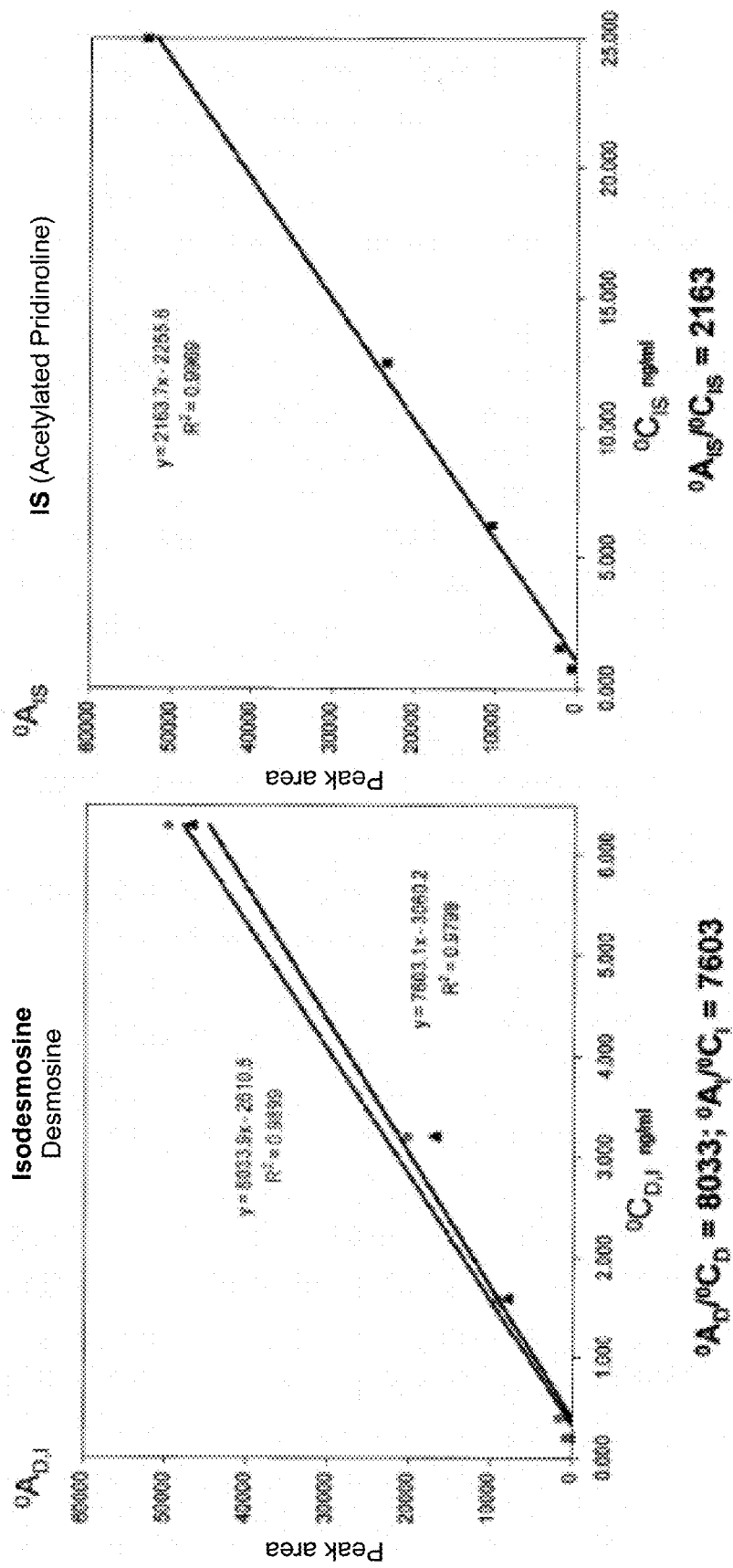
FIG. 12: Shown in FIG. 12 are calibration curves for D, I and IS after CF-1 treatment. The left panel shows the calibration curves for D and I. The right panel shows the calibration curve for IS.
Figure 14A:
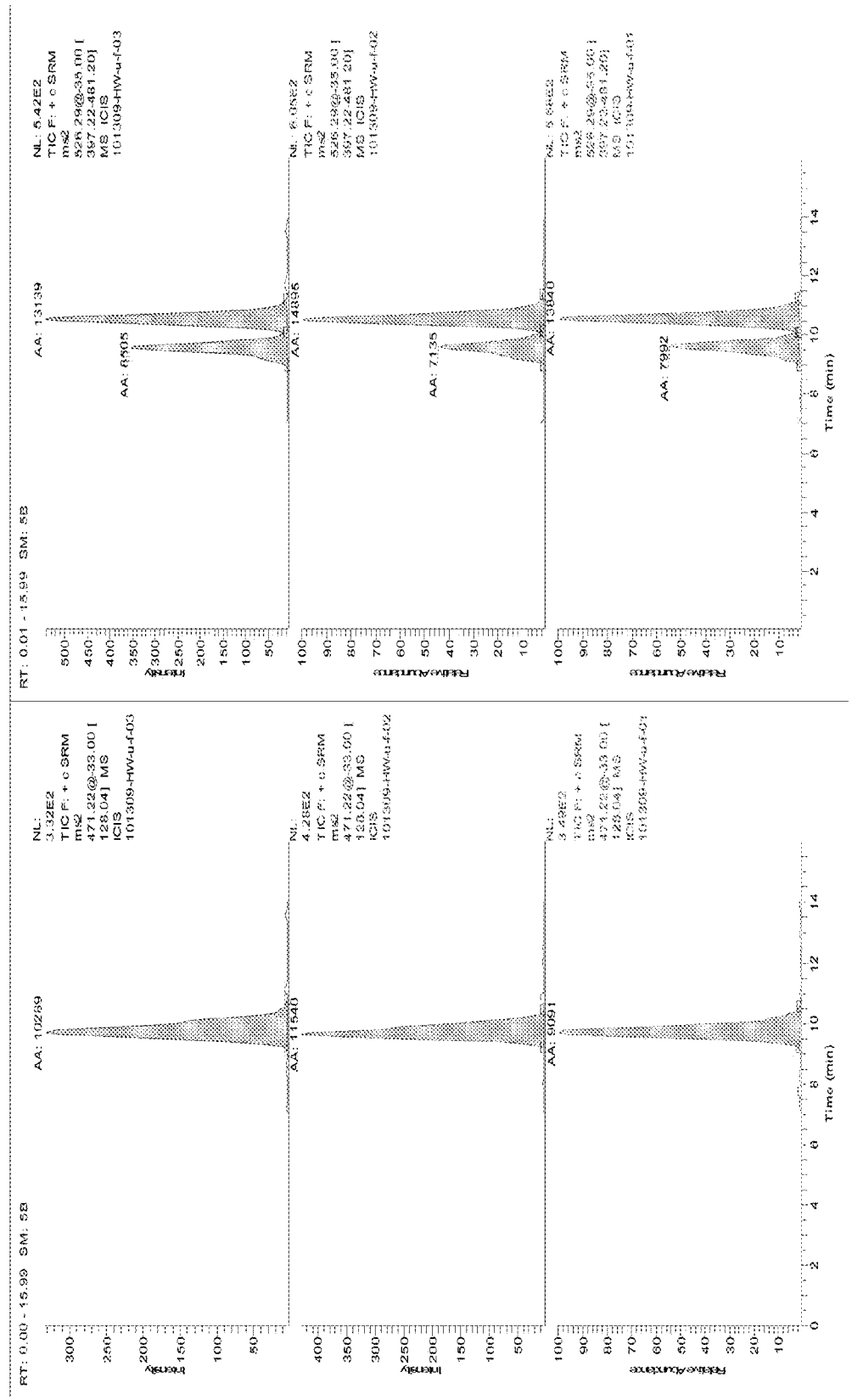
FIGS. 14A-14D: Shown are spectrograms for samples from a patient of urine (free D and I) (FIG. 14A), urine (total D and I) (FIG. 14B), plasma (FIG. 14C) and sputum (FIG. 14D), wherein each sample was tested three times. The left panel of each shows the spectrogram for IS and the right panel of each shows the spectrograms in which D and I are resolved from the sample.
Figure 14B:
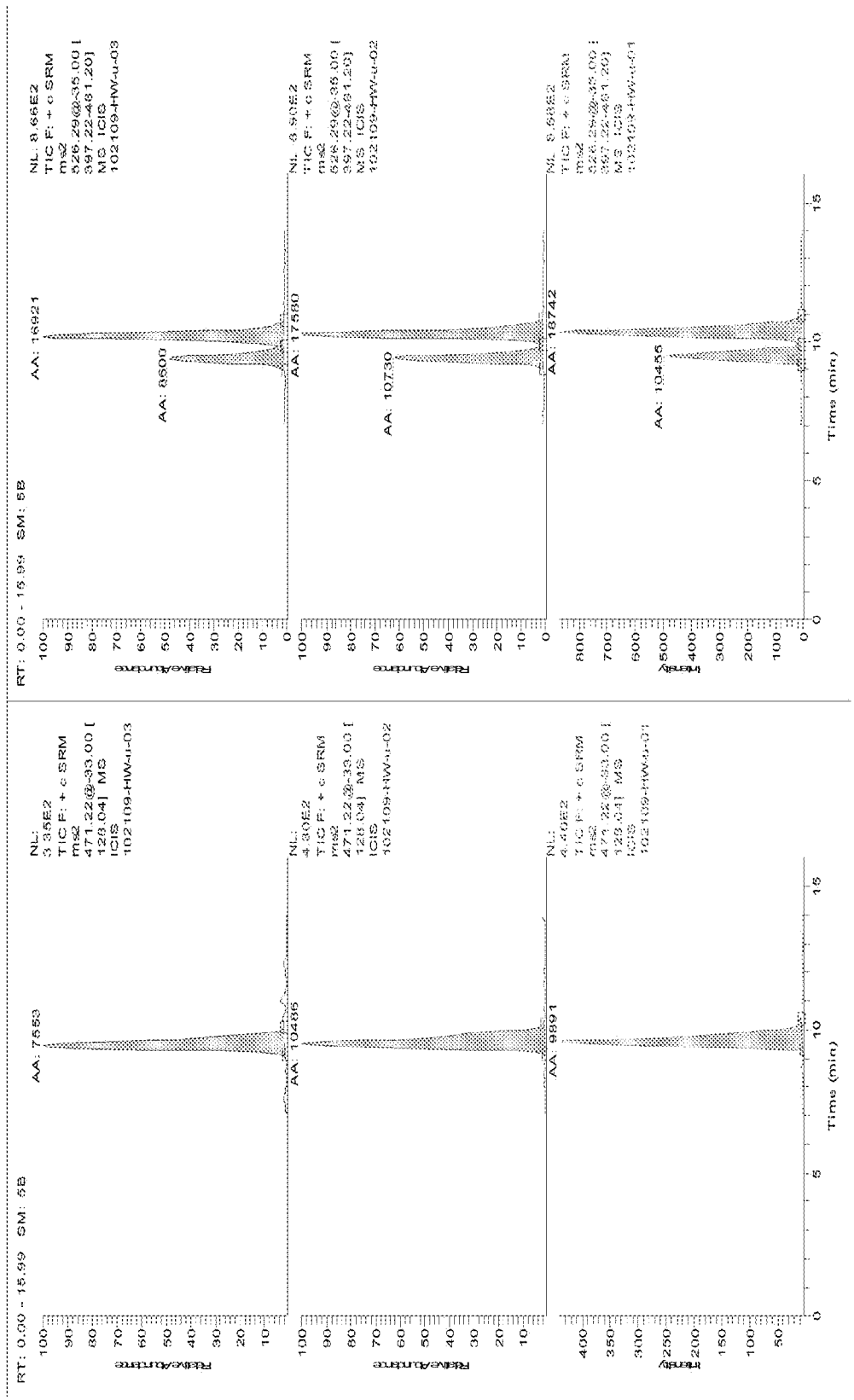
Figure 14C:
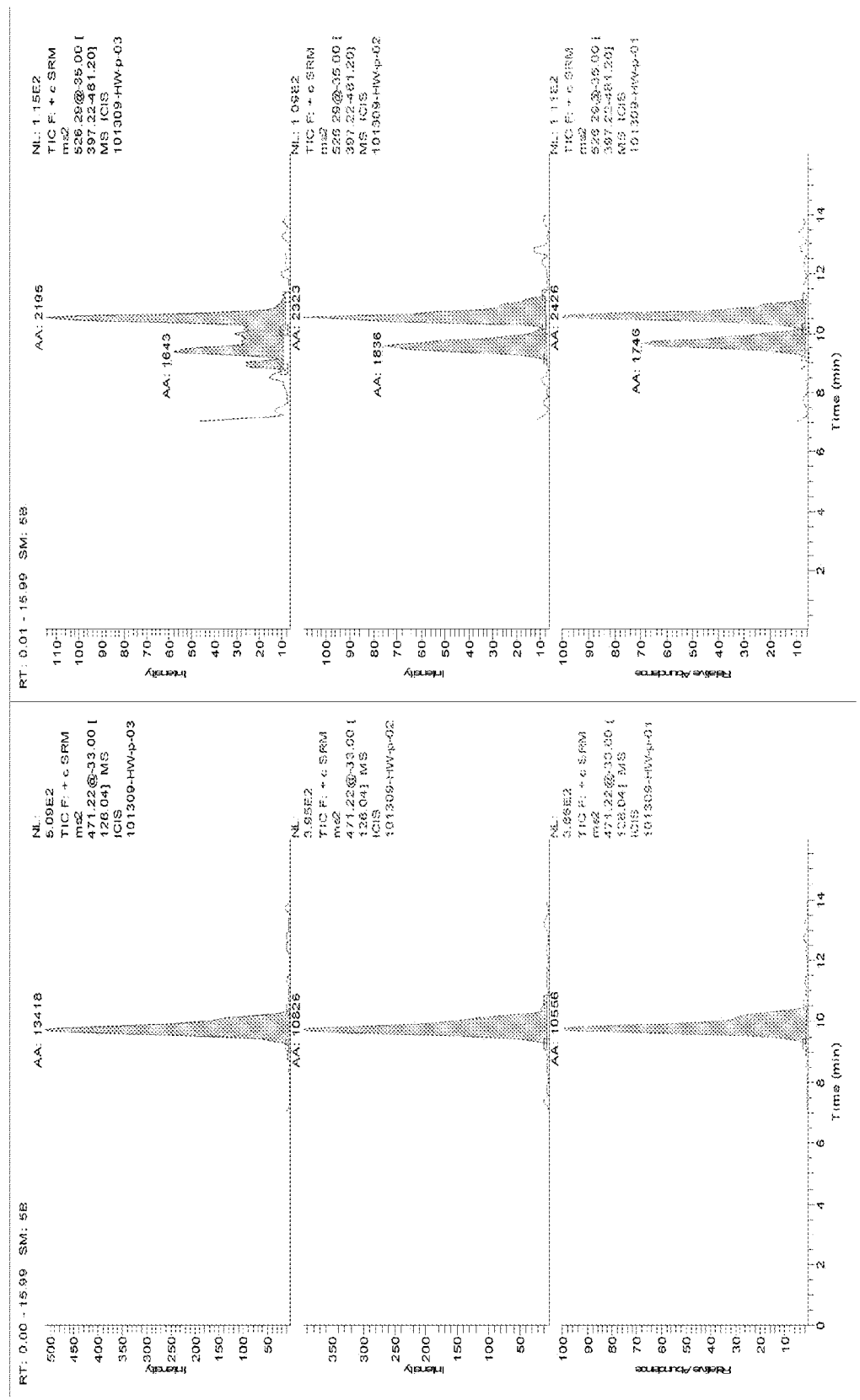
Figure 14D:
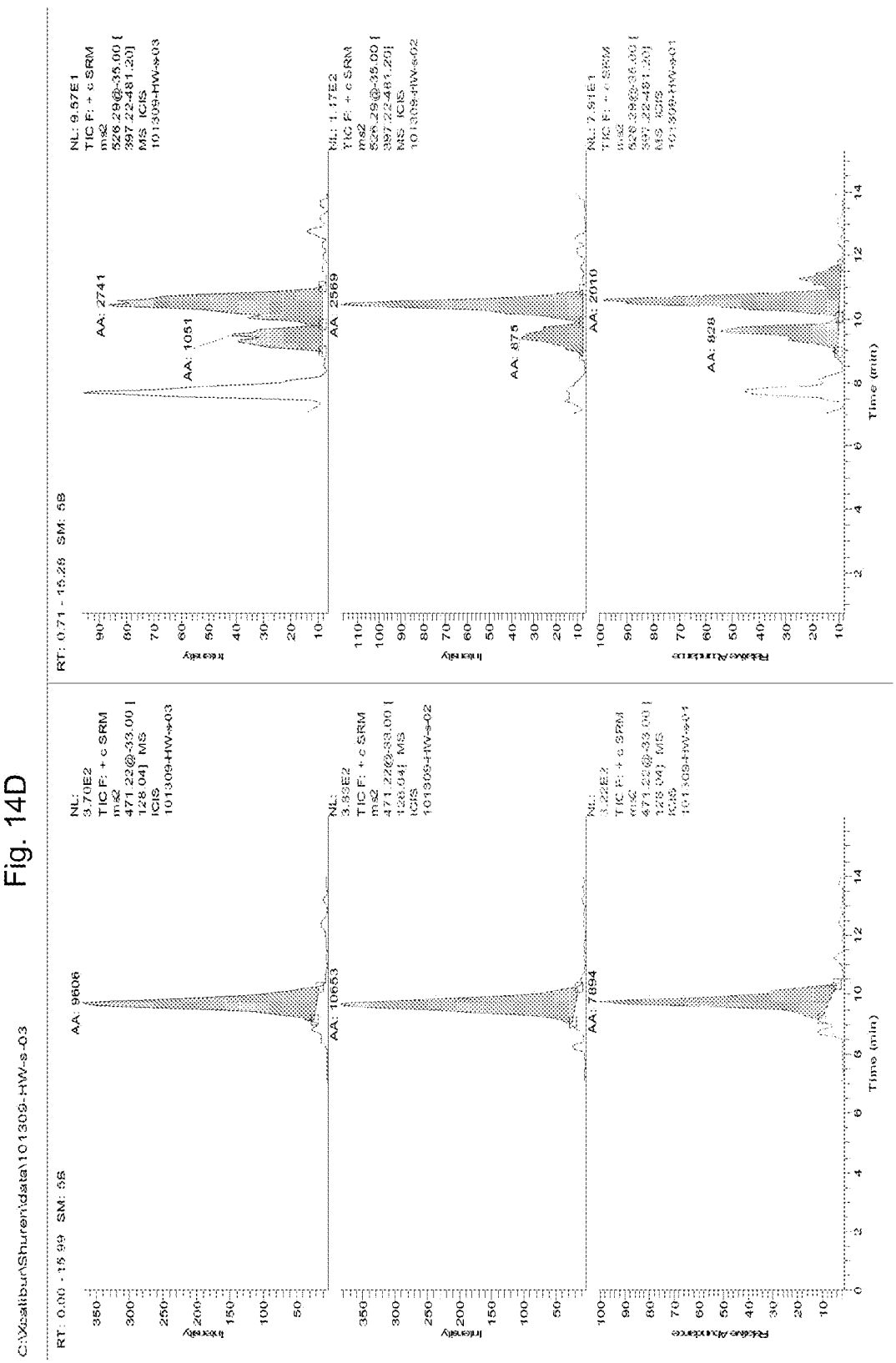
Figure 20B:
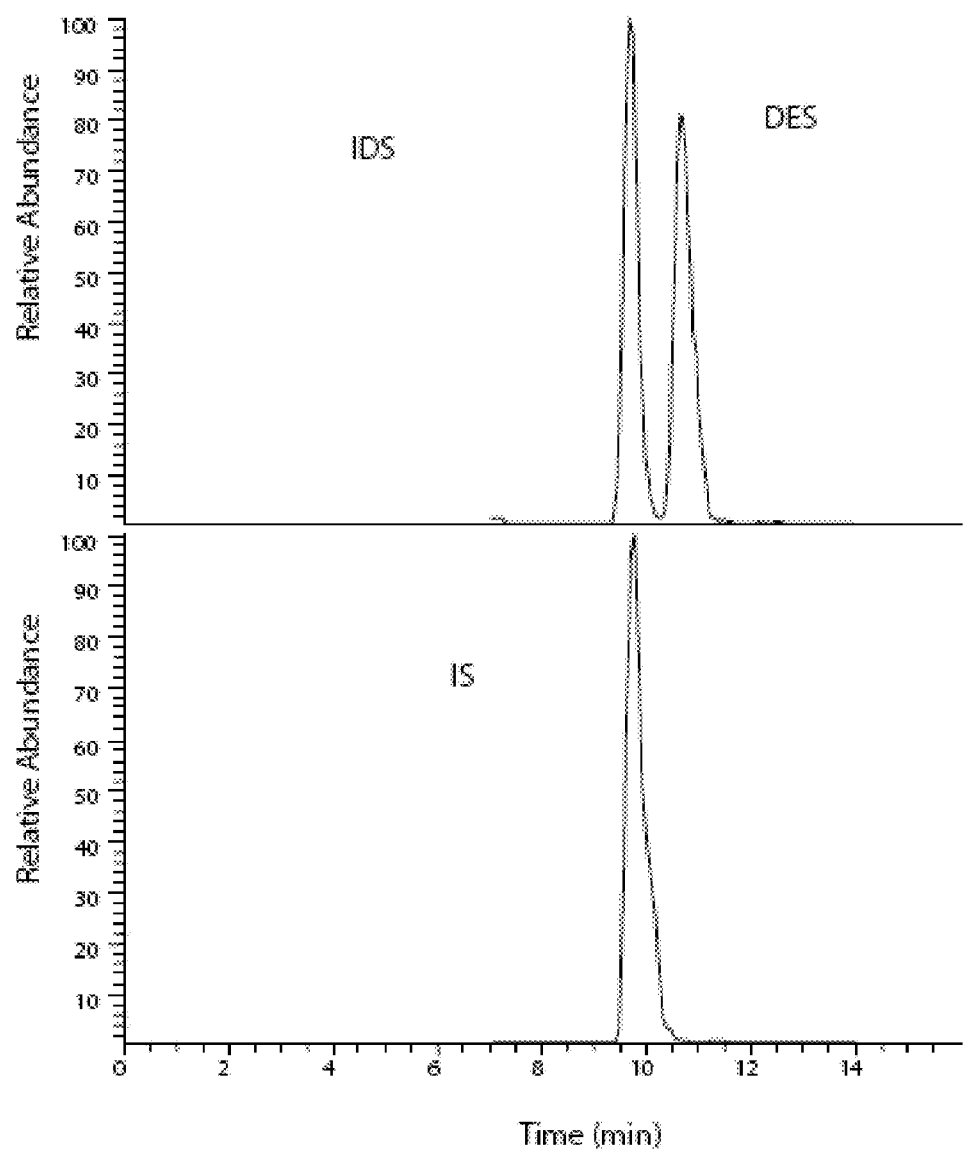
FIG. 20B: LC/MSMS chromatogram of DES, IDS, and IS.
Figure 21A:
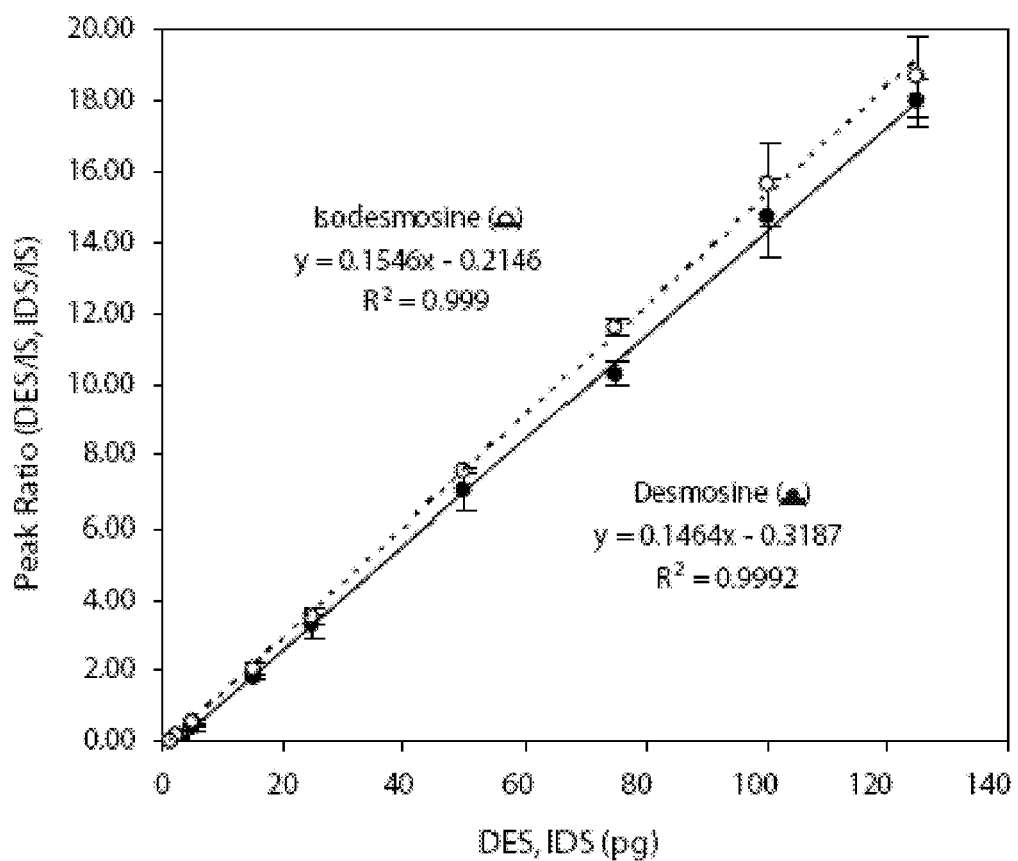
FIG. 21A: Linearity response of DES and IDS analysis. Different concentrations of DES/IDS (1.25-125 pg) were added with 50.0 pg of IS, absorbed on CF1 cartridge columns, washed and eluted DES/IDS were quantitated separately.
Figure 21B:
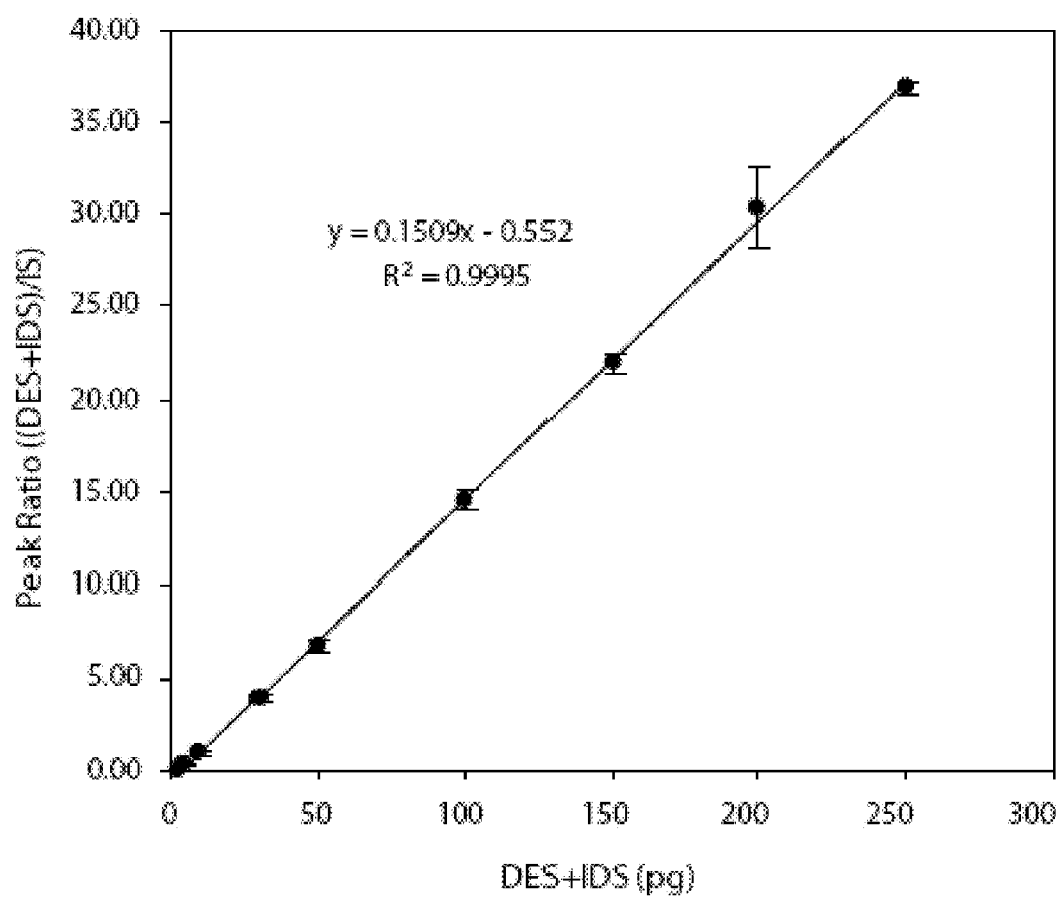
FIG. 21B: Same as FIG. 21A, but DES+IDS were quantitated.

Since acetylated pyridinoline has a similar molecular structure and polarity to that of DES and IDS (FIG. 20A), the use of the pyridinoline as an IS for the LC/MSMS analysis of DES and IDS was explored. The elution characteristics of acetyl pyridinoline in both a CF1 cartridge and HPLC column are closely similar to DES and IDS (FIGS. 11 and 20B). It also exhibits a similar linear response in mass spectrometric analysis. Since DES and IDS have been found stable without losses through HCl hydrolysis, we introduce acetylated pyridinoline as IS after the HCl hydrolysis for the DES and IDS quantitation to determine recovery from the subsequent analytical procedure. The linear responses of DES and IDS using acetylated pyridinoline as the IS for the analytical procedure are shown in FIGS. 21A-B. As also shown in FIG. 12 and Example 3, our HPLC chromatography can effectively separate the two DES and IDS isomers; thus, the isomers can be conveniently quantified separately using the calibration curve of FIG. 21A or as DES+IDS using the calibration curve of FIG. 21B.

Standardized LC/MSMS Analysis of DES and IDS in all Body Fluids

We have developed the following conventional three-step analytical procedure which can be used to measure DES and IDS in all relevant body fluids (urine, plasma, and sputum) or lavage fluids:

1. Sample hydrolysis: To body fluid samples (0.1 ml urine, 0.5 ml plasma or sputum) are added with equal volumes of concentrated HCl (e.g., about 6-12N) and heated in nitrogen at 110° C. for 24 hours. (For free urinary DES and IDS analysis, this hydrolysis step is eliminated)

2. CF1 cartridge extraction: Add 1 ng (for urine) or 0.5 ng (for plasma, sputum) of internal standard (acetylated pyridinoline) and apply to a 3 ml cellulose cartridge prepared by introduction of 5% CF1 cellulose powder slurry in n-butanol/acetic acid/water (4:1:1), wash the cartridge with n-butanol/acetic acid/water (4:1:1), and elute the analytes out with 3 ml of water.

3. LC/MSMS analysis: HPLC separation by a 2 mm×150 mm dC18 (3 μm) column and measure DES and IDS by SRM monitoring of transition ions; DES or IDS (m/z 526 to m/z 481+397) and IS (m/z 471 to m/z 128).

Figure 22A:
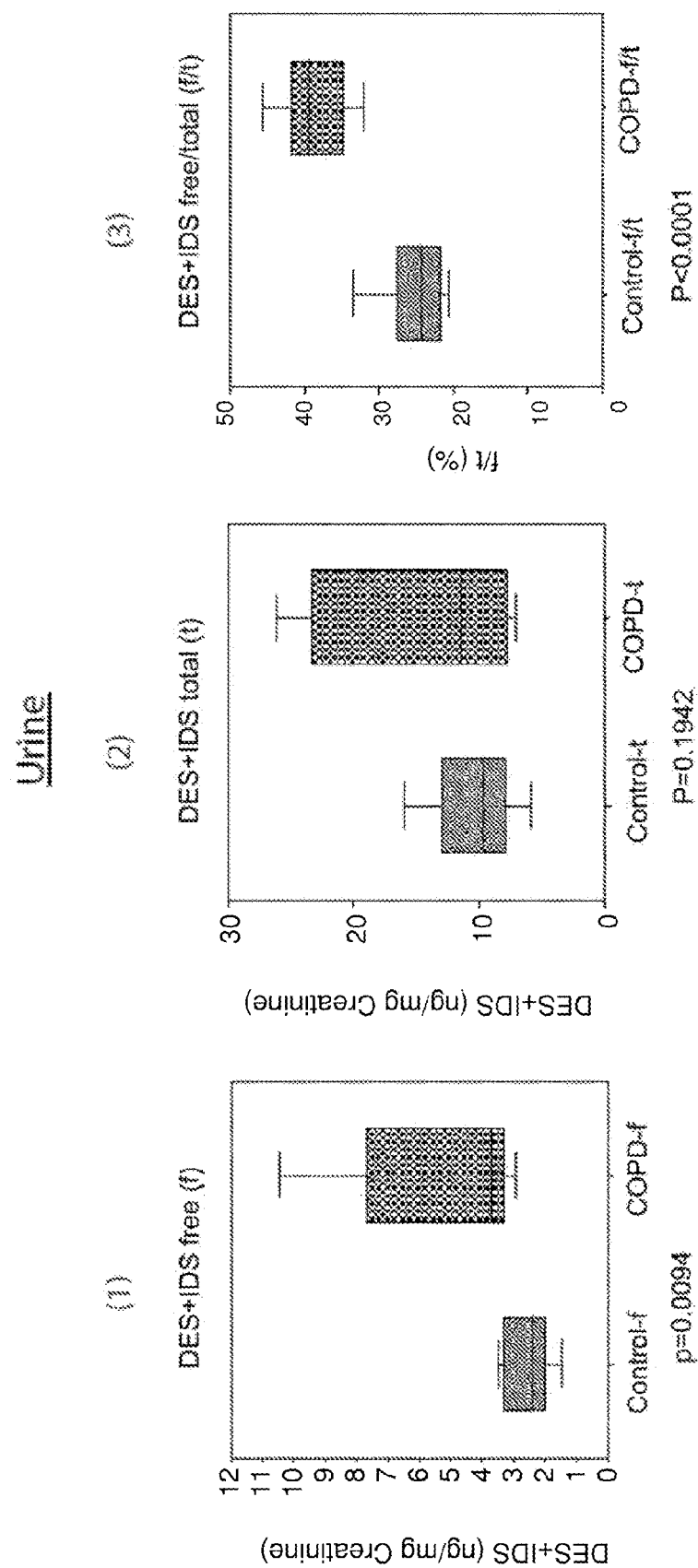
FIGS. 22A-22C: DES/IDS levels in COPD patients and healthy controls: The boundaries of the box indicate between the 25th to 75th percentile, and the line within the box is the median.
Figure 22B:
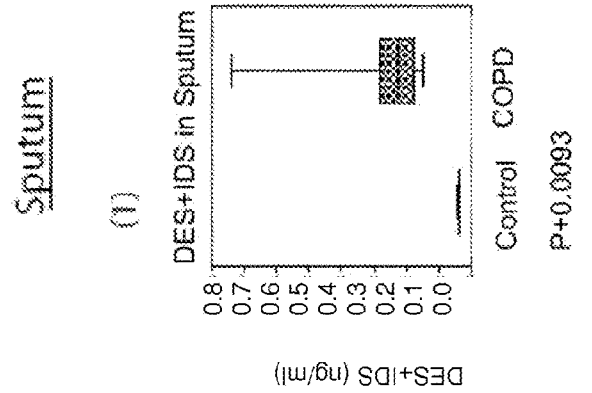
Figure 22C:
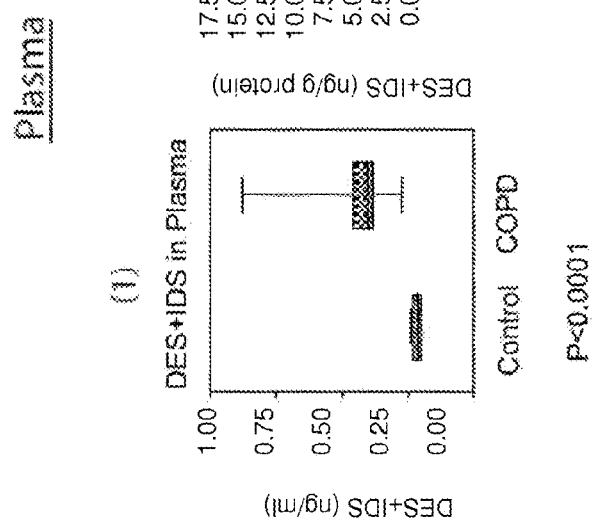

Measurement of DES and IDS in Urine, Plasma, and Sputum of COPD Patients and Healthy Subjects The analytical procedure we have developed was used to compare the levels of DES and IDS in urine, plasma, and sputum obtained from COPD patients and that of healthy normals. The results are shown with urine samples in FIG. 22A, plasma samples in FIG. 22B, and sputum samples in FIG. 22C. The urinary DES/IDS levels after HCl hydrolysis (total DES/IDS) in COPD patients are slightly higher than that of healthy controls, but the difference is not statistically significant (p=0.1942). On the other hand, the urinary DES/IDS levels without HCl hydrolysis (free DES/IDS) in COPD patients are statistically significantly higher than that of healthy controls (p=0.0094). The ratios of free DES/IDS to total DES/IDS are significantly higher in COPD patients than that of controls (p<0.0001) (FIG. 22A). This result is in agreement to our previous data (23,24). Also the data indicates that the ratio of total DES/IDS to free DES/IDS levels in urine samples are good biomarkers for showing increased elastase activity in COPD patients. In plasma, DES/IDS levels in COPD patients are statistically higher than that of the healthy controls (p<0.0001) (FIG. 22B). The DES/IDS in sputum of COPD patients shows the median of 0.24 ng/ml, while the levels in induced sputum from healthy subjects are below detection limit (0.04 ng/ml) (FIG. 22C).

Discussion

A strength of DES/IDS as biomarkers in COPD is the recognition that matrix elastin is a structural target of the disease. Among the many techniques developed to measure DES/IDS, the LC/MSMS technique which provides higher sensitivity and specificity appears to be an improved choice for biomarker analysis[55]. Several modifications of LC/MSMS methods for DES/IDS analysis have been reported recently, but they are all developed for the measurements of DES/IDS in urine[56-58]. Our previous studies on the measurement of DES/IDS in COPD patients[11,54] and DES/IDS levels in response to Tiotropium treatment of COPD patients[10] demonstrate that DES/IDS levels in sputum and plasma are effective indicators of elastin degradation in patients in the body as a whole and the lung per se. Development of a sensitive, accurate, and reproducible method which can measure DES/IDS levels in all body fluids can be clinically meaningful especially related to parameters such as lung structure analyzed by computed tomography quantitative, lung function or genomic analysis.

Previously published LC/MS or LC/MSMS methods[11,54-58] all have disadvantages of either lack of a reliable internal standard or the method not standardized for the analysis of all relevant body fluids (i.e., urine, plasma, and sputum), which are important for assessing clinical meaning of elastin degradation. In this application we have developed a practical and simplified LC/MSMS analytical procedure that can be universally utilized for the analysis of DES and IDS in all relevant body fluids; including urine, plasma, and sputum.

We confirm that DES/IDS are stable under the conditions of hydrolysis in 6N HCl at 110° C. for 24 hours, the acid hydrolysis generally used to release DES/IDS from their peptide conjugate (Table 3). We introduce acetylated pyridinoline as the internal standard after the HCl hydrolysis step to correct for losses occurring from the subsequent steps. Acetylated pyridinoline has a closely similar molecular structure and chromatographic mobility to that of DES and IDS molecules, which enables the development of a reproducible and accurate LC/MSMS measurement of DES/IDS in urine, plasma, and sputum. The LC/MSMS analysis can also effectively separate the two DES/IDS isomers (FIG. 20B), thus two DES/IDS isomers can be conveniently quantified either separately (FIG. 21A) or as combined DES+IDS (FIG. 21B) in all body fluids.

The structures and the stability of the introduced standard were not demonstrated. In this regard, acetylated pyridinoline is a commercially available compound with defined structure, which can be readily added as the internal standard. The accuracy and reproducibility of the developed LC/MSMS analysis was further tested by recovery studies of

TABLE 3

Stability of Desmosine (DES) and Isodesmosine (IDS) on acid hydrolysis*

| Recovered (ng/ml) | 10 ng/ml DES/IDS | | | 5 ng/ml DES/IDS | | | 1 ng/ml DES/IDS | | |
|---|---|---|---|---|---|---|---|---|---|
| | DES | IDS | DES/IDS | DES | IDS | DES/IDS | DES | IDS | DES/IDS |
| Means | 5.04 | 5.37 | 10.41 | 2.42 | 2.55 | 4.98 | 0.50 | 0.48 | 0.98 |
| SD | 0.32 | 0.30 | 0.61 | 0.20 | 0.20 | 0.24 | 0.05 | 0.05 | 0.10 |
| % | 6 | 5 | 6 | 8 | 8 | 5 | 10 | 11 | 10 |
| % Recovery | 101 | 107 | 104 | 97 | 102 | 100 | 100 | 96 | 98 |

*DES/IDS of three concentrations were hydrolyzed in 6N HCl at 110° C. for 24 hour, after addition of internal standard DES/IDS were re-isolated by SPE (CF1 column) chromatography, and quantified by LC/MSMS analysis Two previous reports have introduced deuterated compounds as internal standards to improve LC/MSMS analysis of DES/IDS[57,58]. However the origin of the deuterium compounds are not stated, and appeared to be obtained through catalytic proton exchange reactions with DES/IDS. DES/IDS in a series of known contents of DES/IDS in urine, plasma, and sputum samples as shown in Table 4. The recoveries from urine, plasma, and sputum samples are above 99%, 94%, and 87%, respectively, with good reproducibility.

TABLE 4

Recovery of Desmosine (DES) and Isodesmosine (IDS) from Urine, Plasma, and Sputum*

| Recovery from Urine | Control Urine | | | Add 40 ng/ml urine | | | Add 20 ng/ml Urine | | | Add 10 ng/ml Urine | | |
|---|---|---|---|---|---|---|---|---|---|---|---|---|
| Recovered (ng/ml) | DES | IDS | DES/IDS | DES | IDS | DES/IDS | DES | IDS | DES/IDS | DES | IDS | DES/IDS |
| Mean(n = 3) | 3.82 | 3.24 | 7.06 | 23.3 | 23.33 | 46.65 | 14.14 | 14.36 | 28.5 | 8.81 | 8.2 | 17.01 |
| ±SD | 0.29 | 0.66 | 0.94 | 1.87 | 2.01 | 3.86 | 0.41 | 2.06 | 2.44 | 0.87 | 0.75 | 1.61 |
| % CV | 8 | 20 | 13 | 8 | 9 | 8 | 3 | 14 | 9 | 10 | 9 | 9 |
| % Recovery*2 | | | | 98 | 100 | 99 | 102 | 109 | 105 | 100 | 100 | 100 |

| Recovery from Plasma | Control Plasma | | | Add 0.8 ng/ml plasma | | | Add 0.4 ng/ml plasma | | | Add 0.2 ng/ml plasma | | |
|---|---|---|---|---|---|---|---|---|---|---|---|---|
| Recovered (ng/ml) | DES | IDS | DES/IDS | DES | IDS | DES/IDS | DES | IDS | DES/IDS | DES | IDS | DES/IDS |
| Mean(n = 3) | 0.23 | 0.13 | 0.35 | 0.57 | 0.57 | 1.15 | 0.4 | 0.33 | 0.72 | 0.31 | 0.22 | 0.52 |
| ±SD | 0.02 | 0.03 | 0.04 | 0.02 | 0.03 | 0.05 | 0.02 | 0.04 | 0.03 | 0.05 | 0.03 | 0.05 |
| % CV | 7 | 22 | 12 | 4 | 6 | 4 | 4 | 12 | 4 | 15 | 12 | 10 |
| % Recovery*2 | | | | 91 | 109 | 99 | 93 | 100 | 96 | 94 | 95 | 94 |

| Recovery from Sputum | Control Sputum | | | Add 0.8 ng/ml Sputum | | | Add 0.4 ng/ml Sputum | | | Add 0.2 ng/ml Sputum | | |
|---|---|---|---|---|---|---|---|---|---|---|---|---|
| Recovered (ng/ml) | DES | IDS | DES/IDS | DES | IDS | DES/IDS | DES | IDS | DES/IDS | DES | IDS | DES/IDS |
| Mean(n = 3) | 0.09 | 0.03 | 0.12 | 0.4 | 0.4 | 0.8 | 0.24 | 0.24 | 0.48 | 0.19 | 0.12 | 0.32 |
| ±SD | 0.01 | 0.01 | 0.01 | 0.06 | 0.05 | 0.09 | 0 | 0.04 | 0.04 | 0.04 | 0.02 | 0.01 |
| % CV | 13 | 42 | 7 | 15 | 11 | 11 | 0 | 18 | 9 | 18 | 18 | 4 |
| % Recovery*2 | | | | 81 | 94 | 87 | 84 | 104 | 93 | 101 | 95 | 99 |

*1) DES/IDS were spiked into control body fluids at three concentrations (expected ranges of detection). The samples were acid hydrolyzed (6N HCl at 110° C. for 24 hrs), chromatographed by SPE (CF1 column). After addition of the internal standard DES/IDS were measured by LC/MSMS and calculated for recovery.
*2) More accurate % Recovery was obtained by integration of combined areas of DES/IDS. % Recovery of individual DES and IDS may varied by chromatographic separation.

This proposed method was used to measure DES and IDS in urine, plasma, and sputum of a cohort of COPD patients as compared to their healthy controls (FIG. 22A-C.) The results confirm our previous reports[54] that the DES/IDS levels are useful biomarkers to characterize elastin degradation in COPD.

The degradation of elastin-containing tissues also occur in aorta[44,64], skin[43,65,66], and liver[67], etc. The developed LC/MSMS analysis of DES/IDS can have wide application for investigating diseases which involve in those elastic tissues.

In sum, we have developed a sensitive, reproducible, and practical method using tandem mass spectrometric LC/MSMS analysis to measure DES and IDS using acetylated pyridinoline as the internal standard. This procedure can serve as a standardized LC/MSMS method to measure DES and IDS in all relevant body fluids, which are important for the clinical assessment of elastin degradation in diseases. The developed method demonstrated increased DES/IDS levels in urine, plasma, and sputum samples of patients with COPD over healthy controls. This analytical method can be applied to investigate diseases which induce elastic tissue degradation in vivo.

Example 6—The Effect of Second Hand Smoke Exposure on Markers of Elastin Degradation As set forth above, desmosine and isodesmosine (D/I) are two crosslinked pyridinoline amino acids specific to peptides produced from elastin degradation[55]. D/I have been measured by liquid chromatography tandem mass spectrometry (LC/MS/MS) in patients with COPD and found to be elevated as compared to normal controls. For the first time these peptides have been measured in subjects exposed to second hand smoke. Desmosine and isodesmosine were found to be statistically significantly elevated in patients exposed to second hand smoke as compared to normal controls.

Materials/Methods
Patients

Two cohorts of subjects, Cohorts I and II, were studied. Cohort I had three sub-groups of subjects which were studied for the effect of SHS exposure on D/I levels. These subjects were part of an ongoing study to determine the effect of SHS exposure on hormonal constituents in females. All subjects completed a lifestyle and nutritional questionnaire that included a description of exposure to cigarette tobacco smoke. Subjects were divided into three groups, active smokers, passive smokers and non-exposed. Passive smokers were defined as anyone who has lived with or has been exposed to cigarette smoke on a daily basis, but were not smokers. Most subjects were exposed within the home.

Active smokers were persons who were smoking daily. Exclusion criteria included several medical conditions including: congestive heart failure, myocardial infarction, cerebral vascular accident, asthma, bronchitis, emphysema, any malignancy; also subjects exposed to dyes (textiles, arts and crafts) on a regular basis. Subjects were initially screened as eligible by telephone and then came for a study visit. All patients were female between the ages of 18-50 yrs. with the majority of them in the late twenties and thirties. They were not taking hormonal contraceptives and were not pregnant at the time of the study.

Cohort II was also subdivided into 3 groups of active smokers, passive smokers and non exposed in smaller numbers. Subjects were males and females between the ages of 22 and 69 years. They were recruited from a medical clinic in the Veteran's Administration Hospital where, after clinical evaluation, they were considered to be in normal health and were, or were not, exposed to cigarette smoke. Some subjects responded to an advertisement requesting participation in this study. Most subjects were exposed to second hand smoke in the occupational setting; i.e. bartenders, construction workers, office workers. All passive smoke exposures in Cohorts I and II were current and not past.

The degree of second hand smoke exposure in Cohort I was determined from the volunteered histories given on a questionnaire. Subjects reported the number of individuals that smoked in the household, an estimation of the number of cigarettes each individual smoked per day and the period time the subject lived in the household. A number was calculated reflecting these variables. A score less than 2,000 was considered mild exposure; 2,000-10,000 moderate exposure and over 10,000 severe exposure. Mild, moderate and severe exposures were then used in the analysis.

Such detailed information on the occupation and household environmental exposure was not available in Cohort II. The subjects of Cohort II indicated their occupation and that they were exposed to second hand smoke and were not actively smoking themselves.

Chemicals

Desmosine (D) and Isodesmosine (I) standard (mixed 50% D and 50% I) were purchased from Elastin Products Company (Owensville, Mich.), CF1 cellulose powders were from Whatman (Clifton, N.J.), and all other reagents were from Sigma (St. Louis, Mo.).

Preparation of Blood Samples

Plasma samples were obtained after centrifuging venous blood specimens with EDTA for 2,500 revolutions per minute for 15 min. Plasma samples were stored at −80° C. until used. 0.25 ml of serum and 0.25 mL of concentrated HCl (37%) were placed in a glass vial. After air in the sample was displaced with a stream of nitrogen, the sample was acid hydrolyzed at 110° C. for 24 hr. The hydrolysates were filtered and dried, the residue was dissolved in 2 mL of the mixed solution (n-butanol/acetic acid/water, 4:1:1 by volume). The sample solution was loaded onto a 3-mL CF1 cartridge. The CF1 cartridge was prepared by introducing 3.5 mL of the slurry of 5% CF1 cellulose powder in the mixed solution between two polypropylene frits. The cartridge was washed three times with 3 mL of the mixed solution, and the D and I adsorbed in the CF1 cartridge were eluted with 3 mL of water. The eluate was evaporated to dryness under vacuum at 45° C., and the residue was dissolved in 0.1 mL of HPLC mobile phase for LC/MS/MS analysis.

Samples were processed and measured in duplicate, and the results were averaged. The mean recoveries of D/I and from 0.20 ng/ml plasma were 67±1 and 72±4%, respectively. Values in plasma were corrected for recovery losses.

Measurement of Desmosine/Isodesmosine by LC/MS/MS Analysis

The Thermoscientific TSQ Quantum Discovery tandem LC/MS/MS system was used for the analysis. HPLC column was a 150×2 mm (3 µm) Atlantis dc18 (Waters, Miss.). The mobile phase A is a solution containing 5 mM ammonium acetate and 7 mM heptafluorobutyric acid in water and the mobile phase B is a solution containing 5 mM ammonium acetate and 7 mM heptafluorobutyric acid in a acetonitrile/water (8:2 ratio). The flow rate of mobile phase is 0.2 ml/min and is programmed from mobile phase A 100% to 88% in 12 mins.

Reaction ion monitoring (RIM) of the transition ions, m/z 526 to m/z 481+m/z 397, was used for the quantitative measurements of D and I. Between-run imprecision (% CV) at D/I levels of 0.10, and 0.20 ng/ml were 4.0% and 3.9% respectively.

IRB approval has been obtained from IRB Georgetown University Medical Center (2006-132) and from Carl T. Hayden, VAMC (Robbins 003).

Measurement of Cotinine by LC/MS/MS Analysis

To indicate exposure to cigarette tobacco smoke, plasma cotinine, a metabolite of nicotine, was quantitated using LC/MS/MS (Applied Biosystem API-4000 or Thermoscientific TSQ Quantum Discovery) following extraction by a solvent (ethyl acetate) extraction. Internal standard ($D_3$-cotinine) solution was added to subject samples and samples were vortexed and centrifuged. The supernatant was injected into the LC/MS/MS system. Cotinine was measured by monitoring the Q1/Q3 transition ions of cotinine at m/z 177 to 80 and $D_3$-cotinine at m/z 180 to 80. Between-run imprecision (% CV) at cotinine levels of 33, 124, and 248 ng/ml were 7.2, 5.6, 3.6% respectively.

Statistical Analysis

A t-test adjusted for unequal variance was used to test the null hypothesis. The level of significance was 0.05. The p-values were calculated based on the summed values of D and I using the unpaired t-test (The used software is "Graph-Pad Prism 4 (2)").

Results

Figure 23A:
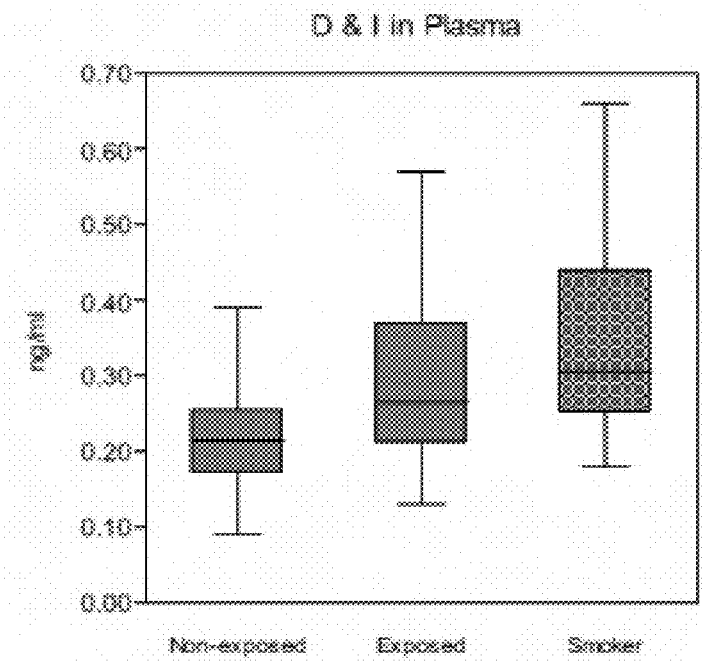
FIG. 23A: Desmosine/Isodesmosine (D/I) levels in plasma of 98 subjects (Cohort I). The boundaries of the box indicate between the $25^{th}$ to $75^{th}$ percentile, the line within the box is the median, the whiskers show the ranges of data points. The D/I levels are illustrated for: a) individuals that have not been exposed to second-hand smoke ("non-exposed") (n=30), median 0.22 ng/ml; b) individuals that have been exposed to second-hand smoke ("exposed") (n=34), median 0.27 ng/ml; and c) smokers ("smokers") (n=34), median 0.31 ng/ml. The P values for the following comparisons are also provided: non-exposed vs. exposed, P=0.0050; exposed vs. smokers, p=0.0533; non-exposed vs. smokers, p<0.0001.
Figure 23B:
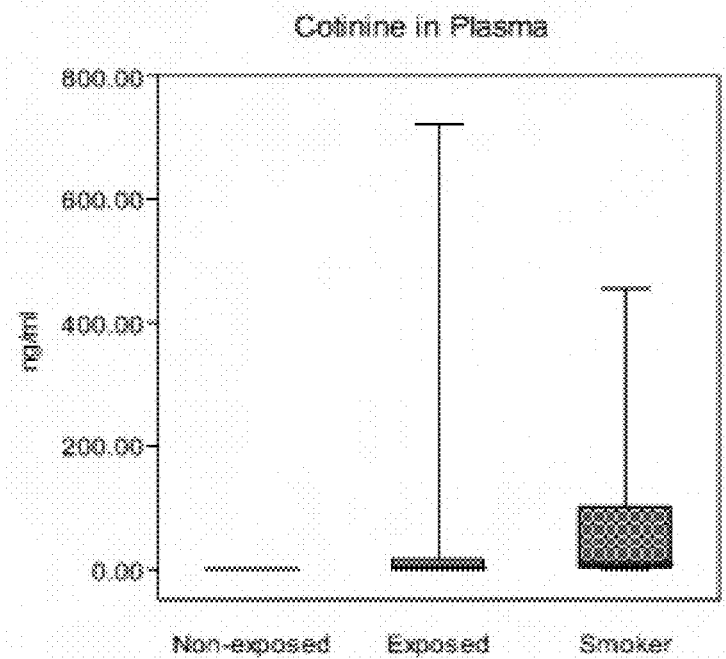
FIG. 23B: Cotinine levels in plasma of 98 subjects (Cohort I). The boundaries of the box indicate between the $25^{th}$ to $75^{th}$ percentile, the line within the box is the median, the whiskers show the ranges of data points. The cotinine levels are illustrated for: a) individuals that have not been exposed to second-hand smoke ("non-exposed") (n=30), median 0 ng/ml; b) individuals that have been exposed to second-hand smoke ("exposed") (n=34), median 0 ng/ml; and c) smokers ("smokers") (n=34), median 9.36 ng/ml. The P values for the following comparisons are also provided: non-exposed vs. exposed, P=0.1161; exposed vs. smokers, p=0.2117; non-exposed vs. smokers, p=0.0012

Results for all three groups of non-exposed, exposed, and smokers in 98 subjects (Cohort I) are shown in FIG. 23A-B. The mean D and I level in non-exposed is 0.22±0.07 ng/ml (n=30), while the level in exposed is 0.29±0.10 ng/ml (n=34) and smokers is 0.34±0.12 ng/ml (n=34). The p value when comparing non-exposed D and I levels to exposed was statistically significant, P=0.005. The p values of non-exposed to smokers was <0.0001, and the value of exposed vs. smokers is near statistical significance, p=0.0533 (FIG. 23A).

Figure 24A:
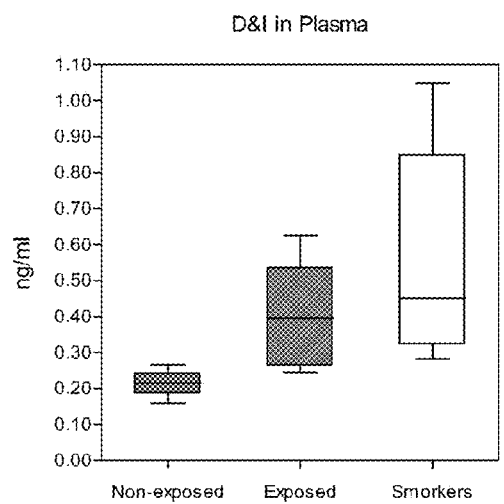
FIG. 24A: Desmosine/Isodesmosine (D/I) levels in plasma of 22 subjects (Cohort II). The boundaries of the box indicate between the $25^{th}$ to $75^{th}$ percentile, the line within the box is the median, the whiskers show the ranges of data points. The D/I levels are illustrated for: a) individuals that have not been exposed to second-hand smoke ("non-exposed") (n=7), median 0.21 ng/ml; b) individuals that have been exposed to second-hand smoke ("exposed") (n=6), median 0.40 ng/ml; and c) smokers ("smokers") (n=9), median 0.45 ng/ml. The P values for the following comparisons are also provided: non-exposed vs. exposed, P=0.0223; exposed vs. smokers, p=0.1782; non-exposed vs. smokers, p=0.0075.
Figure 24B:
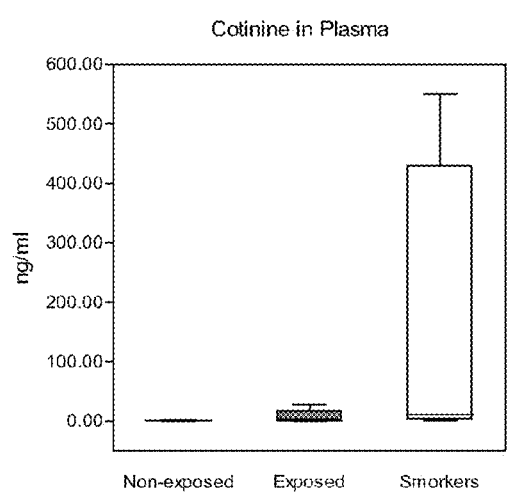
FIG. 24B: Cotinine levels in plasma of 22 subjects (Cohort II). The boundaries of the box indicate between the $25^{th}$ to $75^{th}$ percentile, the line within the box is the median, the whiskers show the ranges of data points. The cotinine levels are illustrated for: a) individuals that have not been exposed to second-hand smoke ("non-exposed") (n=6), median 0.84 ng/ml; b) individuals that have been exposed to second-hand smoke ("exposed") (n=5), median 0.80 ng/ml; and c) smokers ("smokers") (n=9), median 11.8 ng/ml. The P values for the following comparisons are also provided: non-exposed vs. exposed, P=0.4008; exposed vs. smokers, p=0.0740; non-exposed vs. smokers, p=0.3470.

Cohort II compared D/I plasma levels and levels of cotinine also in 22 subjects of non-exposed, exposed, and smokers. The study includes males as well as females and shows the D and I levels and cotinine levels in those subjects (FIGS. 24A-24B). The average D/I (ng/ml plasma) was 0.21±0.03 in the non exposed group and 0.40±0.13 in the second hand smoke exposed group. The smoking group had a measurement of 0.55±0.28. The p values were 0.0233 for the non-exposed vs. the second hand smoke exposed group and 0.0075 for the non-exposed vs. smoking group. The resulting p value when second hand exposure was compared to active smoking was not significant 0.1782 (FIG. 24A).

Figure 25:
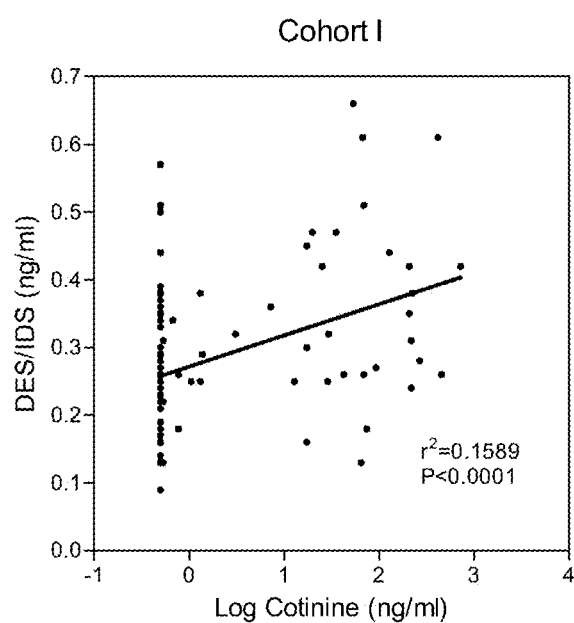
FIG. 25: Cohort I: A statistically significant correlation is shown between the log values of plasma cotinine concentration and plasma levels of D/I in cohort 1.

Cotinine values for each of the cohorts are shown in FIGS. 23B and 24B. Cotinine values showed a large variation in each cohort. In Cohort I there was a significant correlation between the plasma level of D/I and the log value of plasma cotinine as shown in FIG. 25. In Cohort II, with fewer subjects overall and fewer in each category of exposure, such correlations were not statistically significant. Cotinine levels in Cohort I in second hand tobacco smoke exposure exceeded those in cohort II while D/I levels were higher in Cohort II second hand smokers than in Cohort I.

Comparison of the mean levels of plasma D/I and cotinine in Cohorts I and II showed no statistically significant difference in D/I in the non-exposed group but statistically significant differences in the exposed and actively smoking groups (p=0.023 and p=0.004), respectively, for D/I but not statistically significant differences for cotinine for those groups respectively (p=0.350 and p=0.560).

Among active smokers the levels of D/I were higher in Cohort II consistent with their higher pack/year histories.

Discussion

The United States EPA estimates that passive smoking accounts for roughly 3000 deaths in the United States secondary to lung cancer annually[68]. The impact of passive smoking on overall health is clearly recognized as an independent risk factor for diseases including the lung[71].

The levels of D and I in urine and plasma in COPD have been found to be consistently elevated in many studies by various analytical methods[54,55]. This raises the prospect that elevated levels of D/I induced by second hand smoke exposure become an indicator of risk to develop COPD in later life.

As shown above, both cohorts of subjects demonstrate a statistically significant increase in plasma levels of D/I in subjects exposed to SHS none of whom had clinical symptoms of respiratory disease.

Disclosed herein are the first reported measurements of the effect of second hand smoke exposure on elastin degradation in human subjects. This is a demonstration of a tissue matrix effect which may have special significance for lung structure. The further implication of increased elastin degradation of mature elastin is increased elastase activity in tissues and possibly an upgraded inflammatory state. The patients studied in all groups were not symptomatic. Neither group had any significant medical history or evidence of lung pathology. All had equivalent and average exercise tolerance. As is the case with the effects of direct smoke exposure which takes years before evidence of COPD is apparent, SHS smoke exposure may produce its effects decades later. The results also suggest that even mild passive smoke exposure could have deleterious effects on lung parenchyma, which if persistent long term may result in parenchymal inflammation and destruction resulting in COPD.

The clinical significance of the findings in this study are still unclear. As mentioned earlier, patients with excessive, chronic second hand smoke exposure do suffer the sequalae of active smokers[70]. In patients with COPD, elastin fibers have been shown to be degraded and disorganized, and the content of lung elastin is low in such patients[45,50]. Also once elastin breakdown has occurred, the resulting peptides may promote further parenchymal destruction since they may be antigenic and chemotactic. The peptides are chemotactic for neutrophils and macrophages, resulting in a chronic inflammatory state which could induce further elastin degradation and possibly clinical sequelae in the long term[51].

The increase in levels of D/I in plasma of subjects undergoing SHS exposure raises the question of the mechanism for the increase. Since SHS enters via the respiratory tract the initial effect should be on lung cells and most notably neutrophils and macrophages which undergo stimulation with increased synthesis and secretion of elastases. This augmented activity of elastolysis then can effect degradation of elastin in any site in addition to the lung such as blood vessels and skin which would elevate plasma concentrations.

D and I as biomarkers for COPD have been studied for some time[55]. With advances in technology and preparation of samples, they can be detected with greater sensitivity and specificity[54]. This is significant since the levels in plasma of patients exposed to second hand smoke may have been previously too low to detect. Plasma can be easily obtained from patients. In the past, 24 hr urine has been studied as a medium for D and I measurement. Though promising since there is an increase in free D and I levels in urine in active smokers and COPD patients, it is often difficult for the patient and the practitioner to accurately collect 24 hr urine[54]. If we are able to accurately and precisely detect increased levels in plasma it brings us possibly one step closer to a practical marker of elastin degradation and in effect one step closer to understanding and quantifying lung degradation.

It would be clinically important to learn what happens to the levels of D and I over time in these individuals and whether the levels decrease if the patients are removed from passive smoke exposure, and if they are not removed if the levels continue to increase in response to increased elastin degradation. Menzies et al previously illustrated that when the inciting factor was removed; i.e. smoke in bars where they worked, the subjects rapidly returned to their previous state of health[74]. Such findings would suggest that the levels of D and I should decrease when second hand smoking is terminated. The clinical implications on lung function that this early degradation imposes are unclear. It is noteworthy that the levels of D and I, in passive smokers, were not as high as seen in patients with COPD or alpha-1 antitrypsin deficiency[54]. This finding is not surprising given the burden of disease in patients with COPD and alpha-1 as compared to our study population.

Certain methodological limitations should be noted in this study. The data is reliant on an accurate recognition of second hand smoke exposure by our subjects through self-reporting. This is based on an extensive questionnaire characterizing their exposure to second hand smoke. In previous studies a good correlation between a person's perception of second hand smoke and the lab findings consistent with exposure to SHS has been shown[73]. The questions are very specific about who smokes in the home, how much, for how long, and how much time the subject spends within this environment. The questionnaire administered to all persons participating in this study included the same questions, therefore each study group was exposed to the same level of bias.

Of interest is the measurement of cotinine levels. Previous studies have established a positive correlation between the level of SHS exposure and inflammatory cytokine elevation[77,82]. On average they were significantly elevated in subjects that self-reported SHS exposure when compared to subjects without any exposure. The drawback is that cotinine remains elevated only for short periods of time post exposure and correlations with presumed exposure may be weak[83]. This could explain why certain subjects have low cotinine levels.

In the past, multiple studies illustrated that the levels of inflammatory cytokines, on average, are higher in males than females[70,72,74]. It is postulated that males are more sensitive to the inflammatory cytokines than females vs. a possibility of greater exposure in males than in females. It is noteworthy that second hand smokers in Cohort I, which was exclusively a female population of subjects, has lower levels of D/I for the cotinine level which was higher than that among passive smokers in Cohort II. This raises the possibility that females may be less susceptible to elastin degradation by exposure to tobacco smoke, a prospect which should be explored further.

This study illustrates that second hand smoke exposure may be as dangerous and harmful as active smoking on tissue matrix injury and possibly lung parenchyma. This study demonstrates that D and I can be used to detect early changes of elastin degradation, before clinically significant symptoms occur, and possibly to indicate progression of the disease. Thus, D and I can serve as biomarkers of exposure. It would be significant to determine, if increased levels of D and I can be correlated with computed tomography (CT) findings of significant parenchymal destruction, before clinical symptoms occur. Overall having a tissue matrix component effected by second hand smoke and detectable by chemical analysis is a useful adjunct to evaluating clinical and physiological consequences of environmental smoke exposure.

Example 7—Characterization of Peptide Fragments from Lung Elastin Degradation in Chronic Obstructive Pulmonary Disease As noted above, COPD is characterized by destruction of alveolar walls, obstruction of bronchioles, and trapping of air[86,87]. An early insight into the mechanisms leading to alveolar destruction in patients with pulmonary emphysema is that lung matrix elastin is a target for protease degradation by cellular elastases[80,88,89].

Lung elastin is a highly cross-linked insoluble protein formed by condensation of lysyl residues in the soluble precursor, tropoelastin (786 amino acids; Table 5), which can be degraded into soluble peptide fragments by the elastolytic enzymes produced by neutrophils and macrophages. Degradation of lung elastin occurs in COPD as well as in smoking subjects and has been investigated by measurement of 2 lysyl-derived cross-linked pyridinium molecules, desmosine and isodesmosine[11,14,40,54,90], which only exist in elastin and have been shown to be useful biomarkers for lung elastin degradation in COPD patients[54,55].

TABLE 5

| Human Tropoelastin Sequence (Swiss-Prot P15502) (SEQ ID NO: 1) | | | | | |
|---|---|---|---|---|---|
| MAGLTAAAPR | PGVLLLLLSI | LHPSRPGGVP | GAIPGGVPGG | VFYPGAGLGA | 50 |
| LGGGALGPGG | KPLKPVPGGL | AGAGLGAGLG | AFPAVTFPGA | LVPGGVADAA | 100 |
| AAYKAAKAGA | GLGGVPGVGG | LGVSAGAVVP | QPGAGVKPGK | VPGVGLPGVY | 150 |
| PGGVLPGARF | PGVGVLPGVP | TGAGVKPKAP | GVGGAFAGIP | GVGPFGGPQP | 200 |
| GVPLGYPIKA | PKLPGGYGLP | YTTGKLPYGY | GPGGVAGAAG | KAGYPTGTGV | 250 |
| GPQAAAAAAA | KAAAKFGAGA | AGVLPGVGGA | GVPGVPGAIP | GIGGIAGVGT | 300 |
| PAAAAAAAAA | AKAAKYGAAA | GLVPGGPGFG | PGVVGVPGAG | VPGVGVPGA | 350 |
| IPVVPGAGIP | GAAVPGVVSP | EAAAKAAAKA | AKYGARPGVG | VGGIPTYGVG | 400 |
| AGGFPGFGVG | VGGIPGVAGV | PSVGGVPGVG | GVPGVGISPE | AQAAAAAKAA | 450 |

TABLE 5 -continued

Human Tropoelastin Sequence (Swiss-Prot P15502) (SEQ ID NO: 1)

```
KYGAAGAGVL GGLVPGPQAA VPGVPGTGGV PGVGTPAAAA AKAAAKAAQF      500

GLVPGVGVAP GVGVAPGVGV APGVGLAPGV GVAPGVGVAP GVGVAPGIGP      550

GGVAAAAKSA AKVAAKAQLR AAAGLGAGIP GLGVGVGVPG LGVGAGVPGL      600

GVGAGVPGFG AGADEGVRRS LSPELREGDP SSSQHLPSTP SSPRVPGALA      650

AAKAAKYGAA VPGVLGGLGA LGGVGIPGGV VGAGPAAAAA AAKAAAKAAQ      700

FGLVGAAGLG GLGVGGLGVP GVGGLGGIPP AAAAKAAKYG AAGLGGVLGG      750

AGQFPLGGVA ARPGFGLSPI FPGGACLGKA CGRKRK                     786
```

The degradation of cross-linked elastin by elastases results in elastin fragments of varying molecular weight and can be identified as elastin-derived peptides (EDPs). Immunologic detection of EDPs in body fluids in COPD patients and smokers has been studied, but provides little information with regard to their structural identities[38,92,93]. Extensive purifying and sequencing studies of elastin molecules in the elastic fibers in bovine ligament or aorta have been carried using various proteolytic enzymes[33,94-100]. However, the cross-linking domains and structure have not been fully characterized because of the protein's high degree of cross-linking and its insolubility. Using liquid chromatography/tandem mass spectrometry (LC/MSMS) analysis, Barroso et al.[100] reported the amino acid sequences in the peptide fragments produced by different proteolytic enzymes in vitro, but did not further study the detection of such peptides in body fluids. In the present application we utilize LC/MSMS analysis to characterize a full spectrum of EDPs obtained in vitro with 2 representative elastases, human neutrophil elastase (HNE) and macrophage metalloproteinase (MMP12), which have been involved clinically in lung elastin degradation[7,101]. We further demonstrate the detection of some of the characterized peptides in the body fluids of patients with COPD.

The structural characterization of EDPs detected in patients can identify the enzymatic reactions leading to their formation and their possible role in pathogenesis. In addition, EDPs have been shown to play a role in cellular behavior within the extracellular matrix, such as chemotaxis for neutrophils and macrophages or tumor cells. Such factors may affect the progression of COPD or pulmonary metastasis once elastin degradation has occurred[102-105].

Antigenic autoimmune effects of EDPs in COPD patients have also been demonstrated[106,107].

Materials and Methods

Materials

Purified human lung elastin, bovine neck ligament elastin, human sputum neutrophil elastase (HNE), murine macrophage metalloproteinase (MMP12) were obtained from Elastin Products Company (Owensville, Miss.). Porcine pancreatic elastase (PPE) was purchased from Worthington (Lakewood, N.J.), and synthetic peptide standards were obtained from GenScript (Piscataway, N.J.).

Patients Studied

The 5 patients studied were selected at random from subjects with a diagnosis of COPD (Table 6). The diagnostic criteria conformed to those stated in the Global Criteria and Guidelines[60]. One of the 5 patients had α1-antitrypsin deficiency (AATD) of the ZZ phenotype. All had a strong smoking history from 30 to 79 pack-years but had stopped smoking approximately 3 years prior to this study. Four healthy control subjects were males, ages 35 to 85, in good health without respiratory symptoms or a history of smoking or exposure to second hand smoke.

TABLE 6

Patients With Diagnosis of COPD

| Patients | Age | Gender | Race | FVC % Pred | FEV$_1$ % Pred | RV/TLC % Pred | DLCO % Pred | Smoking history (Pk-Yr) | BMI | D/I (ng/mL) |
|---|---|---|---|---|---|---|---|---|---|---|
| 1* | 42 | M | C | 70 | 23 | 34 | 64 | 79 | 30.4 | 0.52 |
| 2 | 68 | F | H | 67 | 46 | 81 | 98 | 18 | 23.1 | 0.51 |
| 3 | 63 | M | C | 74 | 46 | 59 | 59 | 50 | 22.1 | 0.32 |
| 4 | 82 | F | C | 57 | 41 | — | — | 60 | 21.0 | 0.54 |
| 5 | 88 | M | C | 99 | 68 | 65 | 54 | 30 | 23.6 | 0.66 |

Note.
FVC % Pred = forced vital capacity % of predicted; FEV$_1$% Pred = forced expiratory volume in 1 second % of predicted; RV/TLC % Pred = residual volume/total lung capacity % of predicted; BMI = body mass index; D/I = plasma levels of desmosine/isodesmosine; C = Caucasian; H = Hispanic.
*Patient 1 has homozygous ZZ α$_1$-antitrypsin deficiency.

Elastase Digestion

To determine EDPs produced by elastases in human lung, we digested human lung elastin by 2 representative elastolytic enzymes, human neutrophil elastase (HNE) isolated from human sputum[108] and macrophage metalloproteinase (MMP12) isolated from mouse peritoneal lavage[109], which has been shown to be a mouse orthologue of human alveolar macrophages metalloproteinase[110,111].

Human lung elastin (4 mg) was suspended in 1 mL of 0.1 M ammonium carbonate buffer, pH 7.8. The suspension was digested by addition of 0.1 mg HNE (875 U/mg) or 25 μg MMP12 (37.5 U/mg) or 7 mg PPE (8 U/mg) and stirring at room temperature for 12 hours. After 12 hours the digestions were repeated for the second time by addition of another portion of fresh enzymes. The digested mixtures were fractionated into 3 fractions of molecular weight cut-off: (1)<10,000, (2) 10,000-50,000, (3) >50,000 Da using Centricon (Millipore, Mass.) membrane filtration tubes.

Characterization of Peptides by LC/MSMS Analysis

A TSQ Discovery electrospray tandem mass spectrometer (Thermo Electron) was used for both LC/MS and LC/MSMS analysis. High-performance liquid chromatography (HPLC) conditions involved the use of a Symmetry 1 mm×5 cm dC18 (5 µm) column (Waters, Milford, Mass.) and programming from a 5% acetonitrile/water (0.1% formic acid) to 50% acetonitrile/water (0.1% formic acid) for 50 minutes under a flow rate of 100 µL/min. LC/MS analysis was carried out in positive ion mode with a spray voltage of 4,000 volts and an ion transfer tube temperature of 300° C. LC/MSMS analysis was performed by stepping up collision energy from 20 to 40 eV with the increase in the molecular weights from 500 to 1500 Da. The peptide sequences were assigned by searching their MS/MS spectra against the SwissProt database by either PEAK (Bioinformatics Solution, Waterloo, Canada) or MASCOT (Matrix Science, MA) software.

Selected Reaction Monitoring (SRM) of EDPs in Body Fluids

Plasma samples were obtained after centrifuging venous blood specimens at 2500 revolutions per minute for 25 minutes. Samples were stored at −20° C. until used. Sputum samples of COPD patients were collected from spontaneously produced sputum. All patients gave informed consent for the study, and the study was approved by the institutional review board.

One milliliter of plasma or sputum from selected COPD patients were filtered by a Centricon membrane to obtain molecular weight cut-off fractions of <10,000 Da. One transition ion (the most abundant CID ion) was selected from each characterized EDP, and they were searched for the presence of the corresponding EDPs in the LC/MSMS spectra obtained from body fluids of COPD patients. Four synthetic peptides, GYPI (SEQ ID NO:5), APGVGV (SEQ ID NO:4), GLGAFPA (SEQ ID NO:11), and VGVLPGVPT (SEQ ID NO:16), were used for structural confirmation and as external standards for the SRM quantitation.

Results

Figure 26:
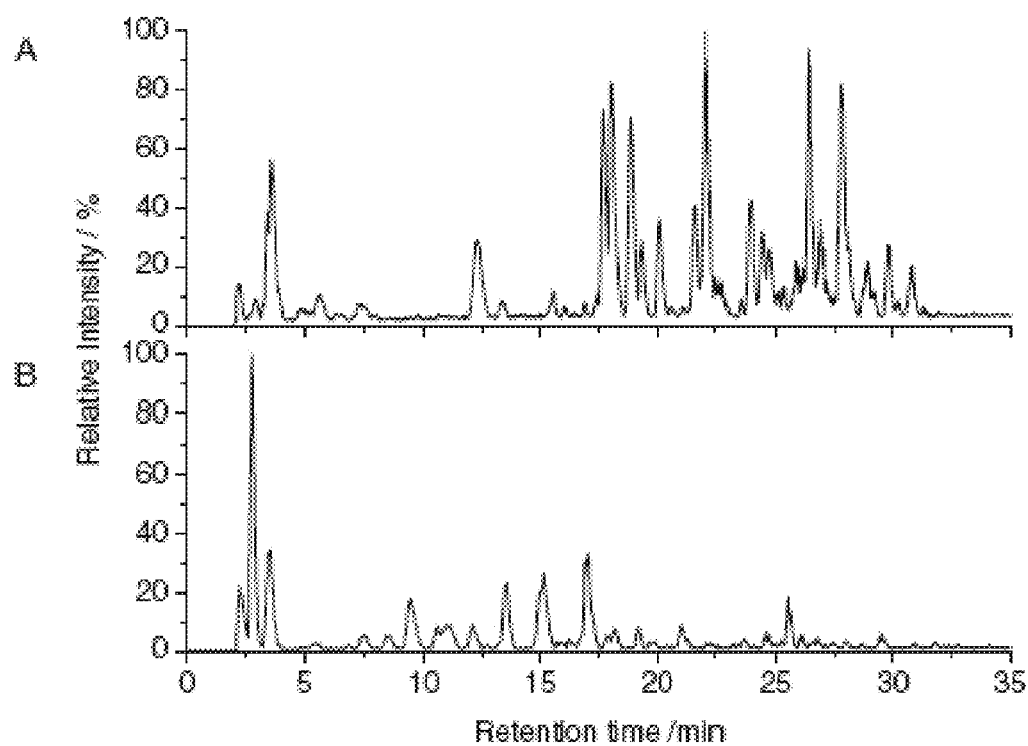
FIG. 26: HPLC/MS base peak chromatograms of human lung EDP's (<10,000 Da) using (A) HNE digestion; and (B) MMP12 digestion.
Figure 27:
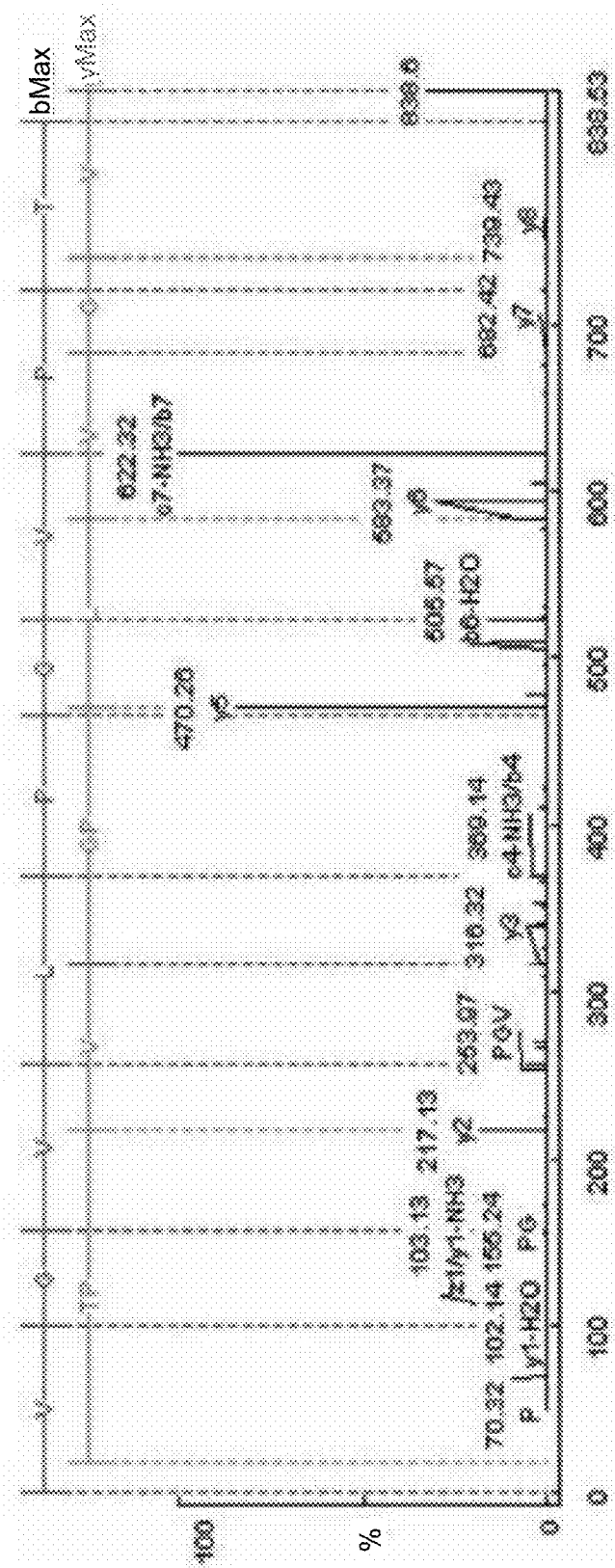
FIG. 27: Annotated MS/MS spectrum of peptide VGV-LPGVPT (SEQ ID NO:16) (m/z 838) with alignment by de novo PEAK assignment of the amino acid sequence.

Identification of Lung Elastin-Derived Peptides (EDPs) Produced by Neutrophil and Macrophage Metalloproteinase Digestions Samples of human lung elastin were digested by HNE and MMP12. The digested peptide mixtures were separated into 3 molecular weight cut-off fractions: (1) smaller than 10,000, (2) between 10,000 and 50,000, and (3) larger than 50,000 Da. LC/MS analysis of the peptide fractions indicated that a large portion of soluble EDPs was isolated in fraction 1 (<10,000 Da). Fraction 2 (10,000-50,000 Da) contained essentially the same peptides as that of the fraction 1 but in significantly lower concentration. Fraction 3 (>50,000 Da) contained mostly the undigested solid elastin. Therefore, fraction 1 (<10,000 Da) appears to constitute all major soluble EDPs produced by HNE or MMP12 digestion of lung elastin, as shown in FIGS. 26A and 26B. Each of the major ions in the LC/MS chromatogram of FIGS. 26A and 26B were further fragmented by the tandem mass spectrometry (LC/MSMS) analysis to obtain collision induced dissociation (CID) ion spectra that provide information from which amino acid sequences of each peptide was derived[112,113]. We utilized a computer program, PEAK, to assist de novo interpretation of the CID ion spectra and deduced their amino acid sequences. MASCOT and manual assignments were also utilized to achieve unambiguous assignments, which were searched against the database of human tropoelastin sequences in SwissProt database (P15502) to characterize the EDPs. By this approach, we were able to characterize all of the major peptides, i.e., 24 EDPs produced by the HNE digestion (Table 7) and 16 EDPs produced by the MMP12 digestion (Table 8). FIG. 27 shows an example of the amino acid sequence assignment and characterization of peptide VGVLPGVPT (SEQ ID NO:16).

TABLE 7

Human Lung EDPs (<10,000 da) by HNE Digestion

| Peptides | HPLC (min) | LC/MS (m/z) | Amino acid sequence | Positions in tropoelastin (P15002) |
|---|---|---|---|---|
| 1 | 2.2 | 444 | LGVGV | 582-586 |
| 2 | 3.4 | 444 | GGIPT | 392-386 |
| 3 | 3.7 | 499 | APGVGV | 509-514 |
|   |   |   |   | 515-520 |
|   |   |   |   | 527-532 |
|   |   |   |   | 533-538 |
|   |   |   |   | 539-544 |
| 4 | 12.3 | 449 | GYPI | 205-208 |
| 5 | 13.3 | 520 | VTFPG | 85-89 |
| 6 | 15.5 | 598 | GIPGVV | 675-681 |
| 7 | 16.0 | 866 | APGIGPGGVAA | 545-555 |
| 8 | 17.7 | 598 | GVPGLGV | 587-593 |
|   |   |   |   | 596-605 |
| 9 | 18.0 | 572 | GLGGLGV | 708-714 |
| 10 | 18.1 | 632 | GLGAFPA | 78-84 |
| 11 | 18.1 | 763 | GGIPTYGV | 392-399 |
| 12 | 18.9 | 726 | GAGVPGLGV | 594-602 |
| 13 | 19.3 | 643 | AGLGGLGV | 707-714 |
| 14 | 20.1 | 771 | GAAGLGGLGV | 705-714 |
| 15 | 21.5 | 838 | VGVLPGVPT | 163-171 |
| 16 | 21.6 | 754 | GVGVPGLGV | 585-593 |
| 17 | 22.1 | 543* | AARPGFGLSPI | 760-770 |
| 18 | 23.9 | 930 | GLGAGLGAFPA | 74-84 |
| 19 | 24.4 | 865 | GAGGFPGFGV | 400-409 |
| 20 | 26.4 | 1209 | GLVPGPGFGPGVV | 321-334 |
| 21 | 26.9 | 779* | GVPGAGVPGVGVPGAGIPV | 335-353 |
| 22 | 27.8 | 1139 | FPGVGVLPGVPT | 160-171 |
| 23 | 39.8 | 731* | GVGVPGLGVGAGVPGLGV | 585-602 |
| 24 | 30.8 | 728* | GLGGVLGGAGQFPLGGV | 743-759 |

*Doubly charged ion.

Peptides 1-24 in Table 7 above correspond to SEQ ID NOS:2-25).

TABLE 8

Human Lung EDPs (<10,000 da) by MMP12 Digestion
TABLE 4 Human Lung EDPs (<10,000 da) by MMP12 Digestion

| Peptides | HPLC (min) | LC/MS (m/z) | Amino acid sequence | Positions In tropoelastin (P5002) | Peptides | HPLC (min) | LC/MS (m/z) | Amino acid sequence | Positions in tropoelastin (P5002) |
|---|---|---|---|---|---|---|---|---|---|
| 1 | 1.5 | 499 | VAPGVG | 506-511<br>512-517<br>518-523<br>530-535<br>536-541<br>542-547 | 9 | 11.2 | 476 | FPGVG | 160-164 |
| 2 | 2.2 | 556 | VGAGVPG | 593-599<br>602-608 | 10 | 13.5 | 726 | LGVGAGVPG | 591-599<br>600-608 |
| 3 | 2.7 | 513 | LAPGVG | 526-531 | 11 | 15.1 | 591 | VTFPGA | 85-90 |
| 4 | 3.5 | 596 | LVPGGPG | 322-327 | 12 | 15.2 | 575 | LGAFPA | 79-84 |
| 5 | 7.5 | 655 | VGVAPGVG | 506-513<br>512-519<br>519-525<br>530-537<br>536-543 | 13 | 17.0 | 543* | VYPGGVLPGAR | 149-159 |
| 6 | 8.5 | 584 | VGVGVPG | 584-590 | 14 | 18.2 | 858 | VYPGGVLPG | 149-157 |
| 7 | 9.5 | 541 | LVPGVG | 502-507 | 15 | 21.0 | 859 | FGVGVGGIP | 407-416 |
| 8 | 10.7 | 584 | LGAGPG | 575-581 | 16 | 23.7 | 925 | LGVGVGVPGLG | 582-592 |

*Doubly charged ion.

Peptides 1-16 in Table 8 above correspond to SEQ ID NOS:26-41).

The peptides are rich in nonpolar amino acids, especially G, V, P, A, L, or I, including 2 hexapeptides, APGVGV (SEQ ID NO:4) and VAPGVG (SEQ ID NO:26), and an octapeptide, VGVAPGVG (SEQ ID NO:30), derived from the characteristic elastic repeats (positions 506 to 547; see Table 5) of the hydrophobic domain in tropoelastin[84,114,115].

Detection of Lung EDPs in Body Fluids of COPD

Figure 28:
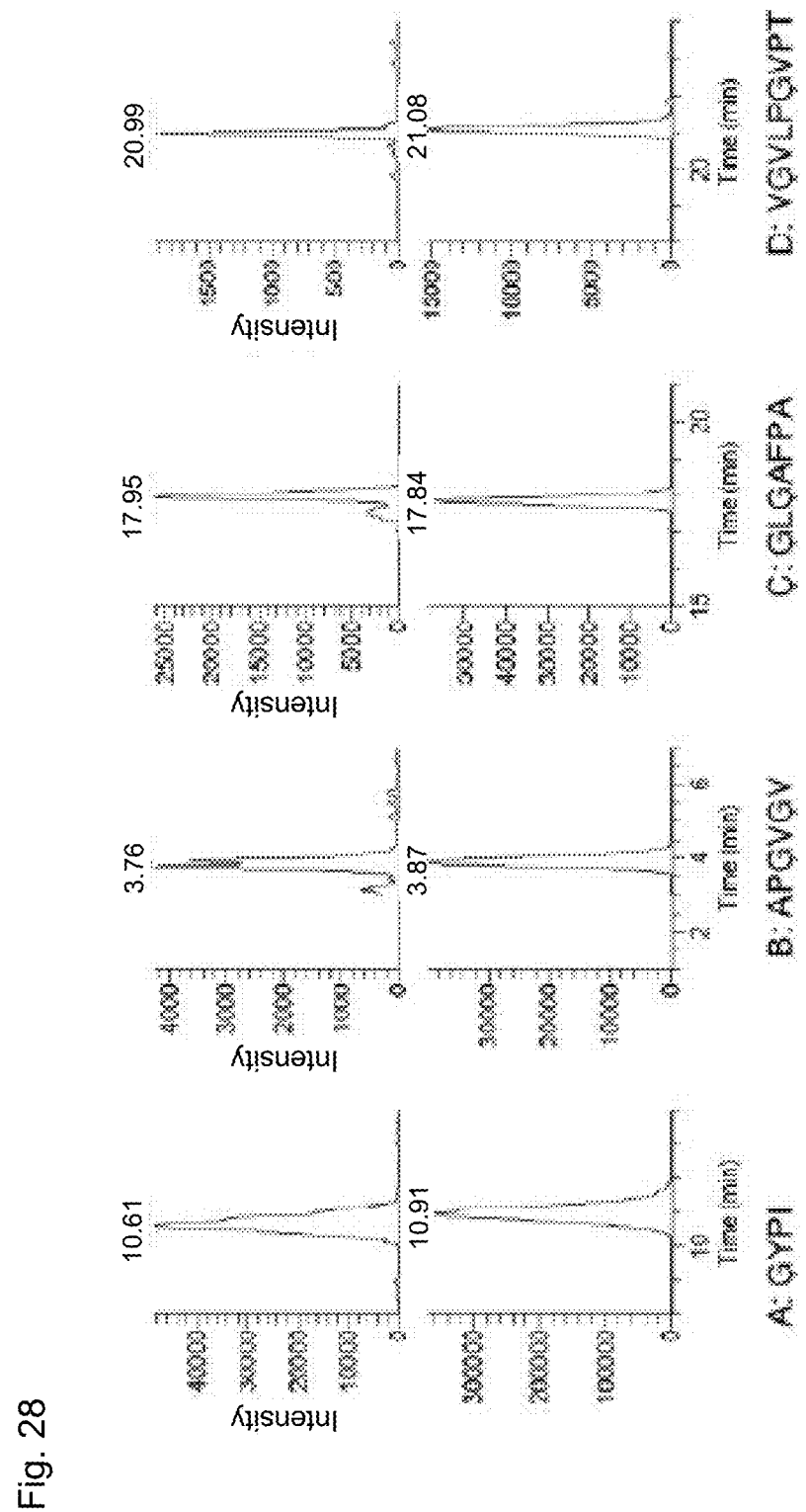
FIG. 28: SRM LC/MS spectra of patient 1's plasma sample (top panels) and 10 ng/ml standard peptides (bottom panels). Transition ions: (A) 449.24 to 229.05; (B) 499.32 to 297.09; (C) 632.35 to 446.21; (D) 838.48 to 622.49 were used for identification and quantitation of the 4 peptides.

Using the SRM of LC/MSMS analysis (see Materials and Methods), the transition ions derived from the 24 EDPs characteristically produced by HNE digestion and the 16 EDPs characteristically produced by MMP12 digestion were used to search for their presence in plasma or sputum obtained from COPD patients. Five patients were selected at random from subjects diagnosed with COPD. The results showed that 3 or 4 peptides, GYPI (NO: 5), APGVGV (SEQ ID NO:4), GLGAFPA (SEQ ID NO:11), and VGVLPGVPT (SEQ ID NO:16), were present in plasma or sputum from 2 COPD patients (patients 1 and 2), but not in 3 other COPD patients and 4 normal controls (Table 9). The identities and quantities of the detected peptides were determined by comparison with the synthetic peptides. The SRM is highly sensitive and specific with a limit of detection, 0.01 ng of peptide present in 1 mL of plasma. FIG. 28 describes the identification and quantification of the peptide in plasma of COPD patient 1.

TABLE 9

Lung EDPs Detected in COPD Patients

| | | GYPI | APGVGV | GLGAFPA | VGVLPGVPT |
|---|---|---|---|---|---|
| Patients | | | | | |
| 1 | Plasma | 0.14 | 0.11 | 0.48 | 0.10 |
| | Sputum | X* | X | 1.01 | X |
| 2 | Plasma | 0.02 | X | 1.44 | 0.04 |
| | Sputum | X | X | X | X |
| 3 | Plasma | X | X | X | X |
| 4 | Plasma | X | X | X | X |
| 5 | Plasma | X | X | X | X |
| Normal subjects | | | | | |
| 1 | Plasma | X | X | X | X |
| 2 | Plasma | X | X | X | X |
| 3 | Plasma | X | X | X | X |
| 4 | Plasma | X | X | X | X |

Hexapeptides APGVGV, VAPGVG, and VGVAPG from the Elastin Repeats

Figure 29:
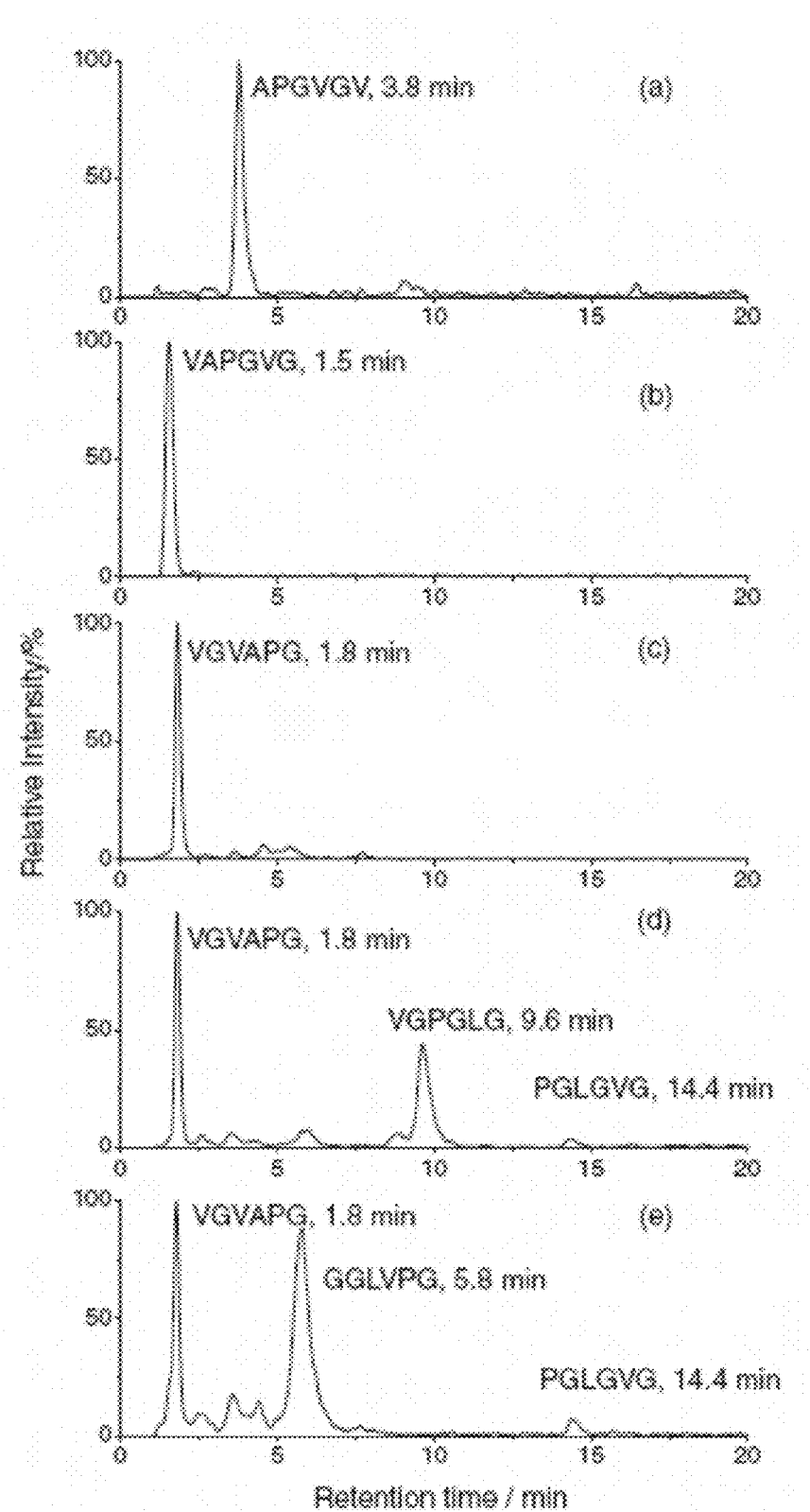
FIG. 29: Ion chromatograms of hexapeptides (m/z 499) derived from hydrophobic elastomeric repeats. Ion chromatograms are illustrated for each of the following sample digestions (a) digestion of lung elastin by HNE; (b) digestion of lung elastin by MMP12; (c) digestion of lung elastin by PPE; (d) digestion of ligament elastin by HNE; (e) digestion of ligament elastin by PPE.

Several EDPs such as the hexapeptide VGVAPG (SEQ ID NO:42), which has been isolated from bovine ligament elastin by porcine pancreatic elastase (PPE) digestion, have been actively studied as chemoattractants for neutrophils and macrophages[116]. However, our LC/MS studies show that the hexapeptide APGVGV (SEQ ID NO:4) is formed by HNE and VAPGVG (SEQ ID NO:26) by MMP12 digestion, with no detection of VGVAPG. We have extended our LC/MSMS analysis to EDPs obtained with the PPE digestions on both lung elastin and bovine ligament elastin. The PPE digestions resulted in characterization of 12 EDPs from Lung elastin (Table 10) and 21 EDPs from ligament elastin (Table 11), and it was found that VGVAPG was exclusively formed by PPE digestion or from digestion of ligament elastin (FIG. 29) but not from digestion with neutrophil or macrophage metalloproteinase. Three additional hexapeptides, GGLVPG (SEQ ID NO:57), VGPGLG (SEQ ID NO:75), and PGLGVG (SEQ ID NO:62), were also identified in the bovine ligament digests by PPE. All 5 hexapeptides are isobaric (the same molecular weight, 499 Da), but their amino acid sequences are varied and can be defined by LC/MSMS.

TABLE 10

Human Lung EDPs (<10,000 Da) by PPE Digestion

| Peptides | HPLC (min) | LC/MS (m/z) | Amino acid sequence | Positions in tropoelastin (P15002) |
|---|---|---|---|---|
| 1 | 2.6 | 499 | VGVAPG | 506-511 |
|   |   |   |   | 512-517 |
|   |   |   |   | 518-523 |
|   |   |   |   | 530-535 |
|   |   |   |   | 536-541 |
|   |   |   |   | 542-547 |
| 2 | 4.5 | 442 | VGLPG | 144-148 |
| 3 | 8.4 | 456 | AGIPV | 349-353 |
| 4 | 9.4 | 449 | GYPI | 205-208 |
| 5 | 10.7 | 419 | VGPF | 192-195 |
| 6 | 16.2 | 912 | VGPFGGLPQPG | 192-201 |
| 7 | 18.0 | 563 | QFGLV | 499-503 |
|   |   |   |   | 700-704 |
| 8 | 18.6 | 786 | GPGFGPGVV | 326-334 |
| 9 | 21.6 | 633 | FGLSPI | 765-770 |
| 10 | 21.6 | 1011 | GLVPGGPGFGPG | 321-332 |
| 11 | 24.0 | 737 | GGFPGFGV | 402-409 |
| 12 | 26.1 | 1209 | GLVPGGPGFGPGVV | 321-334 |

Peptides 1-12 in Table 10 correspond to SEQ ID NOS:42-53.

TABLE 11

Bovine Ligament EDPs (<10,000 Da) by PPE Digestion

| Peptides | HPLC (min) | LC/MS (m/z) | Amino acid sequence | Positions in tropoelastin (P04985) |
|---|---|---|---|---|
| 1 | 2.4 | 702 | GGVGDLGGA | 619-627 |
| 2 | 2.6 | 499 | VGVAPG | 503-508 |
|   |   |   |   | 521-526 |
| 3 | 3.9 | 442 | VGLPG | 153-157 |
| 4 | 5.8 | 449 | GGLVPG |  |
| 5 | 7.6 | 473 | AGLGGV | 692-697 |
| 6 | 9.0 | 449 | GYPI | 216-219 |
| 7 | 10.3 | 419 | VGPF | 203-206 |
| 8 | 11.5 | 681 | PGVGVVPG | 507-514 |
|   |   |   |   | 513-520 |
| 9 | 13.0 | 499 | PGLGVG | 566-571 |
|   |   |   |   | 575-580 |
|   |   |   |   | 584-589 |
| 10 | 13.4 | 852 | GGQQPGVPL | 207-215 |

TABLE 11-continued

Bovine Ligament EDPs (<10,000 Da) by PPE Digestion

| Peptides | HPLC (min) | LC/MS (m/z) | Amino acid sequence | Positions in tropoelastin (P04985) |
|---|---|---|---|---|
| 11 | 14.5 | 490 | FPGIG | 171-175 |
|   |   |   |   | 429-433 |
| 12 | 16.7 | 433 | FPGI | 171-174 |
|   |   |   | FPGI | 429-432 |
| 13 | 17.9 | 591 | GGIPTF | 417-422 |
| 14 | 17.9 | 804 | GFPGIGDAA | 428-436 |
| 15 | 19.6 | 658 | GQPFPI | 701-706 |
| 16 | 20.9 | 1139 | VGPFGGQQPGVP | 203-214 |
| 17 | 22.5 | 845 | FPGAGLGGLG | 43-52 |
| 18 | 24.8 | 856 | FPGIGVLPG | 171-179 |
| 19 | 24.8 | 1252 | VGPFGGQQPGVPL | 203-215 |
| 20 | 26.5 | 751 | GVFFPGAG | 40-47 |
| 21 | 26.5 | 694 | VFFPGA | 41-47 |

Peptides 1-21 in Table 11 correspond to SEQ ID NOS:54-74.

Discussion

In this study enzymatic digestion of human lung elastin by 2 key enzymes, human neutrophil elastase (HNE) and macrophage metalloproteinase (MMP12), resulted in identification of 24 EDPs from HNE (Table 7) and 16 EDPs from MMP12 (Table 8). The 40 EDPs we have characterized by LC/MSMS analysis appear to represent all major soluble EDPs produced by the HNE and MMP12 digestions of elastin in vitro. The peptides are rich in nonpolar amino acids, especially G, V, P, A, L, or I, from the hydrophobic elastic domain in tropoelastin. Among them, the hexapeptides APGVGV (SEQ ID NO:4), and VAPGVG (SEQ ID NO:26) and the octapeptide VGVAPGVG (SEQ ID NO:30) are derived from the characteristic hydrophobic elastic repeats (positions 506 to 547; Table 5). Tropoelastin consists of alternating repetitive hydrophobic domains of variable length (the elastic repeats) and the alanine-rich lysine-containing domain that form cross-links[114,115]. A model of the elastic property of the elastin matrix proposes that hydrophobic interactions of the 3-spiral elastic repeats are exposed to an aqueous environment to stabilize the folded protein structure[117-119]. The spectrum of EDPs we have characterized suggests that both HNE and MMP12 degradations occur primarily at the site of the hydrophobic elastic repeat domain and result in disintegration of the stable protein structure of elastin.

Recent progress in proteomic LC/MSMS analysis has become an effective approach to characterize protein molecules as biomarkers involved in disease. This study represents the first effort to determine peptide fragments from enzymatic degradations in biological fluids in COPD patients. The 40 EDPs we have characterized by LC/MSMS analysis results from the 2 major elastases involved in elastin degradation in COPD. We believe these EDPs represent all the major soluble EDPs produced by HNE and MMP12 digestions. However, the amino acid sequences produced in our study differ from the sequences produced in the study reported by Barroso et al.[100]. This may be a consequence of a difference in the enzymes used or a difference in the conditions of digestion.

We used the 40 characterized EDPs to search for biomarkers of lung elastin degradation in body fluids obtained from COPD patients. Our preliminary screening of some selected COPD patients have shown that 4 EDPs, GYPI (SEQ ID NO: 5), APGVGV (SEQ ID NO:4), GLGAFPA (SEQ ID NO:11), and VGVLPGVPT (SEQ ID NO:16), were present in plasma or sputum of 2 COPD patients but not in 3 other COPD subjects or healthy controls (Table 9). Two patients (patients 1 and 2) with detectable levels of EDPs have more advanced disease clinically and physiologically. Patient 1 with AATD had evidence of emphysematous destruction on chest x-ray and computed tomography (CT) as did patient 2. The 3 other subjects with undetectable levels of EDPs had mild or little evidence of emphysematous destruction on chest x-ray or CT. All of the detected peptides were among those identified from HNE digestions in vitro, suggesting that this was the active enzyme producing the elastin degradation in vivo in these patients, an observation especially relevant to the patients with AATD. Further study is needed to determine whether the presence of multiple peptides as shown here can be related to the severity of emphysematous destruction by CT. Such studies are planned along with further evaluation of the chemotactic and antigenic potential of the detected peptides. The possible reasons for not detecting EDPs in all patients include (1) levels too low for detection by our mass spectrometry analysis; (2) in vivo intermittent production of such peptides depending upon varying pathological factors; and (3) varying phenotypes of disease in COPD related to causative factors and the host responses. Further study in COPD patients may clarify the basis of these variable results.

The EDPs represented by the hexapeptide VGVAPG (SEQ ID NO:42) isolated from ligamentum nuchae or aorta of animals by porcine pancreatic elastase (PPE) have been shown to be chemoattractants for neutrophils and macrophages, and thus initiators of possible pathogenic consequences of elastin degradation[102-105,120]. Also, VGVAPG has been reported to induce pro-MMP1 and pro-MMP3 upregulation[121]. However, our study with human elastin showed that the hexapeptides APGVGV (SEQ ID NO: 4) and VAPGVG (SEQ ID NO:26) were formed by degradation with human neutrophil elastase (HNE) and macrophage metalloproteinase (MMP12), The hexapeptide VGVAPG (SEQ ID NO:42) could not be detected by the digestion of lung elastin by either HNE or MMP12. VGVAPG (SEQ ID NO:42) was only formed either by the PPE digestion or formed by the digestion of ligamentum nuchae (FIG. 29), and may not be a factor in COPD. Further studies on biological activities of these hexapeptides such as their chemotactic or antigenic properties in relation to the pathogenesis of COPD are under way.

In sum, we utilized proteomic LC/MSMS analysis to characterize the full spectrum of peptides that can be produced by 2 major elastases (neutrophil elastase and macrophage metalloproteinase) in vitro from human lung elastin. These characterized elastin peptides were searched for and several were detected in plasma and sputum in COPD patients. Such elastin peptides were not detected in normal subjects. The detection in vivo of these elastin peptides in COPD patients appears to be varied, which might be a reflection of variable pathogenic processes in COPD. This study demonstrates the feasibility of detecting these elastin peptides in body fluids and relating them to clinical, physiological, and radiological characteristics of COPD and makes possible further study for their pathogenic potential.

All documents cited herein are hereby incorporated by reference as if recited in full herein.

CITED DOCUMENTS

1. Barnes P J, Shapiro S D, Pauwels R A (2003) Chronic obstructive pulmonary disease: molecular and cellular mechanisms. Eur Respir J 22:672-678.
2. Shapiro S D (2002) Proteinases in chronic obstructive pulmonary disease. Biochem Soc Trans 30:98-102.
3. Owen C A (2008) Roles for proteinases in the pathogenesis of chronic obstructive pulmonary disease. Int J Chron Obstruct Pulmon Dis 3:253-268.
4. Djekic U V, Gaggar A, Weathington N M (2009) Attacking the multi-tiered proteolytic pathology of COPD: new insights from basic and translational studies. Pharmacol Ther 121:132-146.
5. Celli B R (2000) The importance of spirometry in COPD and asthma: effect on approach to management. Chest 117 (2 Suppl): 357 15S-19S.
6. Newell J D, Hogg J C, Snider G L (2004) Report of a workshop: quantitative computed tomography scanning in longitudinal studies of emphysema. Eur Respir J 23:769-775.
7. Nakano Y, Muller N L, King G G, Niimi A, Kalloger S E, Mishima M, Pare P D (2002) Quantitative assessment of airway remodeling using high-resolution C T. Chest 122: 271S-275S.
8. Barnes P J (2004) Mediators of chronic obstructive pulmonary disease. Pharmacol Rev 56:515-548.
9. Tzortzaki E G, Lambiri I, Vlachaki E, Siafakas N M (2007) Bio-markers in COPD. Curr Med Chem 14:1037-1048.
10. Ma S, Lin Y Y, Tartell L, Turino G M (2009) The effect of tiotropium therapy on markers of elastin degradation in COPD. Respir Res 10:12.
11. Ma S, Lieberman S, Turino G M, Lin Y Y (2003) The detection and quantitation of free DID in human urine and their peptide-bound forms in sputum. Proc Natl Acad Sci USA 100: 12941-12943.
12. Boschetto P, Quintavalle S, Zeni E, Leprotti S, Potena A, Ballerin L, Papi A, Palladini G, Luisetti M, Annovazzi L, ladorola P, De Rosa E, Fabbri L M, Mapp C E (2006) Association between markers of emphysema and more severe chronic obstructive pulmonary disease. Thorax 61:1037-1042.
13. Fiorenza D, Viglio S, Lupi A, Baccheschi J, Tinelli C, Trisolini R, Iadarola R, Luisetti M, Snider G L (2002) Urinary desmosine excretion in acute exacerbations of COPD: a preliminary report. Respir Med 96:110-114.
14. Viglio S, ladorola P, Lupi A, Trisolini R, Tinelli C, Balbi B, Grassi V, Worlitzsch D, Doring G, Meloni F, Meyer K C, Dowson L, Hill S L, Stockley R A, Luisetti M (2000) MEKC of DID in urine of chronic destructive lung disease patients. Eur Respir J 388 15:1039-1045.
15. Cantor J O, Cerreta J M, Ochoa M, Ma S, Chow T, Grunig G, Turino G M (2005) Aerosolized hyaluronan limits airspace enlargement in a mouse model of cigarette smoke-induced pulmonary emphysema. Exp Lung Res 31:417-430.
16. Dunnill M S (1962) Quantitative methods in the study of pulmonary pathology. Thorax 17:320-328.
17. Mascarenhas M M, Day R M, Ochoa C D, Choi W I, Yu L, Ouyang B, Garg H G, Hales C A, Quinn D A (2004) Low molecular weight hyaluronan from stretched lung enhances interleukin-8 expression. Am J Respir Cell Mol Biol 30:51-60.

18. McKee C M, Penno M B, Cowman M, Burdick M D, Streiter R M, Bao C, Noble P W (1996) Hyaluronan (HA) fragments induce chemokine gene expression in alveolar macrophages. The role of HA size and CD44. J Clin Invest 98:2403-2413.
19. Cantor J O, Cerreta J M, Armand G, Keller S, Turino G M (1993) Pulmonary air-space enlargement induced by intratracheal instillment of hyaluronidase and concomitant exposure to 60% oxygen. Exp Lung Res 19:177-192.
20. Cantor J O, Cerreta J M, Keller S, Turino G M (1995) Modulation of airspace enlargement in elastase-induced emphysema by intratracheal instillment of hyaluronidase and hyaluronic acid. Exp Lung Res 21:423-436.
21. Murakami H, Yoshida M, Aritomi T, Shiraishi M, Ishibashi M, Watanabe K (1998) Effects of hyaluronidase on porcine pancreatic elastase-induced lung injury. J Jpn Respir Soc 36:577-584.
22. Cantor J O, Shteyngart B, Cerreta J M, Armand G, Liu M, Turino G M (2000) The effect of hyaluronan on elastic fiber injury in vitro and elastase-induced airspace enlargement in vivo. Proc Soc Exp Biol Med 225:65-71.
23. Cantor J O, Cerreta J M, Armand G, Turino G M (1998) Aerosolized hyaluronic acid decreases alveolar injury induced by human neutrophil elastase. Proc Soc Exp Biol Med 217:471-475.
24. Cantor J O, Cerreta J M, Armand G, Turino G M (1997) Further investigation of the use of intratracheally administered hyaluronic acid to ameliorate elastase-induced emphysema. Exp Lung Res 23(3):229-244.
25. Baccarani-Contri M, Vincenzi D, Cicchetti F, Mori G, Pasquali-Ronchetti I (1990) Immunocytochemical localization of proteoglycans within normal elastin fibers. Eur J Cell Biol 53:305-312.
26. Scott J E, Cummings C, Brass A, Chen Y (1991) Secondary and tertiary structures of hyaluronan in aqueous solution, investigated by rotary shadowing-electron microscopy and computer simulation. Hyaluronan is a very efficient network-forming polymer. Biochem J 274 (Pt 3):699-705.
27. Nadkarni P P, Kulkarni G S, Cerreta J M, Ma S, Cantor J O (2005) Dichotomous effect of aerosolized hyaluronan in a hamster model of endotoxin-induced lung injury. Exp Lung Res 31:807-818.
28. Cocci F, Miniati M, Monti S, Cavarra E, Gambelli F, Battolla L, Lucattelli M, Lungarella G (2002) Urinary desmosine excretion is inversely correlated with the extent of emphysema in patients with chronic obstructive pulmonary disease. Int J Biochem Cell Biol 34:594-604.
29. Comhair S A, Erzurum S C (2002) Antioxidant responses to oxidant-mediated lung diseases. Am J Physiol Lung Cell Mol Physiol 283:L246-L255.
30. Baskaran S, Lakshmi S, Prasad P R (1999) Effect of cigarette smoke on lipid peroxidation and antioxidant enzymes in albino rat. Indian J Exp Biol 37:1196-2000.
31. Wurzel H, Yeh C C, Gairola C, Chow C K (1996) Oxidative damage and antioxidant status in the lungs and bronchoalveolar lavage fluid of rats exposed chronically to cigarette smoke. J Biochem Toxicol 10:11-17.
32. Wright J L, Churg A (1995) Smoke-induced emphysema in guinea pigs is associated with morphometric evidence of collagen breakdown and repair. Am J Physiol Lung Cell Mol Physiol 12:17-20.
33. Thomas J, Elsden D F, Partridge S M. Degradation products from elastin: Partial structure of two major degradation products from the cross-linkages in elastin. Nature 1963; 200:651-2.
34. Shimada W, Bowman A, Davis N R, Anwar R A. An approach to the study of the structure of desmosine and isodesmosine containing peptides isolated from the elastase digest of elastin. Biochem Biophys Res Commun 1969; 37:191-7.
35. Akagawa M, Suyama K. Mechanism of formation of elastin crosslinks. Connect Tissue Res 2000; 41:131-41.
36. Sandberg L B. Elastin structure in health and disease. Int Rev Connect Tissue Res 1978; 7:159-210.
37. Rosenbloom J. Elastin: Biosynthesis, structure, degradation and role in disease processes. Connect Tissue Res 1982; 10:73-91.
38. Schriver E E, Davidson J M, Sutcliffe M C, Swindell B B, Bernard G R. Comparison of elastin peptide concentrations in body-fluids from healthy-volunteers, smokers, and patients with chronic obstructive pulmonary-disease. Am Rev Respir Dis 1992; 145:762-6.
39. Tenholder M F, Rajagopal K R, Phillips Y Y, Dillard T A, Bennett L L, Mundie T G, Tellis C J. Urinary desmosine excretion as a marker of lung injury in the adult respiratory distress syndrome. Chest 1991; 100:1385-1390.
40. Stone P J, Gottlieb D J, O'Connor G T, Ciccolella D E, Breuer R, Bryan-Rhadfi J, et al. Elastin and collagen degradation products in urine of smokers with and without chronic obstructive pulmonary disease. Am J Respir Crit Care Med 1995; 151:952-9.
41. Stone P J, Konstan M W, Berger M, Dorkin H L, Franzblau C, Snider G L. Elastin and collagen degradation products in urine of patients with cystic fibrosis. Am J Respir Crit Care Med 1995; 152:157-62.
42. Bode D C, Pagani E D, Cumiskey W R, von Roemeling R, Hamel L, Silver P J. Comparison of urinary desmosine excretion in patients with chronic obstructive pulmonary disease or cystic fibrosis. Pulm Pharmacol Ther 2000; 13:175-80.
43. Schwartz E, Cruickshank F A, Lebwohl M. Determination of desmosines in elastin-related skin disorders by isocratic high-performance liquid chromatography. Exp Mol Pathol 1990; 52:63-8.
44. Watanabe M, Sawai T. Alteration of cross-linking amino acids of elastin in human aorta in association with dissecting aneurysm: Analysis using high performance liquid chromatography. Tohoku J Exp Med 1999; 187: 291-303.
45. Wright R R. Elastic tissue of normal and emphysematous lungs—a tridimensional histologic study. Am J Pathol 1961; 39:355-67.
46. Yoshida T, Tuder R M. Pathobiology of cigarette smoke-induced chronic obstructive pulmonary disease. Physiol Rev 2007; 87:1047-82.
47. King G S, Mohan V S, Starcher B C, Radioimmunoassay for desmosine. Connect Tissue Res 1980; 7:263-7.
48. Harel S, Janoff A, Yu S Y, Hurewitz A, Bergofsky E H. Desmosine radioimmunoassay for measuring elastin degradation in vivo. Am Rev Respir Dis 1980:122:769-73.
49. Stone P J, Bryanrhadfi J, Lucey E C, Ciccolella D E, Crombie G, Faris B, et al. Measurement of urinary desmosine by isotope-dilution and high-performance liquid-chromatography—correlation between elastase-induced air-space enlargement in the hamster and elevation of urinary desmosine. Am Rev Respir Dis 1991; 144:284-90.
50. Cumiskey W R, Pagani E D, Bode D C. Enrichment and analysis of desmosine and isodesmosine in biological fluids. J Chromatogr B 1995; 668:199-207.
51. Chen J R, Takahashi M, Kushida K, Suzuki M, Suzuki K, Horiuchi K, Nagano A. Direct detection of crosslinks of collagen and elastin in the hydrolysates of human yellow ligament using single-column high performance liquid chromatography. Anal Biochem 2000; 278:99-105.

52. Giummelly P, Botton P, Friot R, Prima-Putra D, Atkinson J. Measurement of desmosine and isodesmosine by capillary zone electrophoresis. J Chromatogr 1995; 710:357-60.

53. Viglio S, Zanaboni G, Luisetti M, Trisolini R, Grimm R, Cetta G, Iadarola P. Micellar electrokinetic chromatography for the determination of urinary desmosine and isodesmosine in patients affected by chronic obstructive pulmonary disease. J Chromatogr B 1998; 714:87-98.

54. Ma S, Lin Y Y, Turino G M. Measurements of desmosine and isodesmosine by mass spectrometry in COPD. Chest 2007; 131:1363-71.

55. Luisetti M, Ma S, Iadarola P, Stone P J, Viglio S, Casado B, et al. Desmosine as a biomarker of elastin degradation in COPD: Current status and future directions. Eur Respir J 2008; 32:1146-57.

56. Kaga N, Soma S, Fujimura T, Seyama K, Fukuchi Y, Murayama K. Quantification of elastin crosslinking amino acids, desmosine and isodesmosine, in hydrolysates of rat lung by ion-pair liquid chromatography-mass spectrometry. Anal Biochem 2003; 318:25-9.

57. Boutin M, Berthelette C, Gervais F G, Scholand M B, Hoidal J, Leppert M F, et al. High-sensitivity nanoLC-MS/MS analysis of urinary desmosine and isodesmosine. Anal Chem 2009; 81:1881-7.

58. Albarbarawi O, Barton A, Lin Z, Takahashi E, Buddharaju A, Brady J, et al. Measurement of urinary total desmosine and isodesmosine using isotope-dilution liquid chromatography-tandem mass spectrometry. Anal Chem 2010; 82:3745-50.

59. Desmosine and Isodesmosine analysis as possible biomarkers for COPD has been among the topics of two recent FDA workshops (2009 and 2010 at Bethesda): a) Turino G M, Lin Y Y. Desmosine and isodesmosine as biomarkers of elastin degradation in COPD and Alpha-1 antitrypsin deficiency. FDA Study Group on "Improving Endpoints, Improving Care: Alpha-1 Antitrypsin Augmentation Therapy and Clinical Trials" Center for Biologics Evaluation and Research, FDA, Bethesda, Md. March 23-24, (2009); b) Svartengren M, Anderson M, Hallberg, Pedersen N (Karolinska Institutet Stockholm); Wollmer P (Clinical Physiology Malmö University Hospital, Malmö Sweden); Dirksen A, Shaker S (Gentofte University Hospital, Hellerup, Denmark); Lindberg C, Forsman-Semb K, Lloyd A (Astra-Zeneca Respiratory and Inflammation Clinical and Discovery Groups); Turino G M, Lin Y Y (James P. Mara Center for Lung Disease, St. Luke's-Roosevelt Hospital Centre); Kilty I, Thompson N, Palmer C (Pfizer), Gervais F, Boutinn, et al. (Merck & Co). Study Group on "Desmosine and Isodesmosine as Biomarkers for COPD" FDA, Bethesda, Md., January 26-27 (2010).

60. Pauwels R A, Buist A S, Calverley P M R, Jenkins C R, Hurd S S. Global strategy for the diagnosis, management, and prevention of chronic obstructive pulmonary disease. NHLBI/WHO global initiative for Chronic Obstructive Lung Disease (GOLD) workshop summary. Am J Respir Crit Care Med 2001; 163:1256-76.

61. Pratt D A, Daniloff Y, Duncan A, Robinson S P, Automated analysis of the pyridinium crosslinks of collagen in tissue and urine using solid-phase extraction and reversed-phase high-performance liquid chromatography. Anal Biochem 1992; 207:168-175.

62. James I T, Walne A J, Perrett D. Automated solid-phase extraction with high-performance liquid chromatography analysis of pyridinium crosslinks. Anal Biochem 1996; 240:29-36.

63. Kindt E, Rossi D T, Gueneva-Boucheva K, Hallak H. Quantitative method for biomarkers of collagen degradation using liquid chromatography tandem mass spectrometry. Anal Biochem 2000; 283:71-6.

64. Abraham P A, Perejda A J, Carnes W H, Uitto J. Marfan syndrome: Demonstration of abnormal elastin in aorta. J Clin Invest 1982; 70:1245-52.

65. Stone P J, Korn J H, North H, Lally E V, Miller L C, Tucker L B, et al. Cross-linked elastin and collagen degradation products in the urine of patients with scleroderma. Arthritis Rheumatism 1995; 38:517-24.

66. Annovazzi L, Viglio S, Gheduzzi D, Pasquali-Ronchetti I, Zanone C, Getta G, Ladarola P. High level of desmosine in urine and plasma of patients with pseudoxanthoma elasticum. Europ J Clin Invest 2004; 34:156-64.

67. Stone P J. Potential use of collagen and elastin degradation markers for monitoring liver fibrosis I schistosomiasis. Acta Trop 2000; 77:97-9.

68. World Health Organization fact sheet No. 315, November 2009 (www.who.int/mediacentre/factsheets/fs315/en/).

69. Barnes P J. Chronic Obstructive Pulmonary Disease. New England J of Med 2000; 343(4): 269-280.

70. Flouris A D, Metsios G S, Carrillo A E, Jamurtas A Z et al. Acute and short-term effects of secondhand smoke on lung function and cytokine production. Am J Respir Crit Care Me 2009; 179:1029-1033.

71. World Health Organization—Environmental burden of disease series No. 18 (2010): Second Hand Smoke (www.who.int/quantifying_ehimpacts/publications/ebd18/en/).

72. Iso H, Shimamoto T, Sato S et al. Passive smoking and plasma fibrinogen concentrations. Am J of Epidemiology 1996; 144:1151-1154.

73. Clark III J D, Wilkinson J D, LeBlanc W G et al. Inflammatory markers and secondhand tobacco smoke exposure among U.S. workers. Am J of Industrial Medicine 2008; 51:626-632.

74. Panagiotakos D B, Ptsavos C, Chrysohoou C et al. Effect of exposure to secondhand smoke on markers of inflammation: the ATTICA study. Am J of Med 2004; 116: 145-150.

75. Menzies D, Nair A, Williamson P A, Schembri S et al. Respiratory symptoms, pulmonary function, and markers of inflammation among bar workers before and after a legislative ban on smoking in public places. JAMA; 296:1742-1748.

76. Otsuka R, Watanabe H, Hirata K, Tokai K et al. Acute effects of passive smoking on the coronary circulation in healthy young adults. JAMA 2001; 286:436-441.

77. Whincup P H, Gilg J A, Emberson J R, Jarvis M J et al. Passive smoking and risk of coronary heart disease and stroke: prospective study with cotinine measurement. BMJ 2004; 10:1-6.

78. Benowitz N L. Cotinine as a biomarker of environmental tobacco smoke exposure. Epidemiol Rev 1996; 18:188-204.

79. Senior R M, Betsuyaku T. Lung elastin and elastase in COPD. Eur Resp Rev 2002; 12.

80. Chrzanowski P, Keller S, Cerreta J, et al. Elastin content of normal and emphysematous lung parenchyma. Am. J Med 1980; 69: 351-359.

81. Senior R M, Griffen G L, Mecham R P. Chemotactic activity of elastin-derived peptides. J Clin Invest 1980; 66:859-862.
82. Venn A, Britton J. Exposure to secondhand smoke and biomarkers of cardiovascular disease risk in never-smoking adults. Circulation 2007; 990-995.
83. Hiroshi Y, Horiuchi K, Takano R, Nagano T, Shimizu M, Kitajima M, Murayama N and Shono F: Human blood concentrations of cotinine, a biomonitoring marker for tobacco smoke, extrapolated from nicotine metabolism in rats and humans and physiologically based pharmacokinetic modeling. Int J Environ Res Public Health 2010:7: 3406-21.
84. Sandberg L B, Soskel N T, Leslie J G: Elastin structure, biosynthesis, and relation to disease states. N Engl J Med. 1981; 304:566-579.
85. Hogg J C, Timens W: The pathology of chronic obstructive pulmonary disease. Ann Rev Pathol Mech Dis. 2009; 4:435-459.
86. Fukuda Y, Masuda Y, Ishizaki M, Masugi Y, Ferrans V J: Morphogenesis of abnormal elastic fibers in lungs of patients with panacinar and centriacinar emphysema. Hum Pathol. 1989; 20:652-659.
87. Vlahovic G, Russell M L, Mercer R R, Crapo J D: Cellular and connective tissue changes in alveolar septal walls in emphysema. Am J Respir Crit Care Med. 1999; 160:2086-2092.
88. Turino G M, Senior R M, Garg B D, Keller S, Levi M M, Mandl I: Serum elastase inhibitor deficiency and alpha1-antitrypsin deficiency in patients with obstructive emphysema. Science. 1969; 165:709-711.
89. Snider G L, Lucey E C, Stone P J: Animal-models of emphysema: Am Rev Respir Dis. 1986; 133:149-169.
90. Gottlieb D J, Stone P J, Sparrow D, Gale M E, Weiss S T, Snider G L, O'Connor G T: Urinary desmosine excretion in smokers with and without rapid decline of lung function—the normative aging study. Am J Respir Crit Care Med. 1996; 154: 1290-1295.
91. Darnule T V, McKee M, Darnule A T, Turino G M, Mandl I: Solid-phase radioimmunoassay for estimation of elastin peptides in human-sera. Anal Biochem. 1982; 122:302-307.
92. Dillon T J, Walsh R L, Scicchitano R, Eckert B, Cleary E G, McLennan G: Plasma elastin-derived peptide levels in normal adults, children, and emphysematous subjects—physiological and computed tomographic scan correlates. Am Rev RespirDis. 1992; 146:1143-1148.
93. Akers S, Kucich U, Swartz M, Rosen G, Glass M, Rosenbloom J, Kimbel P, Weinbaum G: Specificity and sensitivity of the assay for elastin-derived peptides in chronic obstructive pulmonary disease. Am Rev Respir Dis. 1992; 145:1077-1081.
94. Reiser K, McCormick R J, Rucker R B: Enzymatic and nonenzymatic cross-linking of collagen and elastin. FASEB J. 1992; 6:2439-2449.
95. Foster J A, Bruenger E, Rubin L, Imberman M, Kagan H, Mecham R, Franzblau C: Circular-dichroism studies of an elastin crosslinked peptide. Biopolymers. 1976; 15:833-841.
96. Gerber G E, Anwar R A: Comparative studies of the crosslinked regions of elastin from bovine ligamentum nuchae and bovine, porcine and human aorta. Biochem J. 1975; 149:685-695.
97. Mecham R P, Foster J A: Structural model for desmosine crosslinked peptides. Biochem J. 1978; 173:617-625.
98. Brown-Augsburger P, Tisdale C, Broekelmann T, Sloan C, Mecham R P: Identification of an elastin cross-linking domain that joins 3 peptide chains—possible role in nucleated assembly. J Biol Chem. 1995; 270:17778-17783.
99. Mecham R P, Broekelmann T J, Fliszar C J, Shapiro S D, Welgus H G, Senior R M: Elastin degradation by matrix metalloproteinases—cleavage site specificity and mechanisms of elastolysis. J Biol Chem. 1997; 272: 18071-18076.
100. Barroso B, Abello N, Bischoff R: Study of human lung elastin degradation by different elastases using high-performance liquid chromatography/mass spectrometry. Anal Biochem. 2006; 358:216-224.
101. Russell REK, Thorley A, Culpitt S V, Dodd S, Donnelly L E, Demattos C,
Fitzgerald M, Barnes P J: Alveolar macrophage mediated elastolysis: roles of matrix metalloproteinases, Experimental Lung Research Lung Elastin-Derived Peptides in COPD 557 cysteine, and serine proteases. Am J Physiol Lung Cell Mol Physiol. 2002; 283: L867-L873.
102. Senior R M, Griffin G L, Mecham R P: Chemotactic responses of fibroblasts to tropoelastin and elastin-derived peptides. J Clin Invest. 1982; 70:614-618.
103. Hunninghake G W, Davidson J M, Rennard S, Szapiel S, Gadek J E, Crystal R G: Elastin fragments attract macrophage precursors to diseased sites in pulmonary-emphysema. Science. 1981; 212:925-927.
104. Yusa T, Blood C H, Zetter B R: Tumor-cell interactions with elasting implications for pulmonary metastasis. Am Rev Respir Dis. 1989; 140:1458-1462.
105. Houghton A M, Quintero P A, Perkins D L, Kobayashi D K, Kelley D G, Marconcini L A, Mecham R P, Senior R M, Shapiro S D: Elastin fragments drive disease progression in a murine model of emphysema. J Clin Invest. 2006; 116:753-759.
106. Lee S-H, Goswami S, Grudo A, Song L-z, Bandi V, Goodnight-White S, Green L, Hacken-Bitar J, Huh J, Bakaeen F, et al.: Antielastin autoimmunity in tobacco smoking-induced emphysema. Nat Med. 2007; 13:567-569.
107. Cosia M G, Saetta M, Agusti A: Immunologic aspects of chronic obstructive pulmonary disease. N Engl J Med. 2009; 360:2445-2454.
108. Twumasi D Y, Liener I E: Protease from purulent sputum, purification and properties of the elastase and chymotrypsin-like enzymes. J Biol Chem 1972; 252: 1917-1926.
109. Banda M J, Werb Z: Mouse macrophage elastase. Purification and characterization as metalloproteinase. Biochem J. 1981; 193:589-605.
110. Shapiro S D, Griffin G, Gilbert D J, Jenkins N A, Copeland N G, Welgus H G, Senior R M, Ley T J: Molecular cloning, chromosomal localization, and bacterial expression of a murine macrophage metalloelastase. J Biol Chem. 1992; 267: 4664-4671.
111. Shapiro S D, Kobayashi D K, Ley T J: Cloning and characterization of a unique elastolytic metalloproteinase produced by human alveolar macrophages. J Biol Chem. 1993; 268:23824-23829.
112. Biemann K: Sequencing of peptides by tandem mass spectrometry and high-energy collision-induced dissociation. Methods Enzymol. 1990; 193:455-479.
113. Papayannopoulos I A: The interpretation of collision-induced dissociation tandem mass-spectra of peptides. Mass Spectrom Rev. 1995; 14:49-73.
114. Vrhovski B, Weiss A S: Biochemistry of tropoelastin. Eur J Biochem. 1998; 258:1-18.

115. Indik Z, Yeh H, Ornsteingoldstein N, Sheppard P, Anderson N, Rosenbloom J C, Peltonen L, Rosenbloom J: Alternative splicing of human elastin messenger-RNA indicated by sequence analysis of cloned genomic and complementary-DNA. Proc Natl Acad Sci USA. 1987; 84:5680-5684.
116. Senior R M, Griffin G L, Mecham R P, Wrenn D S, Prasad K U, Urry D W: Val-Gly-Val-Ala-Pro-Gly, a repeating peptide in elastin, is chemotactic for fibroblasts and monocytes. J Cell Biol. 1984; 99:870-874.
117. Gosline J M: Hydrophobic interaction and a model for elasticity of elastin. Biopolymers. 1978; 17:677-695.
118. Urry D W: Protein elasticity based on conformations of sequential polypeptides—the biological elastic fiber. J Protein Chem. 1984; 3:403-436.
119. Urry D W: Entropic elastic processes in protein mechanisms. 1. Elastic structure due to an inverse temperature transition and elasticity due to internal chain dynamics. J Protein Chem. 1988; 7:1-34.
120. Morelli MAC, Bisaccia F, Spisani S, DeBiasi M, Traniello S, Tamburro A M: Structure-activity relationships for some elastin-derived peptide chemoattractants. J Pept Res. 1997; 49:492-499.
121. Brassart B, Fuchs P, Huet E, Alix A J P, Wallach J, Tamburro A M, Delacoux F, Haye B, Emonard H, Hornebeck W, et al.: Conformational dependence of collagenase (matrix metalloproteinase-1) up-regulation by elastin peptides in cultured fibroblasts. J Biol Chem. 2001; 276:5222-5227.
122. Starcher B and Peterson B: The kinetics of elastolysis: elastin catabolism during experimentally induced fibrosis. Exp Lung Res. 1999; 25:407-424.
123. Stolk J, Veldhuisen B, Annovazzi L, Zanone C, Versteeg E M, van Kuppevelt, T H, Nieuwenhuizen, W, Iadarola P and Luisetti M: Short-term variability of biomarkers of proteinase activity in patients with emphysema associated with type Z alpha-1 antitrypsin deficiency. Respir Res 2005, 6:47.
124. Starcher B C and Galione M J: Purification and comparisons of elastin from different animal species. Analytical Biochemistry 1976, 74:441-447.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for identifying candidate compounds that are effective to treat, prevent, or ameliorate the effects of a disease characterized by elastin degradation comprising:
    (a) administering a candidate compound to a cell culture model of the disease;
    (b) measuring, by mass spectrometry using an internal standard comprising acylated pyridinoline, the amount of at least one marker of elastin degradation in the cell culture administered the candidate compound, wherein the at least one marker of elastin degradation is selected from the group consisting of desmosine, isodesmosine, and combinations thereof; and
    (c) determining whether the amount of the at least one marker produced by the cell culture administered the candidate compound is different compared to a control cell culture absent the candidate compound, wherein a decrease in the amount of the at least one marker produced by the cell culture administered the candidate compound compared to the control cell culture identifies the candidate compound as effective to treat, prevent, or ameliorate the effects of the disease,
wherein the disease is selected from the group consisting of chronic obstructive pulmonary disease (COPD), COPD with AATD, chronic bronchitis, emphysema, and refractory asthma.

2. The method according to claim 1, wherein the disease is COPD.

3. The method according to claim 1, wherein both desmosine and isodesmosine are measured.

4. The method according to claim 1, wherein the candidate compound is selected from the group consisting of hyaluronic acid, polysaccharide, carbohydrate, small molecules, and RNAi.

5. The method according to claim 1, wherein tandem mass spectrometry is used.

6. A method for identifying candidate compounds that are effective to treat, prevent, or ameliorate the effects of a disease characterized by elastin degradation comprising:
   (a) administering a candidate compound to a cell culture model of the disease;
   (b) measuring, by mass spectrometry using an internal standard comprising acylated pyridinoline, the amount of desmosine and isodesmosine in the cell culture administered the candidate compound; and
   (c) determining whether the amount of desmosine and isodesmosine produced by the cell culture administered the candidate compound is different compared to a control cell culture absent the candidate compound, wherein a decrease in the amount of the desmosine and isodesmosine produced by the cell culture administered the candidate compound compared to the control cell culture identifies the candidate compound as effective to treat, prevent, or ameliorate the effects of the disease,
   wherein the disease is selected from the group consisting of chronic obstructive pulmonary disease (COPD), COPD with AATD, chronic bronchitis, emphysema, and refractory asthma.

7. The method according to claim 6, wherein tandem mass spectrometry is used.

* * * * *